US008921026B2

(12) United States Patent
Hatakeyama et al.

(10) Patent No.: US 8,921,026 B2
(45) Date of Patent: Dec. 30, 2014

(54) BASIC COMPOUND, CHEMICALLY AMPLIFIED RESIST COMPOSITION, AND PATTERNING PROCESS

(75) Inventors: Jun Hatakeyama, Joetsu (JP); Masayoshi Sagehashi, Joetsu (JP); Takeru Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 129 days.

(21) Appl. No.: 13/311,192

(22) Filed: Dec. 5, 2011

(65) Prior Publication Data
US 2012/0141938 A1  Jun. 7, 2012

(30) Foreign Application Priority Data

Dec. 7, 2010 (JP) ................. 2010-272510
Aug. 15, 2011 (JP) ................. 2011-177574

(51) Int. Cl.
 *G03F 7/00* (2006.01)
 *C07D 239/28* (2006.01)
 *G03F 7/004* (2006.01)

(52) U.S. Cl.
 CPC ............ *C07D 239/28* (2013.01); *G03F 7/0045* (2013.01)
 USPC ........................................ 430/270.1; 430/322

(58) Field of Classification Search
 None
 See application file for complete search history.

(56) References Cited

U.S. PATENT DOCUMENTS

| | | | |
|---|---|---|---|
| 6,448,420 | B1 | 9/2002 | Kinsho et al. |
| 7,537,880 | B2 | 5/2009 | Harada et al. |
| 7,598,016 | B2 | 10/2009 | Kobayashi et al. |
| 2002/0098443 | A1 | 7/2002 | Hatakeyama et al. |
| 2004/0072094 | A1 | 4/2004 | Shima et al. |
| 2004/0106063 | A1 | 6/2004 | Hatakeyama et al. |
| 2007/0048806 | A1 | 3/2007 | Charych et al. |
| 2008/0090172 | A1 | 4/2008 | Hatakeyama et al. |
| 2008/0124656 | A1* | 5/2008 | Kobayashi et al. ........ 430/286.1 |
| 2008/0153030 | A1 | 6/2008 | Kobayashi et al. |
| 2008/0200535 | A1 | 8/2008 | Ohmori et al. |
| 2009/0053652 | A1 | 2/2009 | Chakrapani et al. |

FOREIGN PATENT DOCUMENTS

| | | | |
|---|---|---|---|
| CN | 1939916 A | | 4/2007 |
| JP | 09-151175 A | | 6/1997 |
| JP | 2000056457 A | * | 2/2000 |
| JP | 2000122279 A | * | 4/2000 |
| JP | 2000-327633 A | | 11/2000 |
| JP | 2001-194776 A | | 7/2001 |
| JP | 2002-226470 A | | 8/2002 |
| JP | 2002-363148 A | | 12/2002 |
| JP | 2005-084365 A | | 3/2005 |
| JP | 3790649 B2 | | 6/2006 |
| JP | 2006-178317 A | | 7/2006 |
| JP | 2006-282547 A | | 10/2006 |
| JP | 2006-528698 A | | 12/2006 |
| JP | 2008083234 A | * | 4/2008 |
| JP | 2008-111103 A | | 5/2008 |
| JP | 2008-122932 A | | 5/2008 |
| JP | 2008-158339 A | | 7/2008 |
| JP | 2008-239918 A | | 10/2008 |
| JP | 2009-269819 A | | 11/2009 |
| WO | 00/73283 A1 | | 12/2000 |
| WO | 2004/103306 A2 | | 12/2004 |
| WO | 2009/019574 A1 | | 2/2009 |

OTHER PUBLICATIONS

Machine translation of JP 2008-083234, Apr. 10, 2008.*
Machine translation JP 2000-122279. Apr. 28, 2000.*
Machine translation JP 2000-056457. Feb. 25, 2000.*
European Search Report dated Feb. 7, 2012, issued in corresponding European Patent Application No. 11191784.5.
Freuze, Ingrid et al.; "Impact of UV-irradiation on the formation of odorous chloroaldimines in drinking water"; Chemosphere, Pergamon Press, Oxford, GB, vol. 63, No. 10, Jun. 1, 2006, pp. 1660-1666.(cited in European Search Report dated Feb. 7, 2012).
W. Hinsberg et al., "Extendibility of Chemically Amplified Resists: Another Brick Wall?", Proceedings of SPIE, 2003, vol. 5039, pp. 1-14.
Y. Kishikawa et al., "Assessment of trade-off between resist resolution and sensitivity for optimization of hyper-NA immersion lithography", Proceedings of SPIE, 2007, vol. 6520, pp. 65203L-1-65203L-9.
C. W. Wang et al., "Photobase generator and photo decomposable quencher for high-resolution photoresist applications", Proceedings of SPIE, 2010, vol. 7639, pp. 76390W-1-76390W-15.
Japanese Office Action dated Mar. 18, 2014, issued in corresponding Japanese application No. 2011-177574 (2 pages).

* cited by examiner

*Primary Examiner* — Cynthia H Kelly
*Assistant Examiner* — Alyssa L Cepluch
(74) *Attorney, Agent, or Firm* — Westerman, Hattori, Daniels & Adrian, LLP

(57) ABSTRACT

A chemically amplified resist composition comprising a base polymer, an acid generator, and an amine quencher in the form of a β-alanine, γ-aminobutyric acid or δ-aminovaleric acid derivative having an acid labile group-substituted carboxyl group has a high contrast of alkaline dissolution rate before and after exposure and forms a pattern of good profile at a high resolution, minimal roughness and wide focus margin.

9 Claims, No Drawings

US 8,921,026 B2

BASIC COMPOUND, CHEMICALLY AMPLIFIED RESIST COMPOSITION, AND PATTERNING PROCESS

CROSS-REFERENCE TO RELATED APPLICATION

This non-provisional application claims priority under 35 U.S.C. §119(a) on Patent Application Nos. 2010-272510 and 2011-177574 filed in Japan on Dec. 7, 2010 and Aug. 15, 2011, respectively, the entire contents of which are hereby incorporated by reference.

TECHNICAL FIELD

This invention relates to a chemically amplified resist composition comprising a specific basic compound, and more particularly, to a chemically amplified positive or negative resist composition suited for use in the photolithography with KrF excimer laser, ArF excimer laser, EB or EUV radiation, and a patterning process using the same.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the future generation 32-nm node include ultra-high NA lens immersion lithography using a liquid having a higher refractive index than water in combination with a high refractive index lens and a high refractive index resist film, EUV lithography of 13.5 nm wavelength, and double patterning version of the ArF lithography, on which active research efforts have been made.

With respect to high-energy radiation of very short wavelength such as EB or x-ray, hydrocarbons and similar light elements used in resist materials have little absorption. Then polyhydroxystyrene base resist materials are under consideration. Resist materials for EB lithography are practically used in the mask image writing application. Recently, the mask manufacturing technology becomes of greater interest. Reduction projection exposure systems or steppers have been used since the time when the exposure light was g-line. While their demagnification factor was $\frac{1}{5}$, a factor of $\frac{1}{4}$ is now used as a result of chip size enlargement and projection lens diameter increase. It becomes of concern that a dimensional error of a mask has an impact on the dimensional variation of a pattern on wafer. It is pointed out that as the pattern feature is reduced, the value of a dimensional variation on the wafer becomes greater than the value of a dimensional error of the mask. This is evaluated by a mask error enhancement factor (MEEF) which is a dimensional variation on wafer divided by a dimensional error of mask. Patterns on the order of 45 nm often show an MEEF in excess of 4. In a situation including a demagnification factor of $\frac{1}{4}$ and a MEEF of 4, the mask manufacture needs an accuracy substantially equivalent to that for equi-magnification masks.

The exposure system for mask manufacturing made a transition from the laser beam exposure system to the EB exposure system to increase the accuracy of line width. Since a further size reduction becomes possible by increasing the accelerating voltage of the electron gun in the EB exposure system, the accelerating voltage increased from 10 keV to 30 keV and reached 50 keV in the current mainstream system, with a voltage of 100 keV being under investigation.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein crosslinking reaction takes place under the action of acid. Quenchers are often added to these resist compositions for the purpose of controlling the diffusion of the acid to unexposed areas to improve the contrast. The addition of quenchers is fully effective to this purpose. A number of amine quenchers were proposed as disclosed in Patent Documents 1 to 3.

As the pattern feature size is reduced, approaching to the diffraction limit of light, light contrast lowers. In the case of positive resist film, a lowering of light contrast leads to reductions of resolution and focus margin of hole and trench patterns.

For mitigating the influence of reduced resolution of resist pattern due to a lowering of light contrast, an attempt is made to enhance the dissolution contrast of resist film. One such attempt is a chemically amplified resist material utilizing an acid amplifying mechanism that a compound is decomposed with an acid to generate another acid. In general, the concentration of acid creeps up linearly with an increase of exposure dose. In the case of the acid amplifying mechanism, the concentration of acid jumps up non-linearly as the exposure dose increases. The acid amplifying system is beneficial for further enhancing the advantages of chemically amplified resist film including high contrast and high sensitivity, but worsens the drawbacks of chemically amplified resist film that environmental resistance is degraded by amine contamination and maximum resolution is reduced by an increase of acid diffusion distance. The acid amplifying system is very difficult to control when implemented in practice.

Another approach for enhanced contrast is by reducing the concentration of amine with an increasing exposure dose. This may be achieved by applying a compound which loses the function of quencher upon light exposure.

With respect to the acid labile group used in methacrylate polymers for the ArF lithography, deprotection reaction takes place when a photoacid generator capable of generating a sulfonic acid having fluorine substituted at α-position (referred to "α-fluorinated sulfonic acid") is used, but not when an acid generator capable of generating a sulfonic acid or carboxylic acid not having fluorine substituted at α-position (referred to "α-non-fluorinated sulfonic acid") is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher.

Further, the sulfonium or iodonium salt capable of generating an α-non-fluorinated sulfonic acid functions as a photo-degradable quencher as well since it loses the quencher function by photo-degradation.

Non-Patent Document 3 points out that the addition of a photo-degradable quencher expands the margin of a trench pattern although the structural formula is not illustrated. However, it has only a little influence on performance improvement. There is a desire to have a quencher for further improving contrast.

CITATION LIST

Patent Document 1: JP-A 2001-194776
Patent Document 2: JP-A 2002-226470
Patent Document 3: JP-A 2002-363148
Non-Patent Document 1: SPIE Vol. 5039 μl (2003)
Non-Patent Document 2: SPIE Vol. 6520 p65203L-1 (2007)
Non-Patent Document 3: SPIE Vol. 7639 p76390W (2010)

DISCLOSURE OF INVENTION

An object of the invention is to provide a positive or negative resist composition, typically a chemically amplified positive or negative resist composition, which exhibits a high resolution surpassing prior art positive resist compositions, and offers a wide resolution margin for hole and trench patterns in the case of positive composition, and a high resolution for isolated line patterns in the case of negative composition; a pattern forming process using the same; and a basic compound for use therein.

Seeking for the currently demanded high-resolution resist, the inventors have found that a chemically amplified positive or negative resist composition comprising an amine quencher in the form of a β-alanine, γ-aminobutyric acid or 5-aminovaleric acid derivative having an acid labile group-substituted carboxyl group and an acid generator has a high contrast and forms a pattern at a resolution and rectangularity after development; and that the composition which is positive offers a high resolution and a wide focus margin for hole and trench patterns, and the composition which is negative offers a high resolution for isolated line patterns.

While JP-A 2002-363148 cited above discloses tertiary amine and morpholine compounds having an acid labile group-substituted carboxyl group, the inventors have found that a β-alanine, γ-aminobutyric acid or 5-aminovaleric acid derivative having a primary or secondary amino group having an acid labile group-substituted carboxyl group is fully effective for suppressing acid diffusion and improving contrast in a chemically amplified resist composition to which an acid generator is added.

The chemically amplified positive or negative resist composition has many advantages including a high dissolution contrast of resist film, and a wide resolution margin for hole and trench patterns in the case of positive composition, and a high resolution for isolated line patterns in the case of negative composition. Owing to these advantages, the composition is readily applicable in the industry and very useful as the VLSI-forming resist material and mask pattern-forming material.

In one aspect, the invention provides a chemically amplified resist composition comprising a base polymer, an acid generator, and a basic compound of the general formula (1).

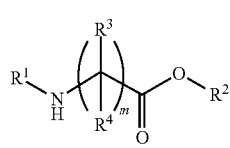

(1)

Herein $R^1$ is hydrogen, or a straight, branched or cyclic $C_1$-$C_{30}$ alkyl, $C_6$-$C_{30}$ aryl, $C_7$-$C_{30}$ aralkyl, $C_2$-$C_{30}$ alkenyl, $C_2$-$C_{10}$ alkynyl, or $C_4$-$C_{12}$ heterocyclic-bearing group, or a combination of such groups, which group may contain a hydroxyl, mercapto, carboxyl, ether, thio ether, ester, sulfonic acid ester, sulfonyl, lactone ring, carbonyl, cyano, nitro, halogen, trifluoromethyl, amide, imide, sulfonamide, carbonate, sulfide, —N=CR—O—, —N=CR—S—, or =N—O—N= moiety, or $R^1$ may be an acid labile group; R is hydrogen, mercapto, hydroxyl or $C_1$-$C_3$ alkyl, or may bond with the nitrogen atom in formula (1) to form a ring; $R^2$ is an acid labile group; $R^3$ and $R^4$ each are hydrogen or a straight or branched $C_1$-$C_4$ alkyl group; and m is an integer of 2 to 4.

The resist composition which is positive may further comprise an organic solvent and more preferably a dissolution inhibitor. The resist composition which is negative may further comprise an organic solvent and typically a crosslinker. The resist composition may further comprise a surfactant.

In another aspect, the invention provides a process for forming a pattern comprising the steps of applying the resist composition defined above onto a substrate, baking to form a resist film, exposing the resist film to high-energy radiation, and developing the exposed film with a developer.

In a preferred embodiment, the high-energy radiation is ArF excimer laser radiation of 193 nm wavelength or KrF excimer laser radiation of 248 nm wavelength. In another preferred embodiment, the high-energy radiation is electron beam or extreme ultraviolet radiation of 3 to 15 nm wavelength.

In a further aspect, the invention provides a basic compound with a molecular weight of at least 240 having the general formula (Q).

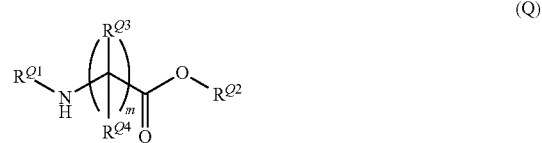

(Q)

Herein $R^{Q1}$ is hydrogen, or a straight, branched or cyclic $C_1$-$C_{30}$ alkyl, $C_6$-$C_{30}$ aryl, $C_7$-$C_{30}$ aralkyl, $C_2$-$C_{30}$ alkenyl, $C_2$-$C_{10}$ alkynyl, or $C_4$-$C_{12}$ heterocyclic-bearing group, or a combination of such groups, which group may contain a hydroxyl, mercapto, carboxyl, ether, thio ether, ester, sulfonic acid ester, sulfonyl, lactone ring, carbonyl, cyano, nitro, halogen, trifluoromethyl, amide, imide, sulfonamide, carbonate, sulfide, —N=CR—O—, —N=CR—S—, or =N—O—N= moiety, or $R^{Q1}$ may be an acid labile group; R is hydrogen, mercapto, hydroxyl or $C_1$-$C_3$ alkyl, or may bond with the nitrogen atom in formula (Q) to form a ring; $R^{Q2}$ is a tertiary alkyl group; $R^{Q3}$ and $R^{Q4}$ each are hydrogen or a straight or branched $C_1$-$C_4$ alkyl group; and m is an integer of 2 to 4.

The chemically amplified positive or negative resist compositions are used not only in the lithography for semiconductor circuit formation, but also in the formation of mask circuit patterns, micro-machines, and thin-film magnetic head circuits.

ADVANTAGEOUS EFFECTS OF INVENTION

The resist compositions have many advantages including a high contrast of alkaline dissolution rate before and after exposure, a high resolution, a good pattern profile after exposure, minimized roughness, and a wide focus margin (DOF). There are provided chemically amplified positive or negative resist compositions which are very useful as the fine pattern-forming resist material for the fabrication of VLSI and photomasks, and the pattern-forming resist material in the KrF excimer laser, ArF excimer laser, EB and EUV lithography.

DESCRIPTION OF EMBODIMENTS

As used herein, the singular forms "a," "an" and "the" include plural referents unless the context clearly dictates otherwise. The terminology "$C_x$—$C_y$", as applied to a particular unit, such as, for example, a chemical compound or a chemical substituent group, means having a carbon atom content of from "x" carbon atoms to "y" carbon atoms per such unit.

The abbreviation EB stands for electron beam, EUV for extreme ultraviolet, PEB for post-exposure bake, LWR for line width roughness, LER for line edge roughness, and DOF for depth of focus.

The invention pertains to a β-alanine, γ-aminobutyric acid or 5-aminovaleric acid derivative having an acid labile group-substituted carboxyl group, represented by the general formula (1).

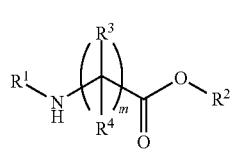

(1)

Herein $R^1$ is hydrogen, or a straight, branched or cyclic $C_1$-$C_{30}$ alkyl group, a $C_6$-$C_{30}$ aryl group, a $C_7$-$C_{30}$ aralkyl group, a $C_2$-$C_{30}$ alkenyl group, a $C_2$-$C_{10}$ alkynyl group, or a $C_4$-$C_{12}$ heterocyclic-bearing group, or a combination of such groups, which group may contain a hydroxyl, mercapto, carboxyl, ether, thio ether, ester (—COO—), sulfonic acid ester, sulfonyl, lactone ring, carbonyl, cyano, nitro, halogen, trifluoromethyl, amide, imide, sulfonamide, carbonate, sulfide, —N=CR—O—, —N=CR—S—, or =N—O—N= moiety. Alternatively, $R^1$ is an acid labile group. R is hydrogen, mercapto, hydroxyl or $C_1$-$C_3$ alkyl, or may bond with the nitrogen atom in formula (1) to form a ring. $R^2$ is an acid labile group. $R^3$ and $R^4$ each are hydrogen or a straight or branched $C_1$-$C_4$ alkyl group, and m is an integer of 2 to 4.

As illustrated by the reaction schemes below, the β-alanine, γ-aminobutyric acid or 5-aminovaleric acid derivative having an acid labile group-substituted carboxyl group undergoes intramolecular dehydrating condensation reaction due to deprotection in the presence of an acid, to form a lactam, for example, the 5-aminovaleric acid forming δ-lactam. Due to the presence of an electron-attractive carbonyl group adjacent the nitrogen atom, the lactam is extremely low basic and has a low quencher function. This suggests that the β-alanine, γ-aminobutyric acid or 5-aminovaleric acid derivative having an acid labile group-substituted carboxyl group functions as a quencher in a region where less acid is generated due to a low exposure dose, but loses the quencher function in a region where more acid is generated. This leads to an improved contrast in the more acid generated region, improving the resolution and DOF margin for trench and hole patterns. The effect of improved contrast in the more acid generated region is the same as achieved by the addition of an acid amplifier. Although the addition of an acid amplifier leads to an abrupt increase of acid diffusion whereby resolution can be degraded, the use of the amine compound according to the invention brings only a slight increase of acid diffusion.

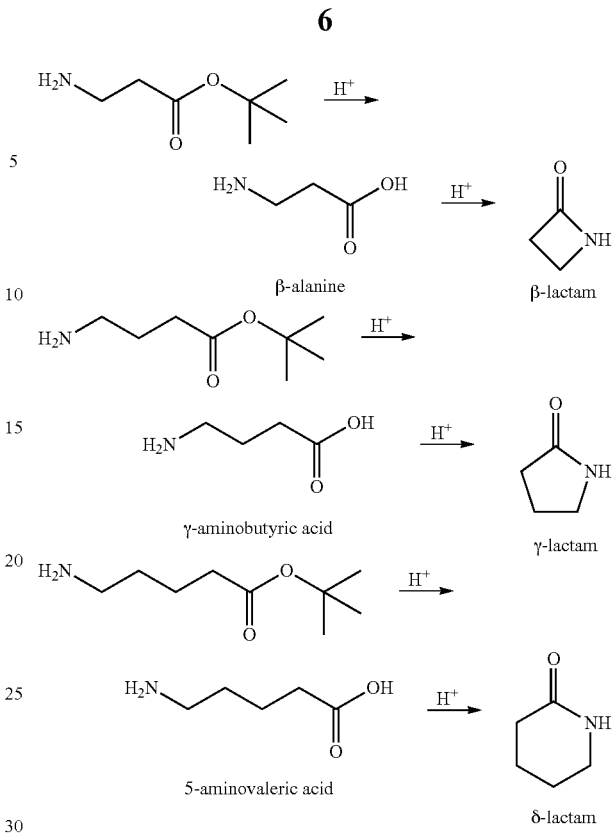

Examples of $R^3$, $R^4$ and m in formula (1) are illustrated below by the overall structure of the compound of formula (1).

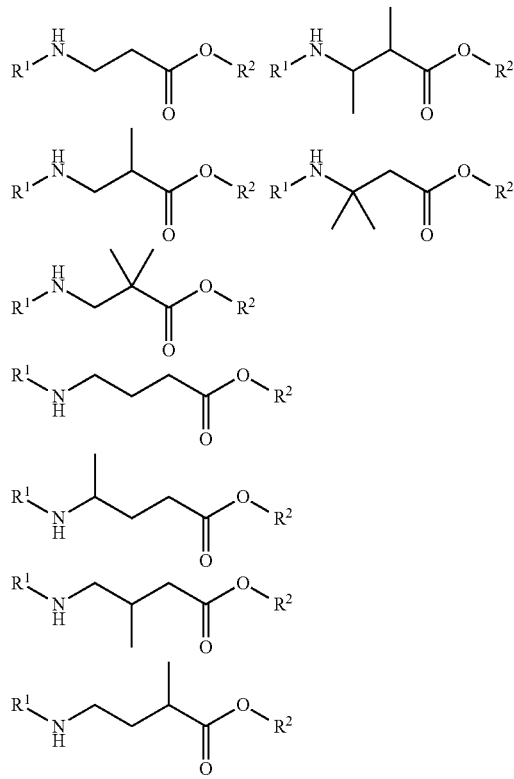

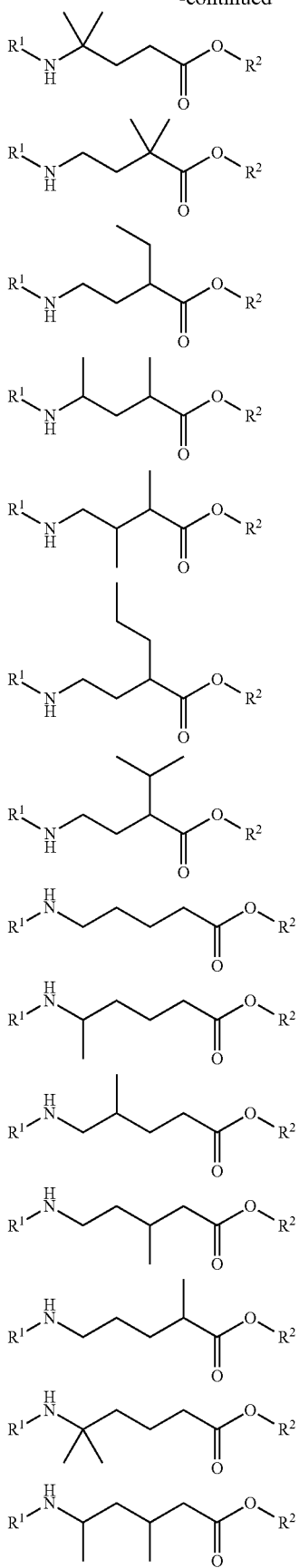
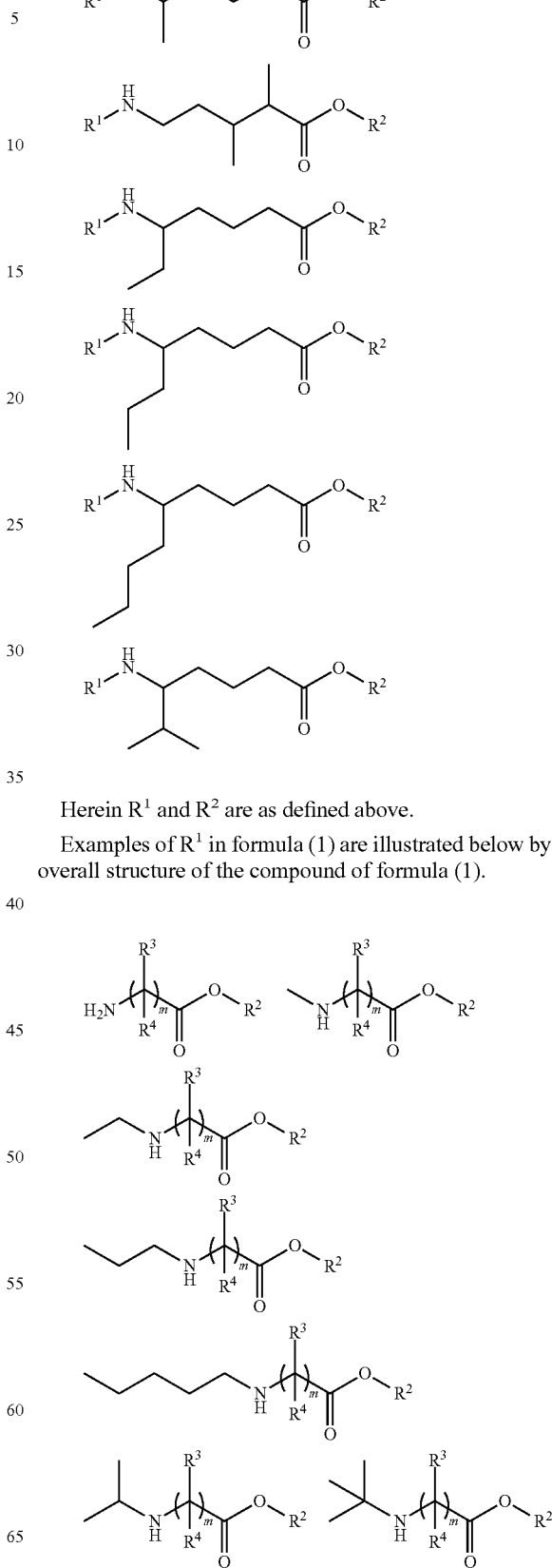
Herein R¹ and R² are as defined above.
Examples of R¹ in formula (1) are illustrated below by the overall structure of the compound of formula (1).

-continued
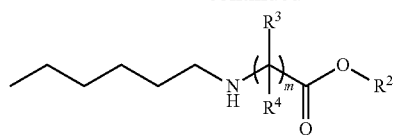
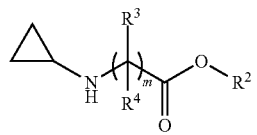
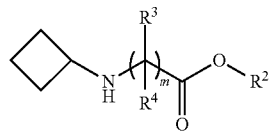
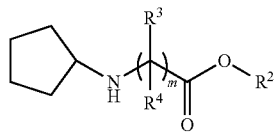
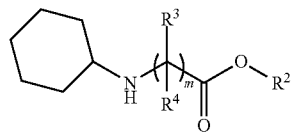
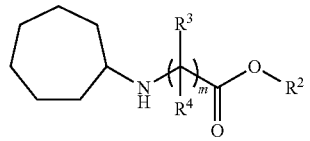
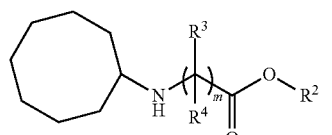
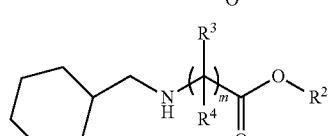
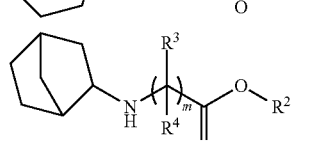
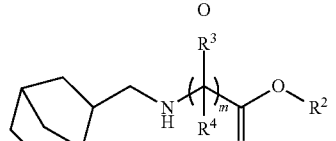
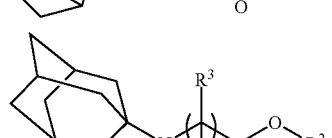
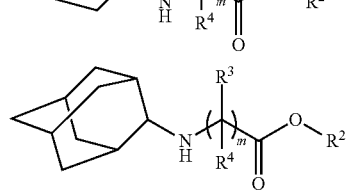
-continued
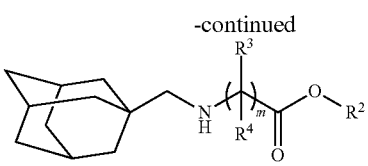
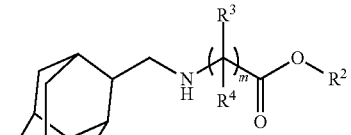
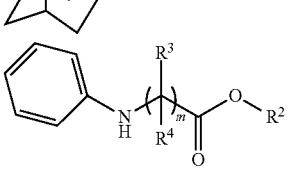
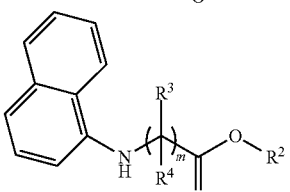
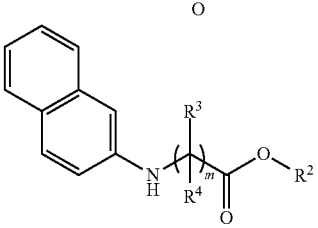
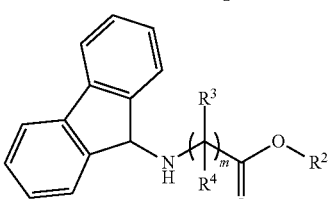
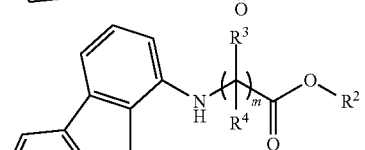
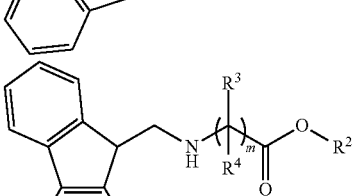
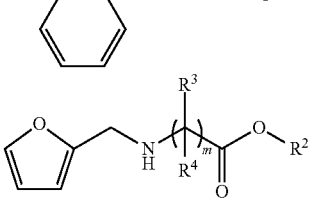
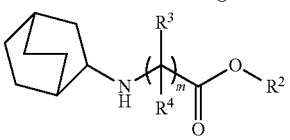

-continued
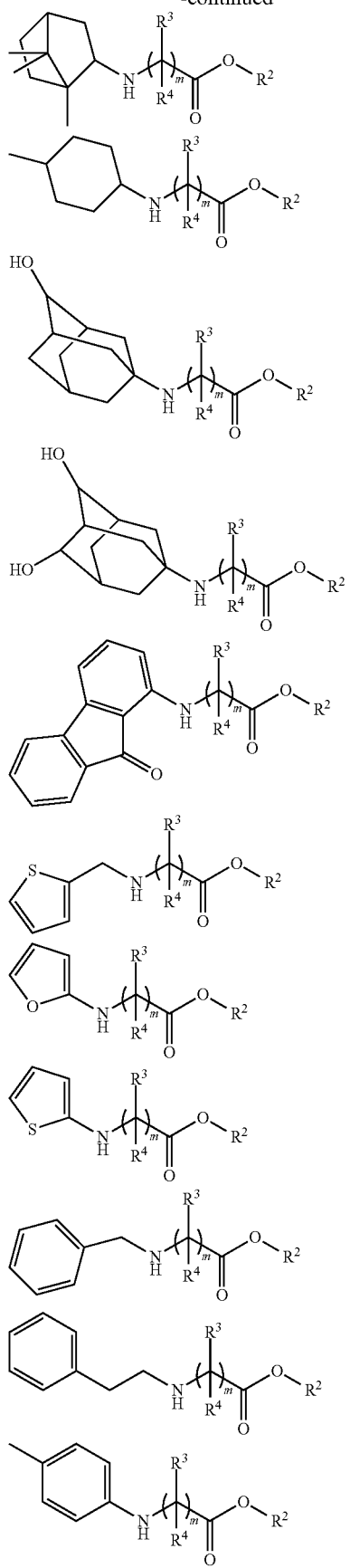
-continued
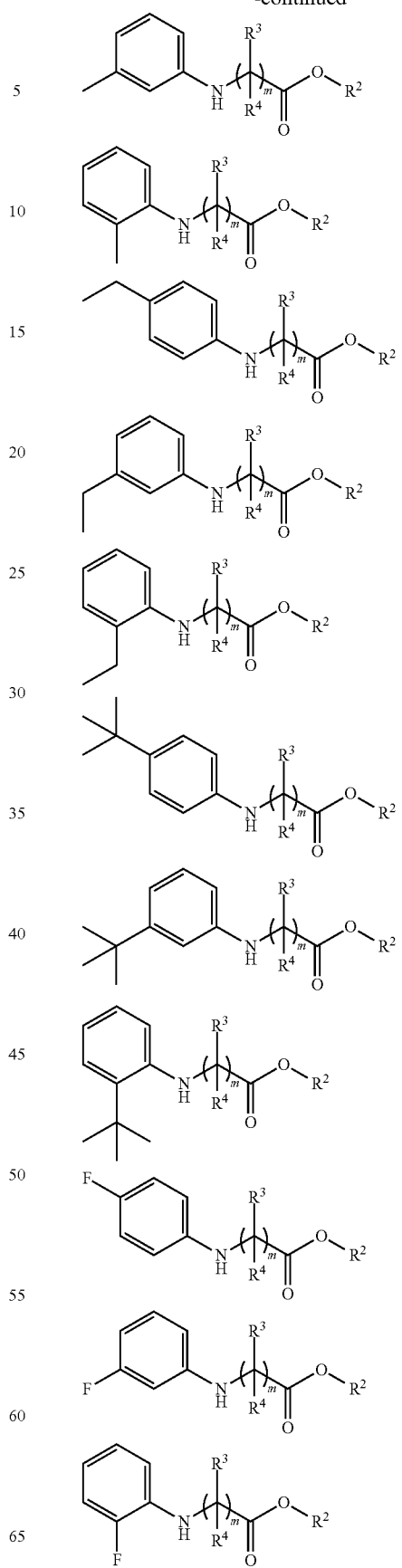

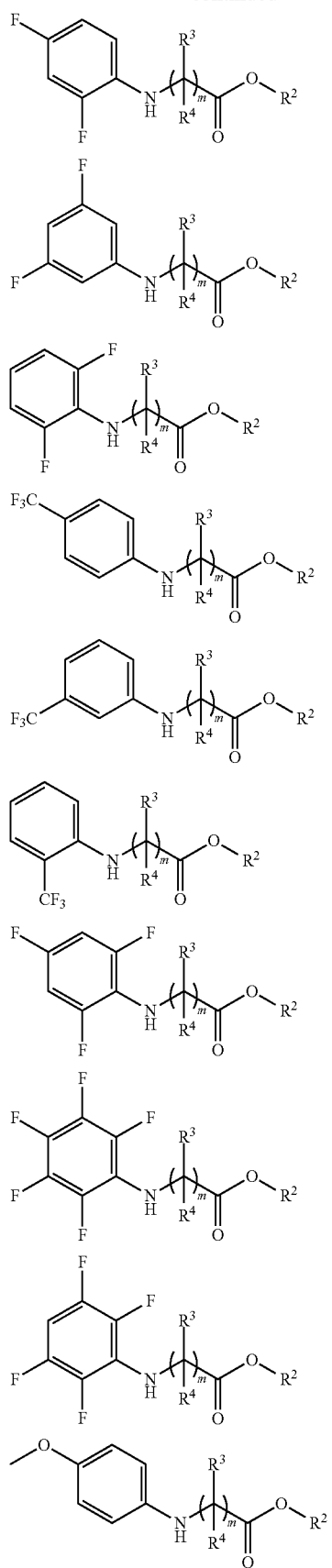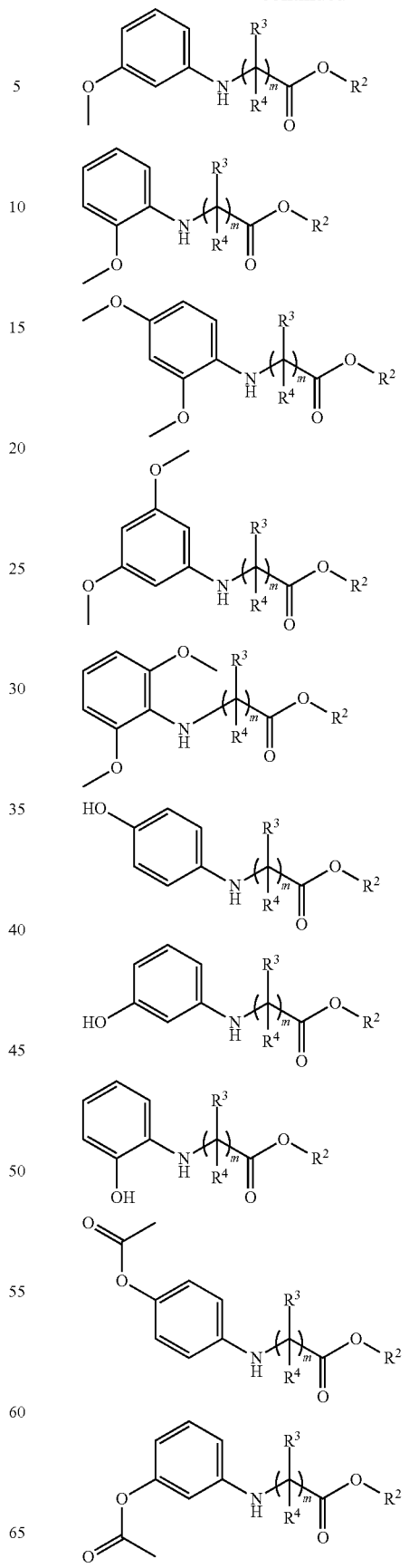

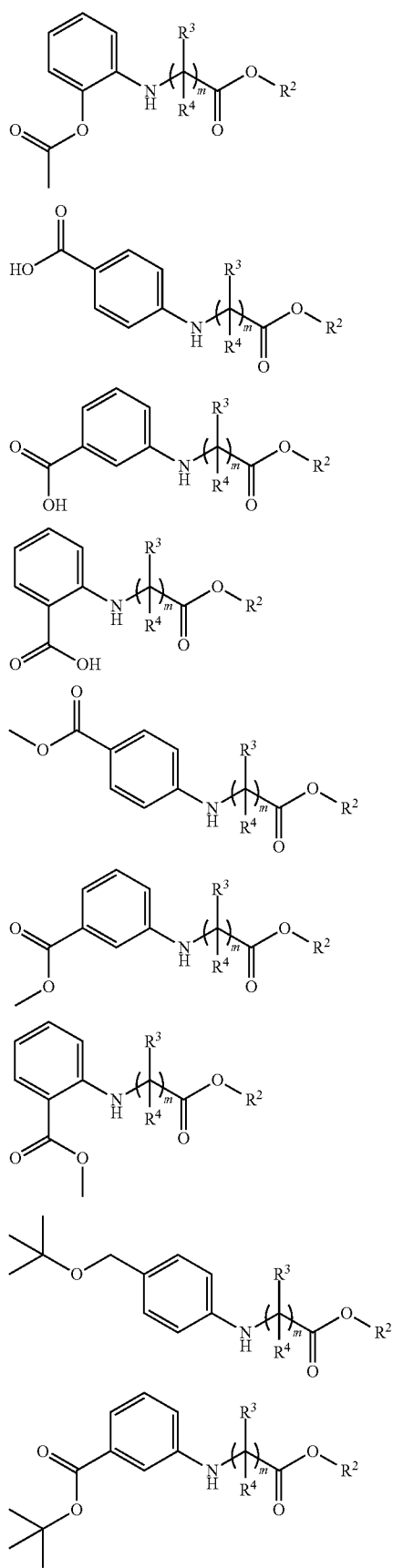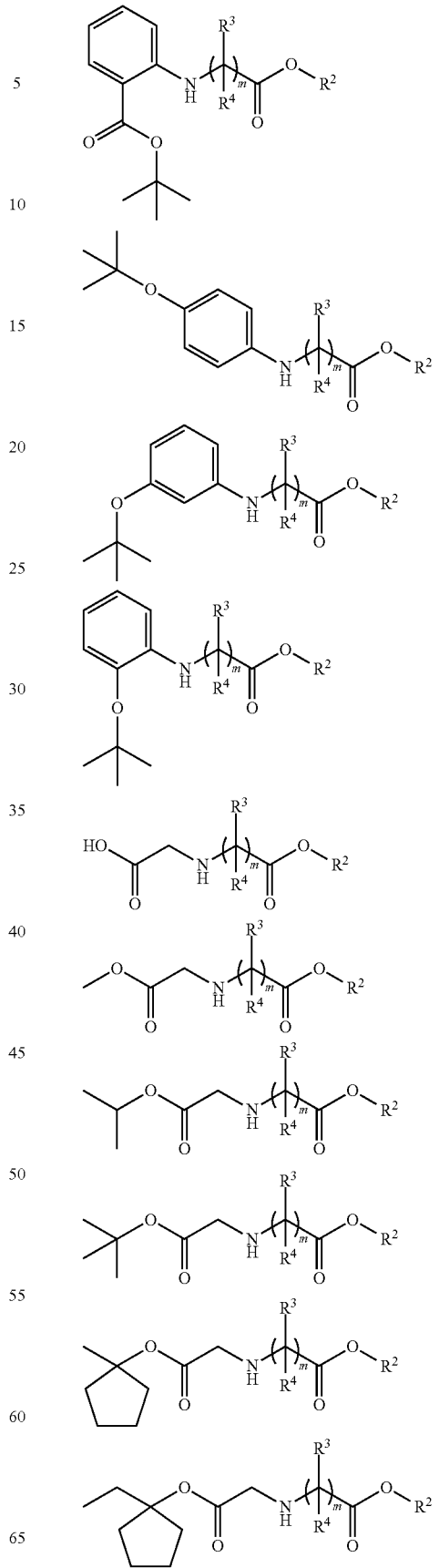

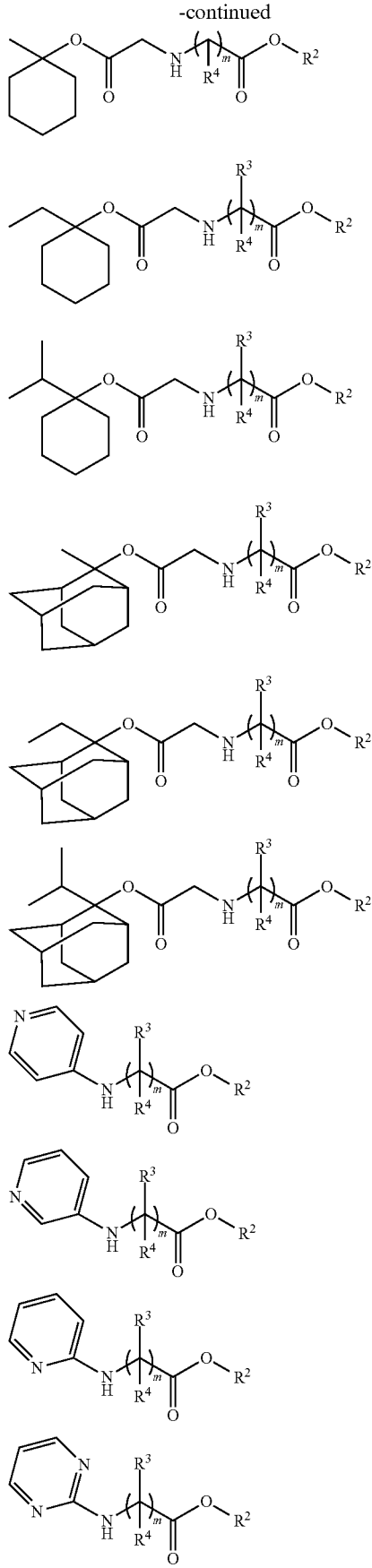
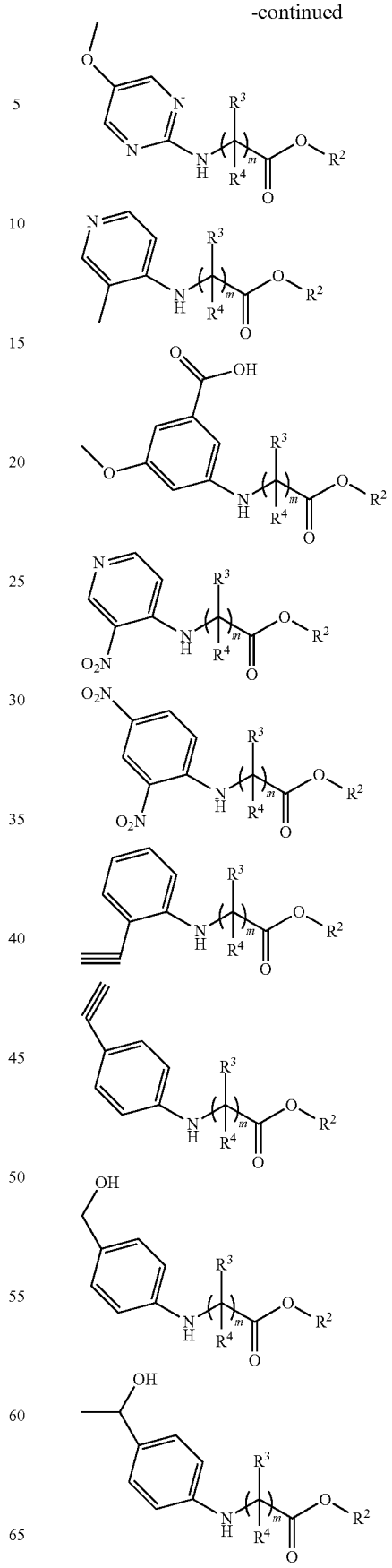

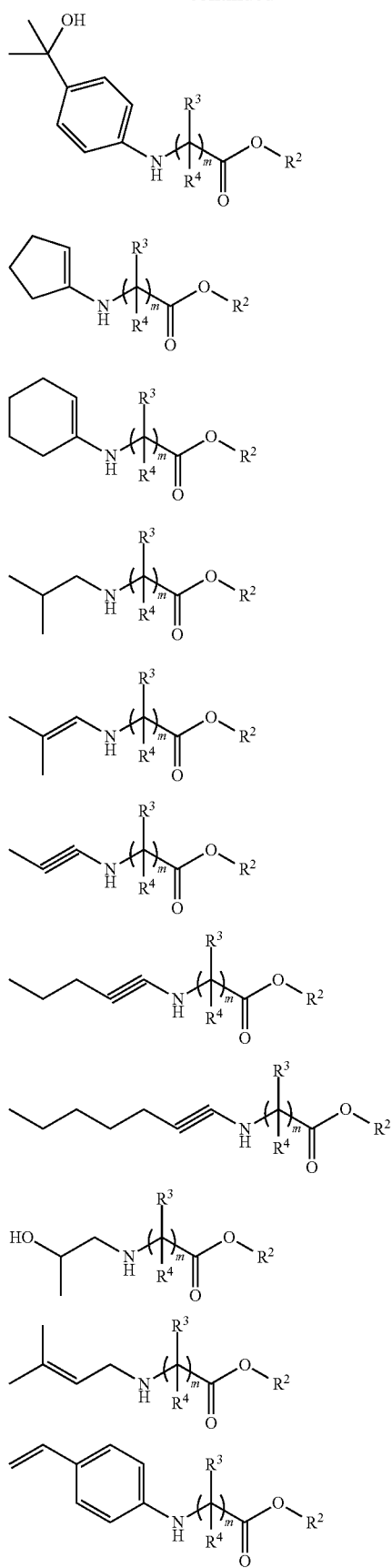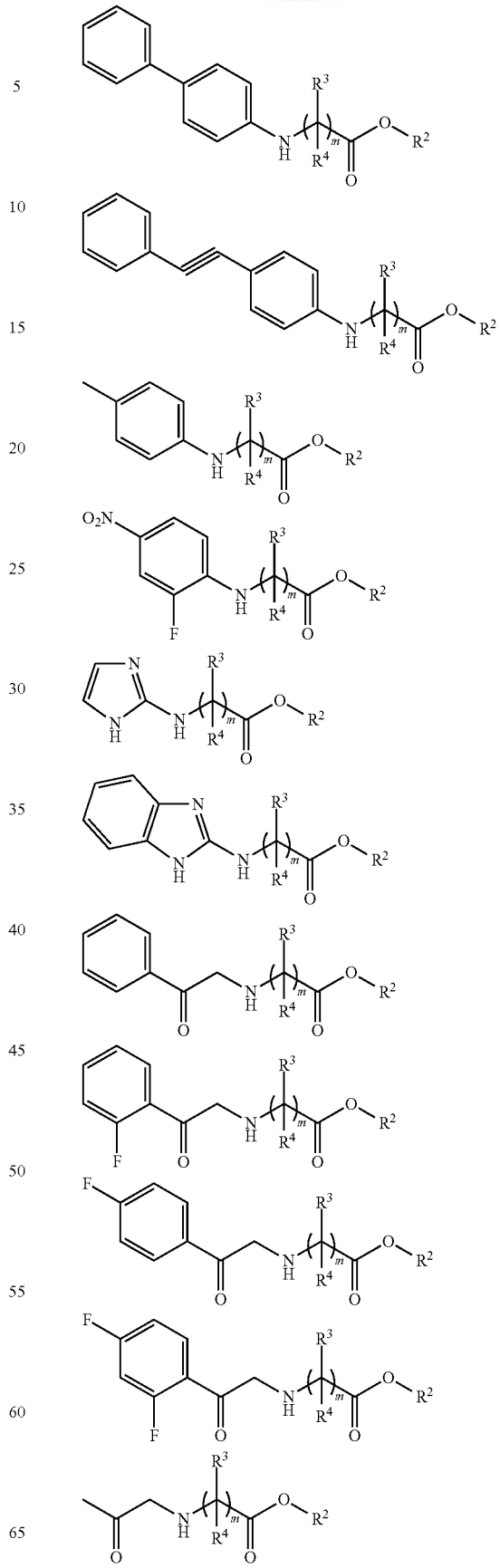

-continued
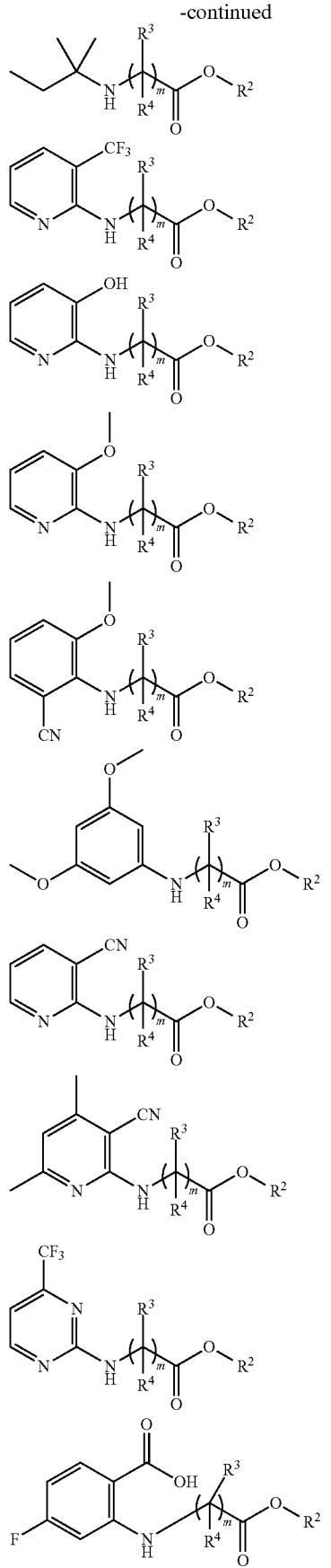
-continued
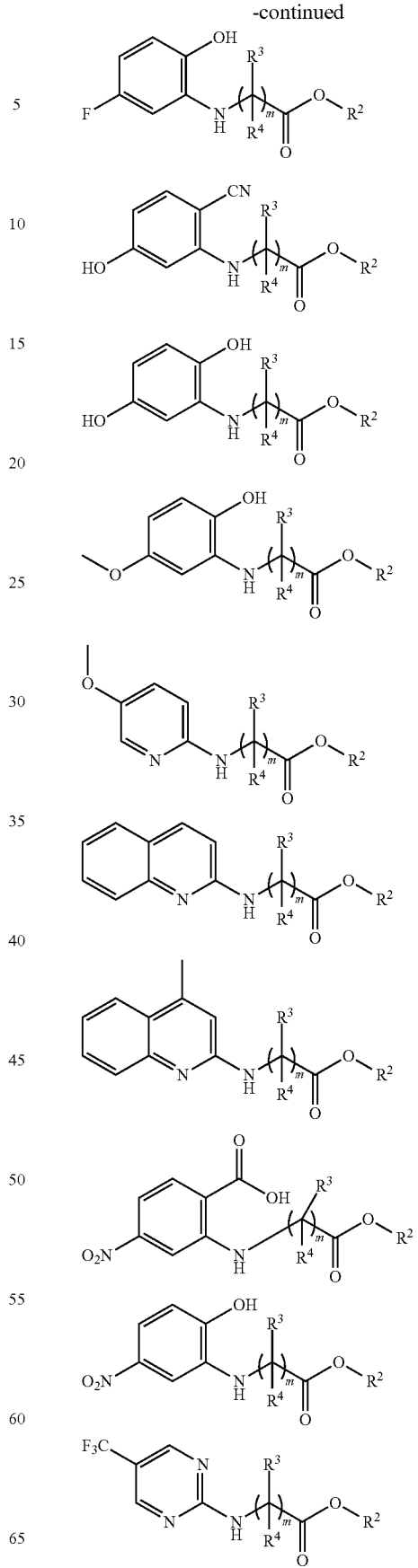

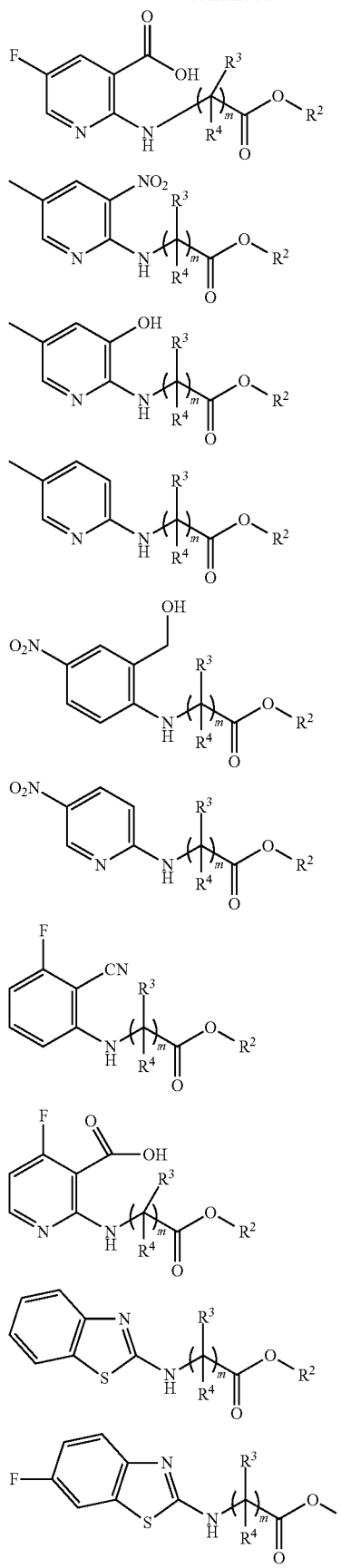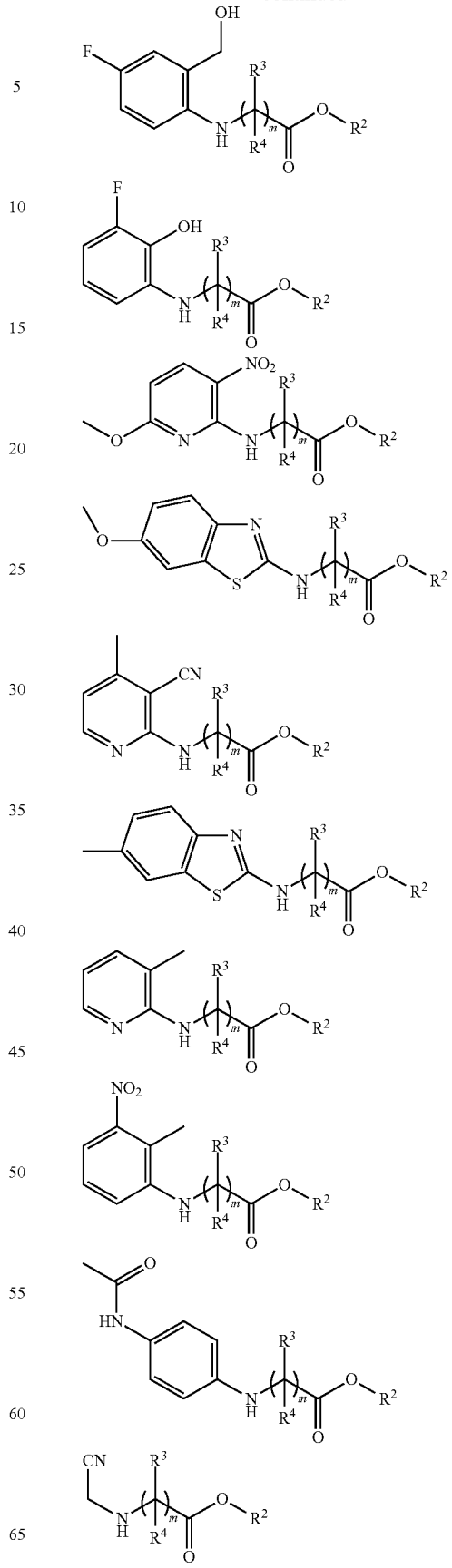

25
-continued
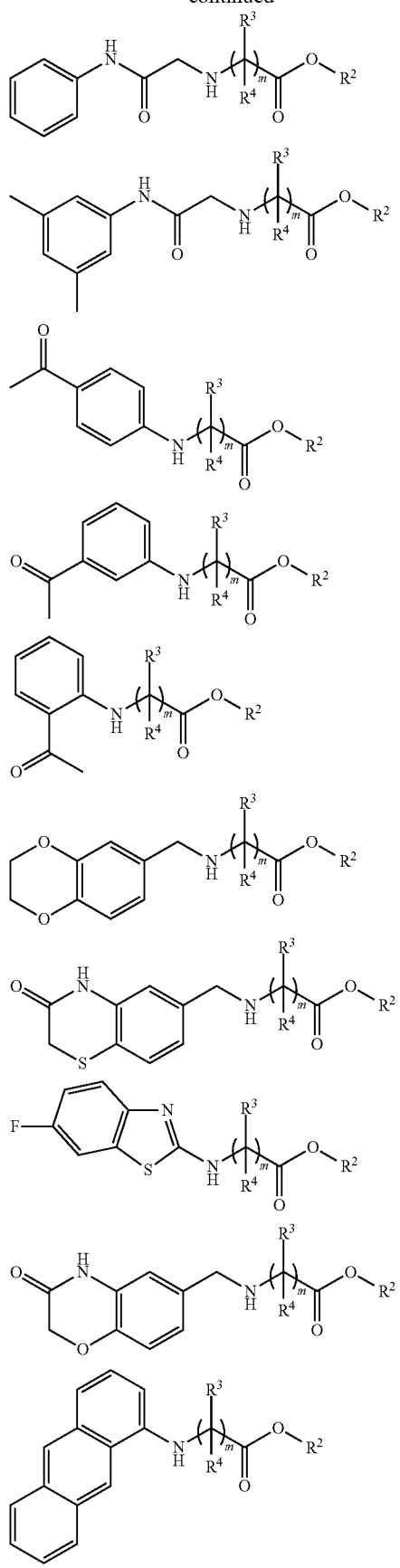
26
-continued
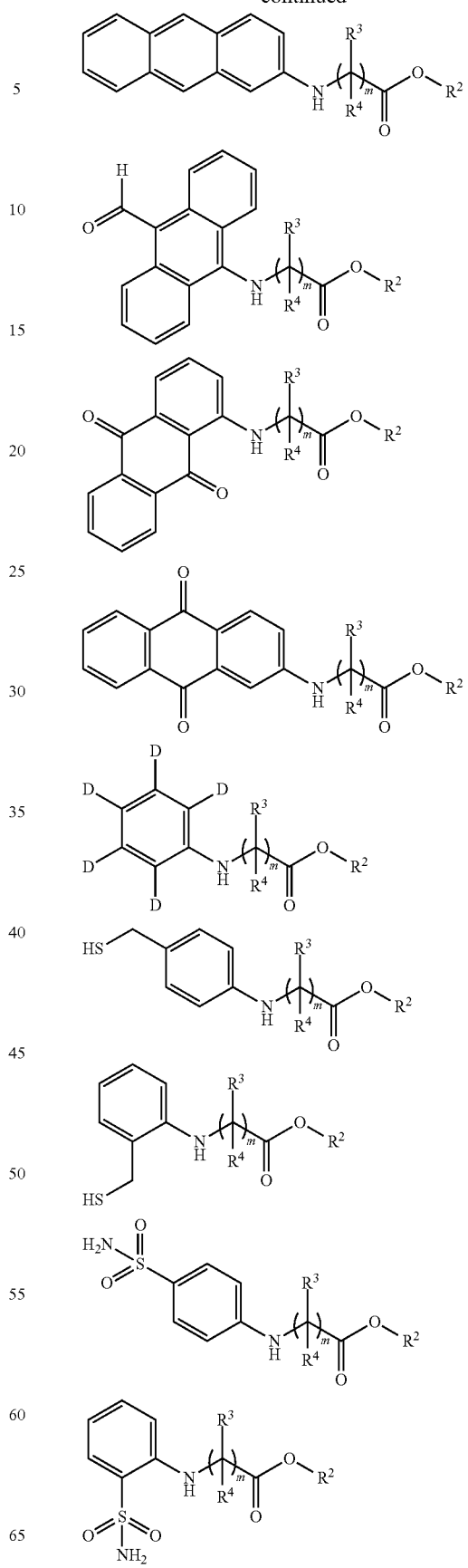

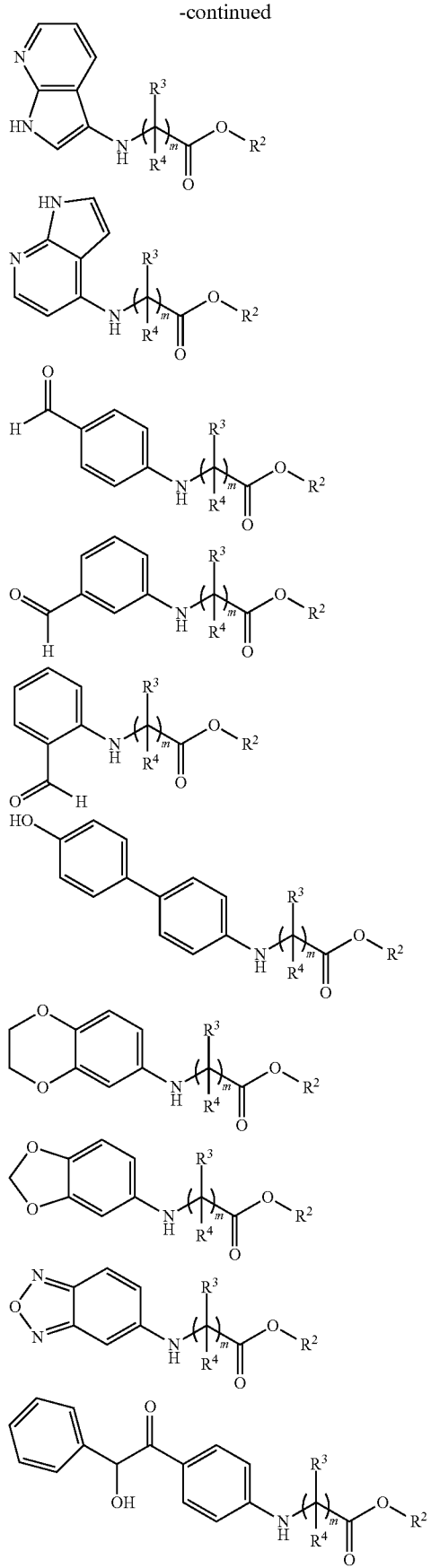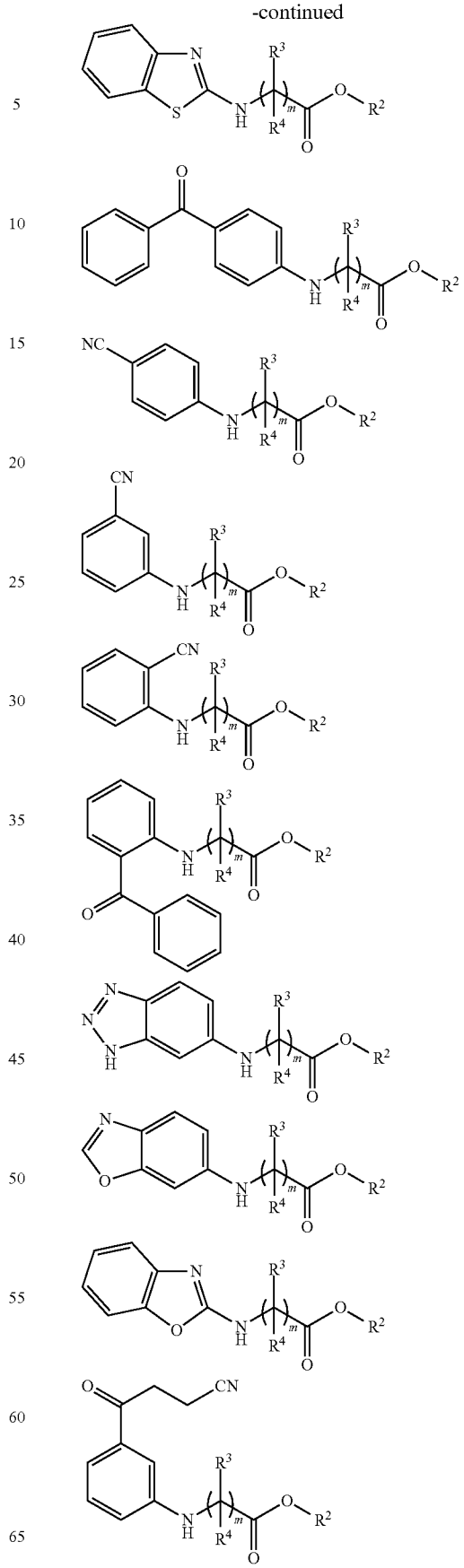

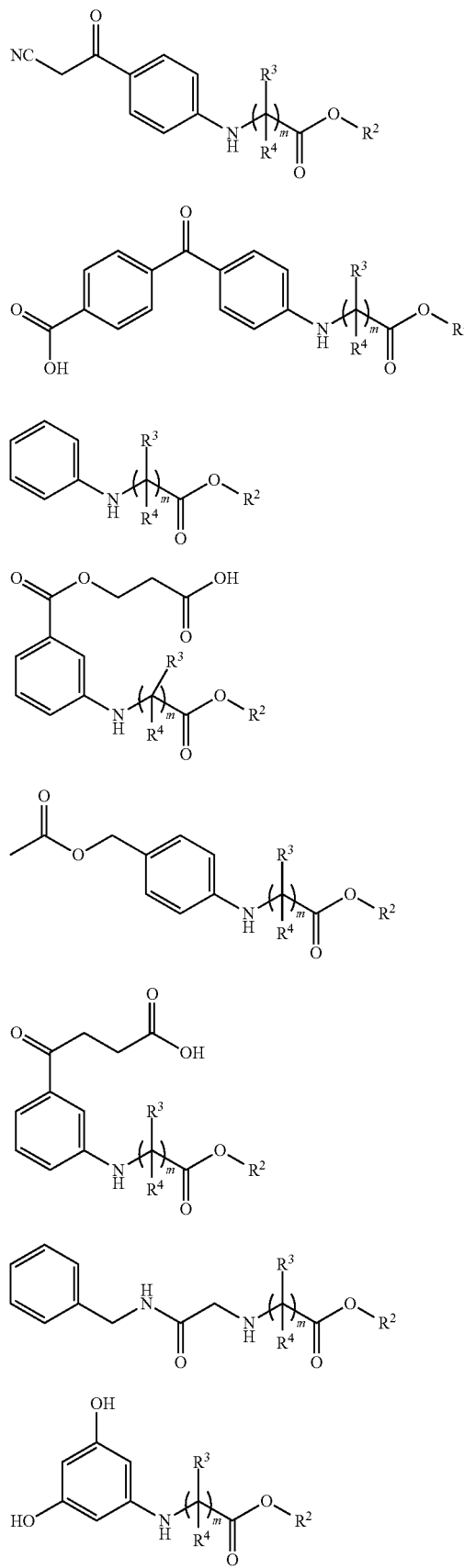
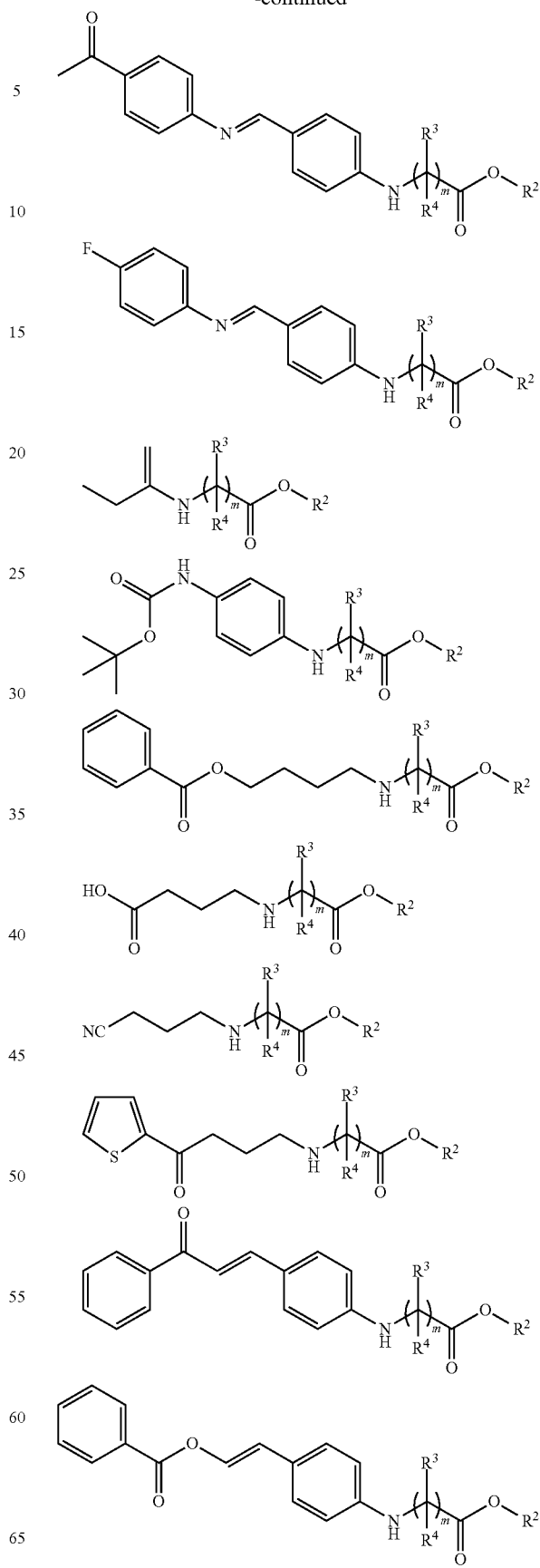

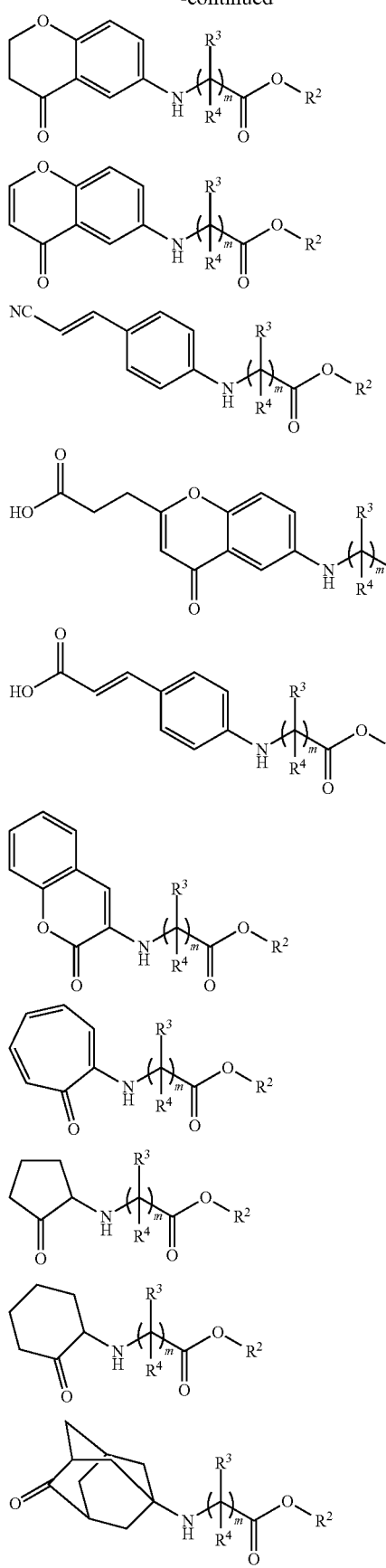
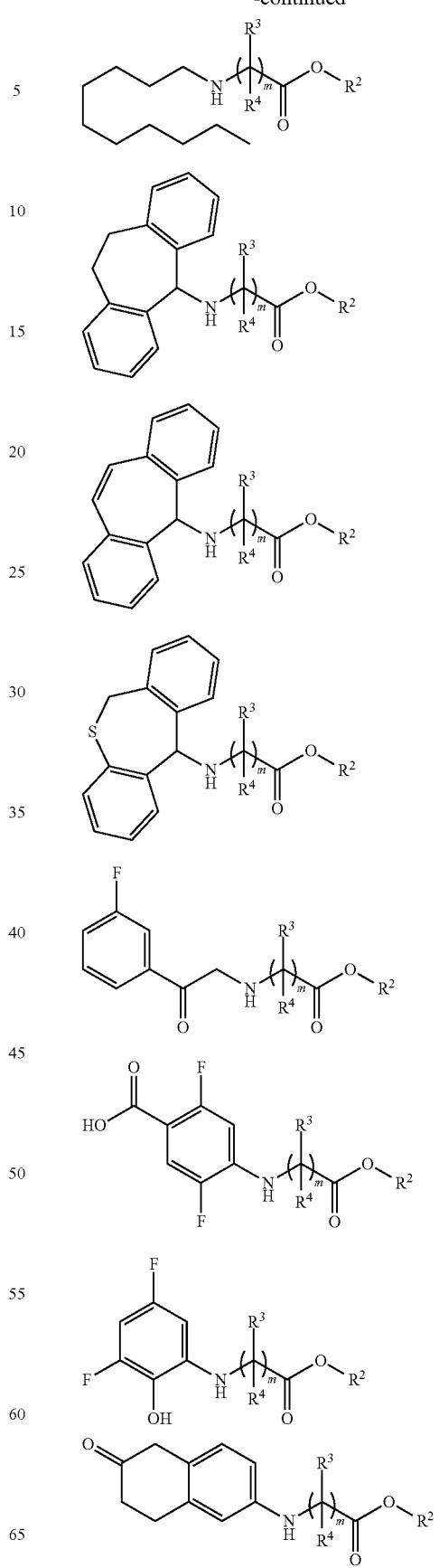

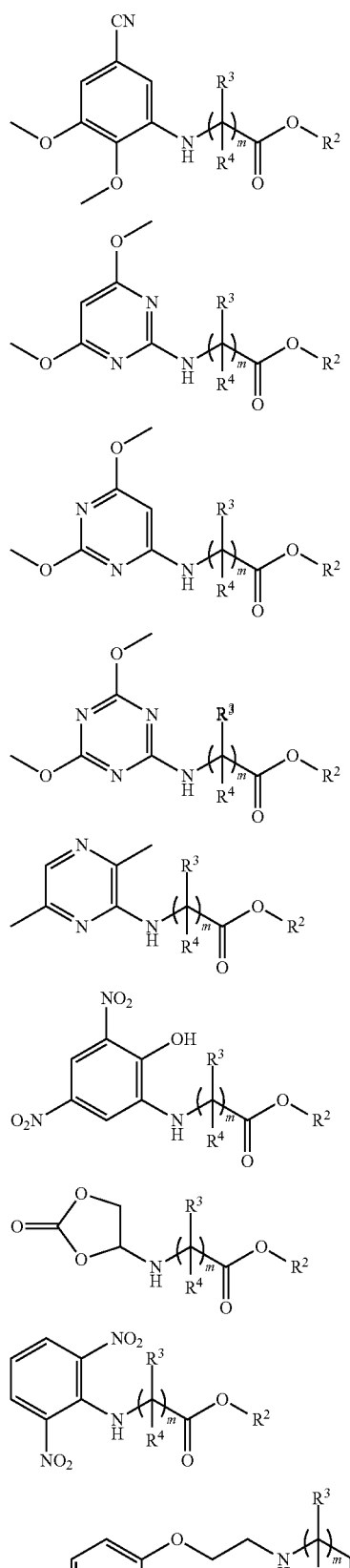
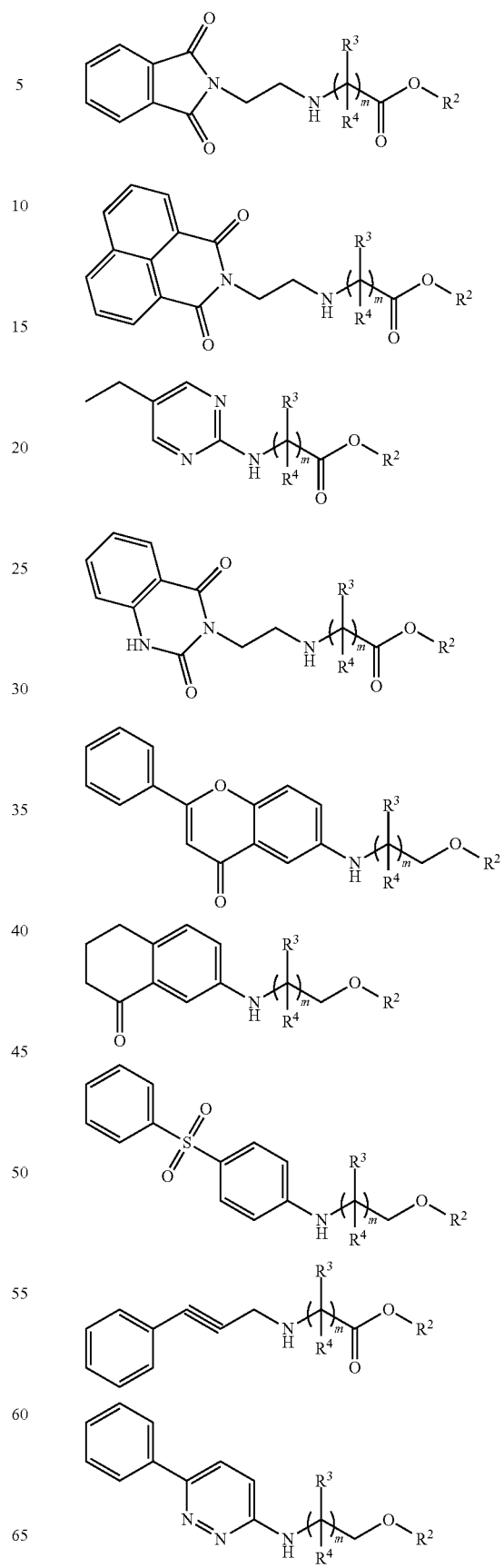

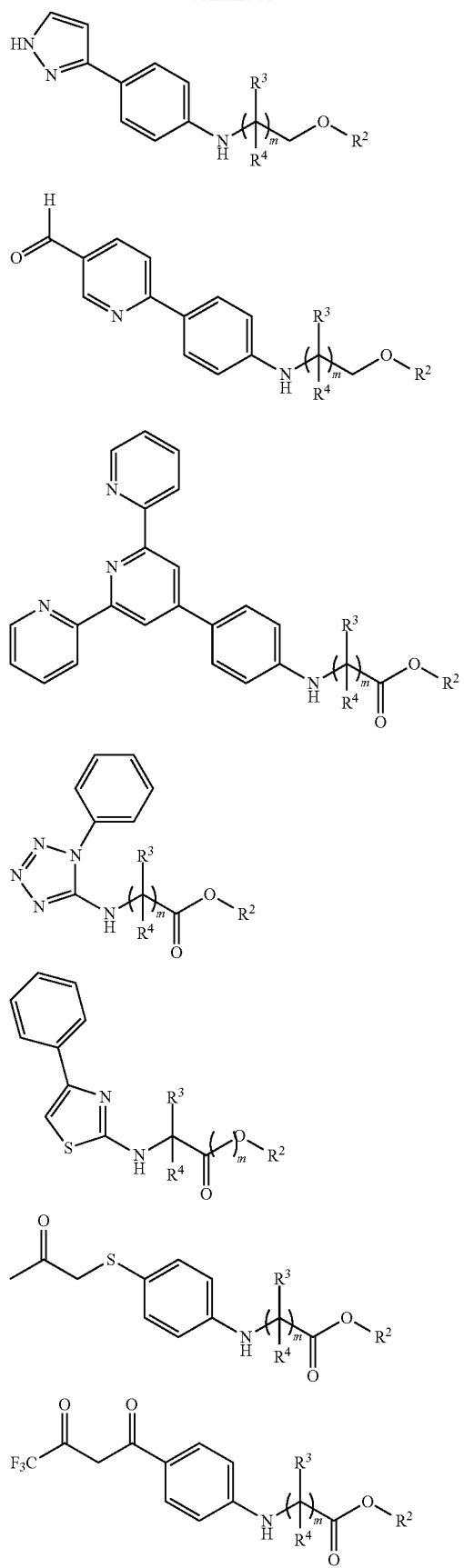
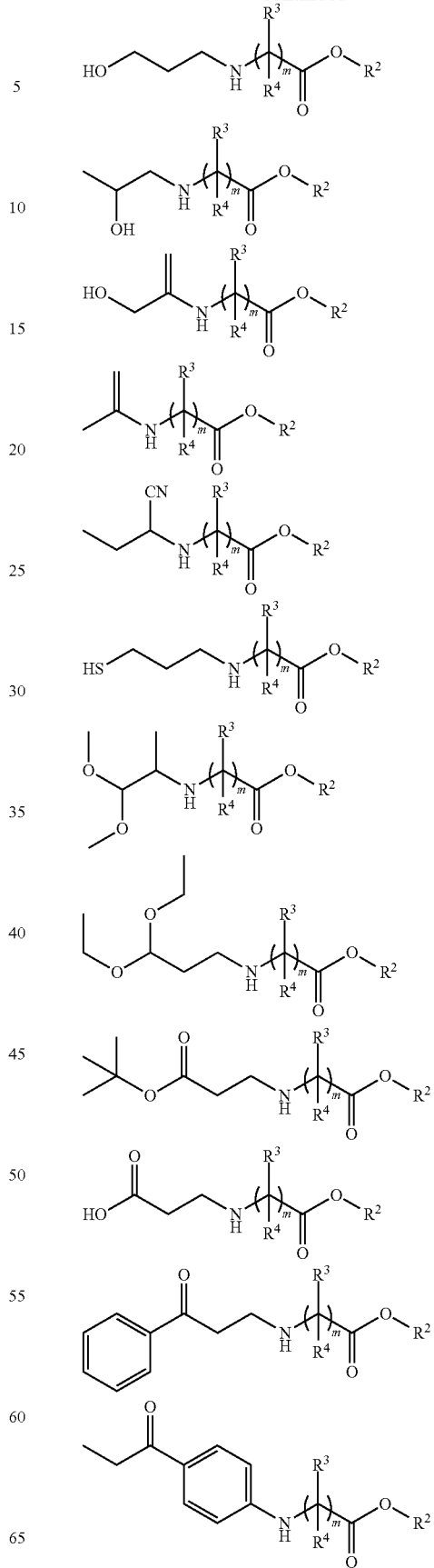

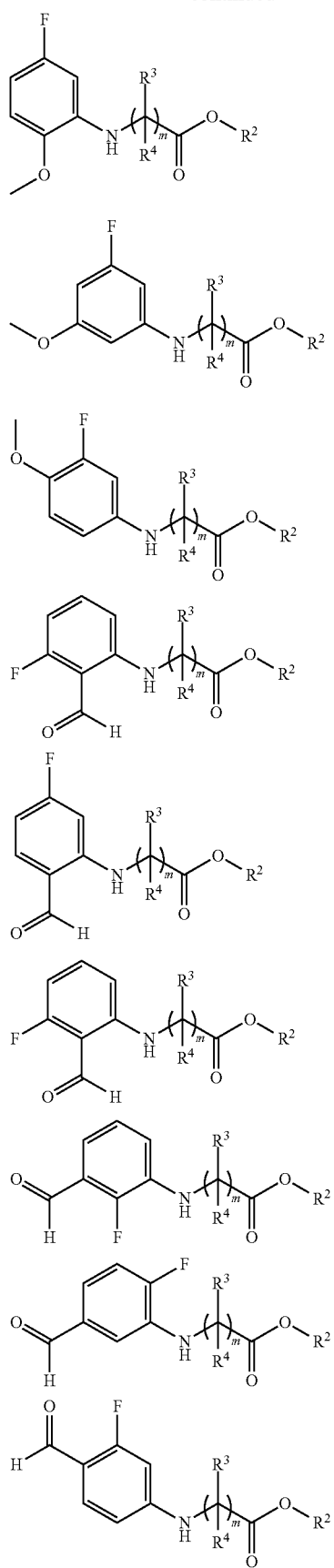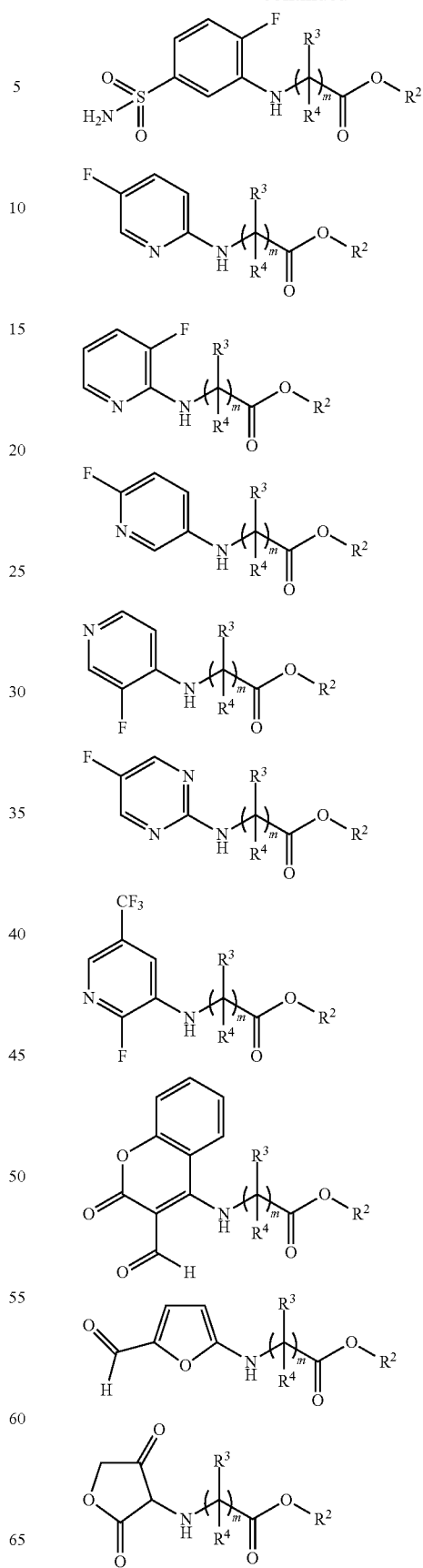

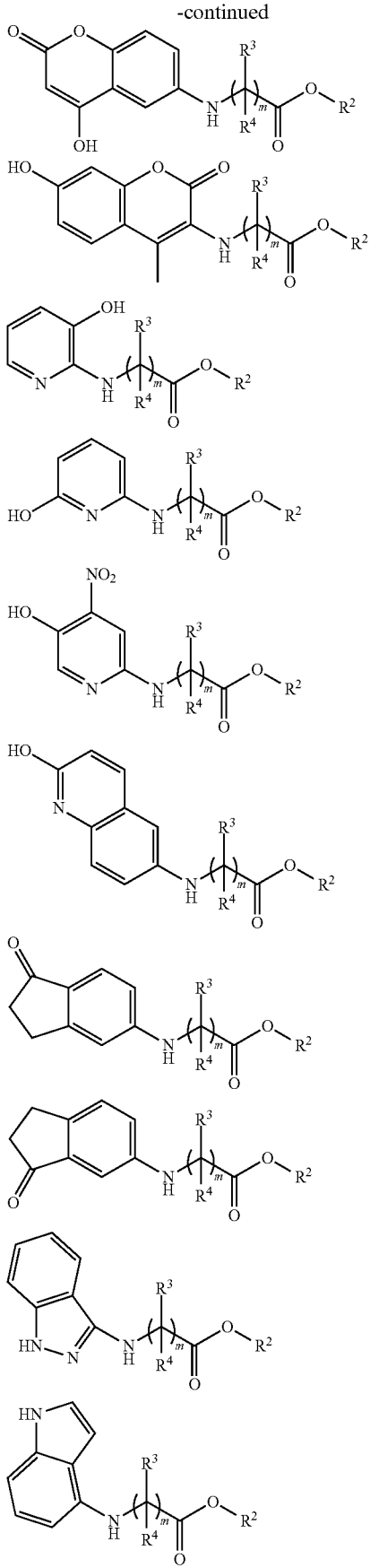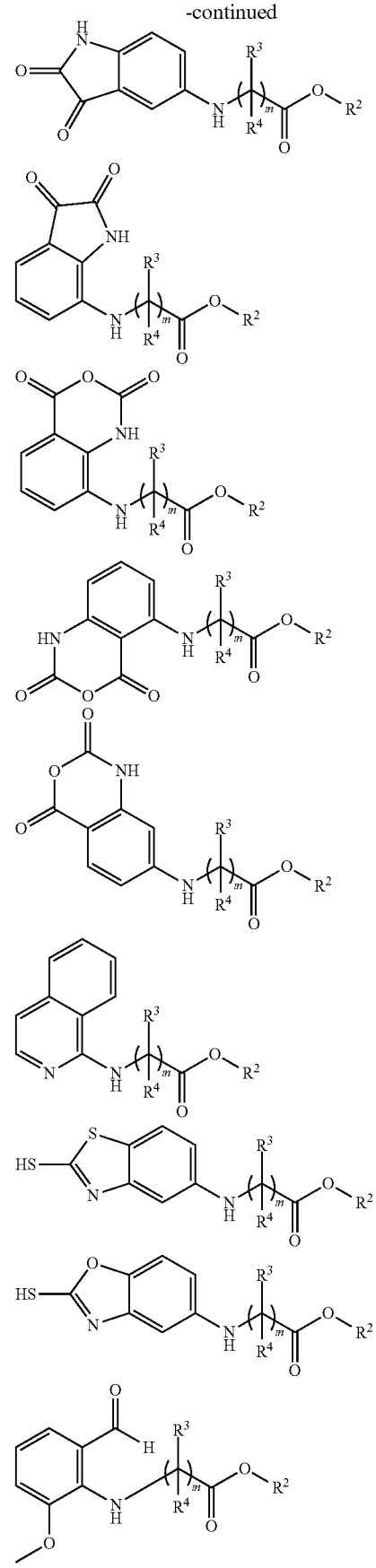

-continued
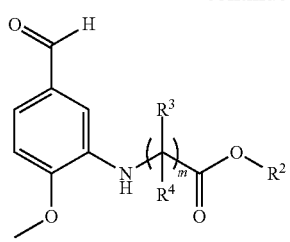
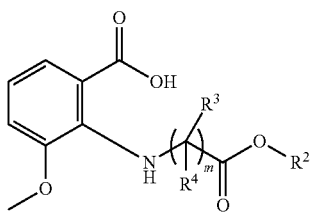
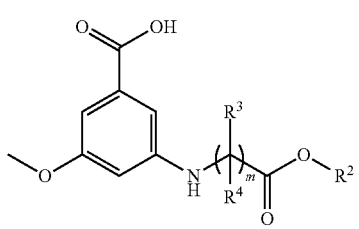
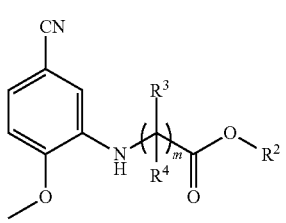
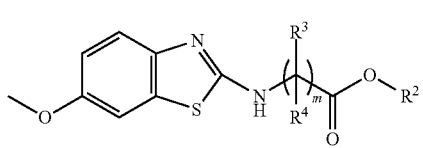
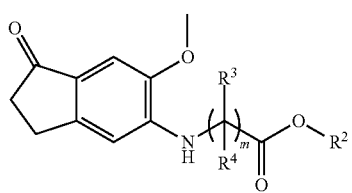
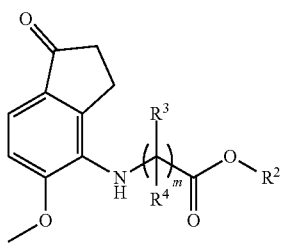
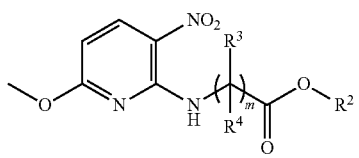
-continued
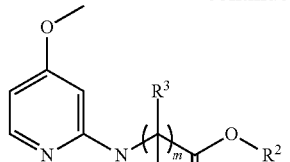
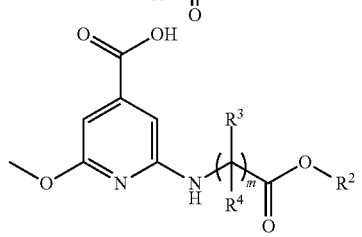
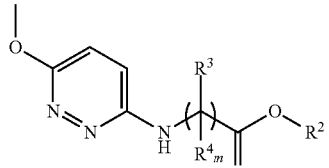
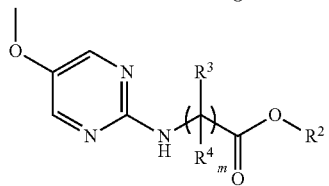
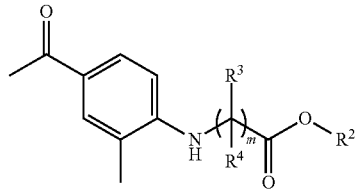
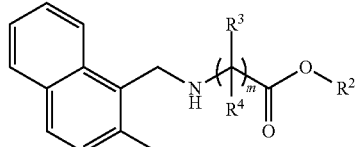
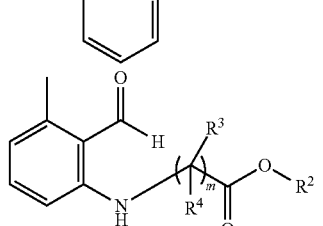
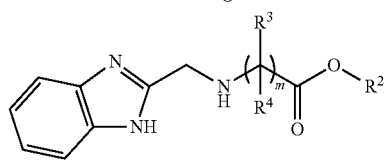
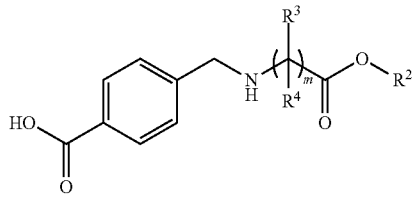

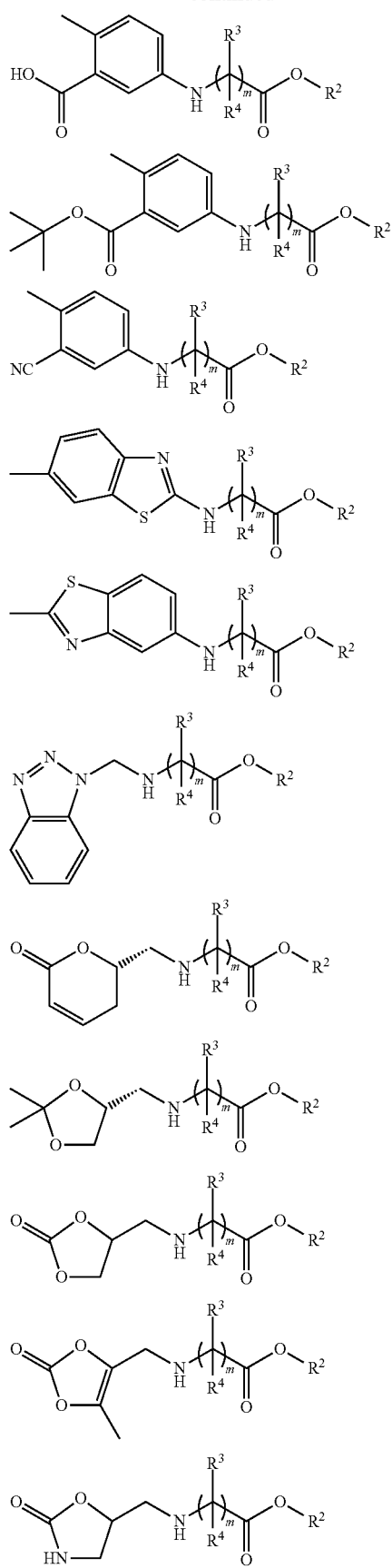
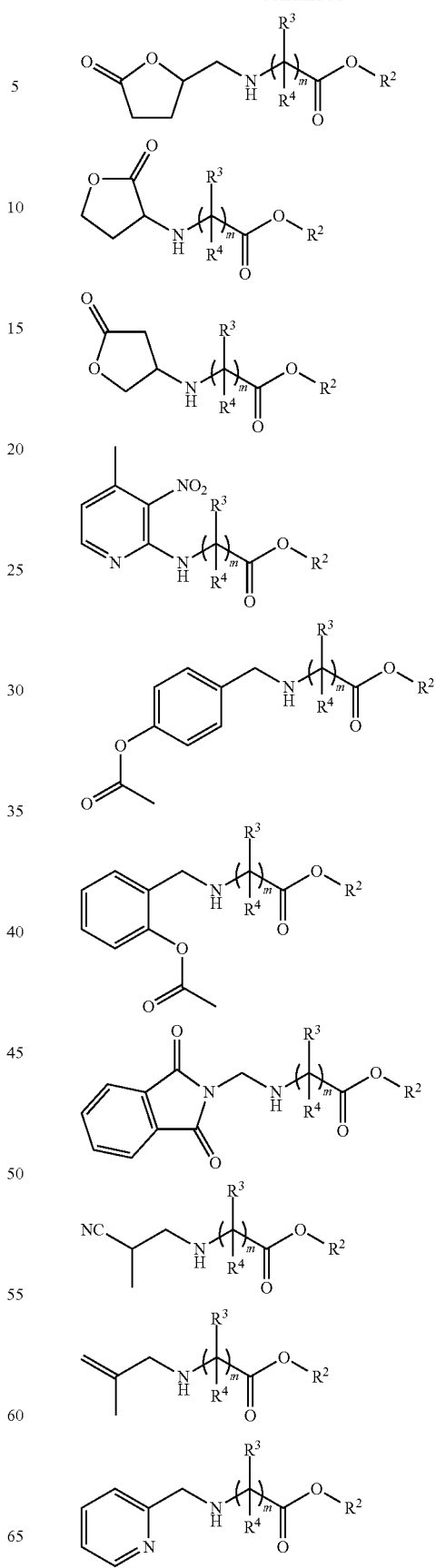

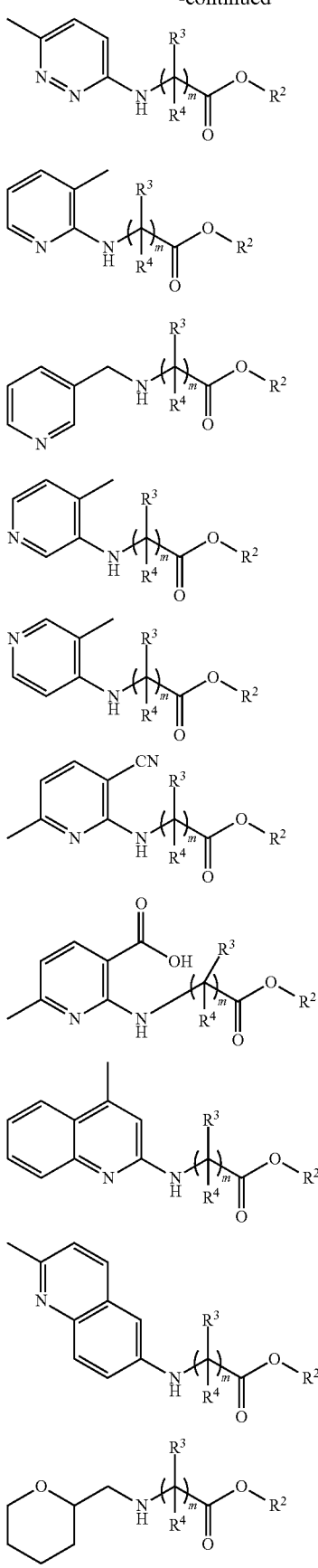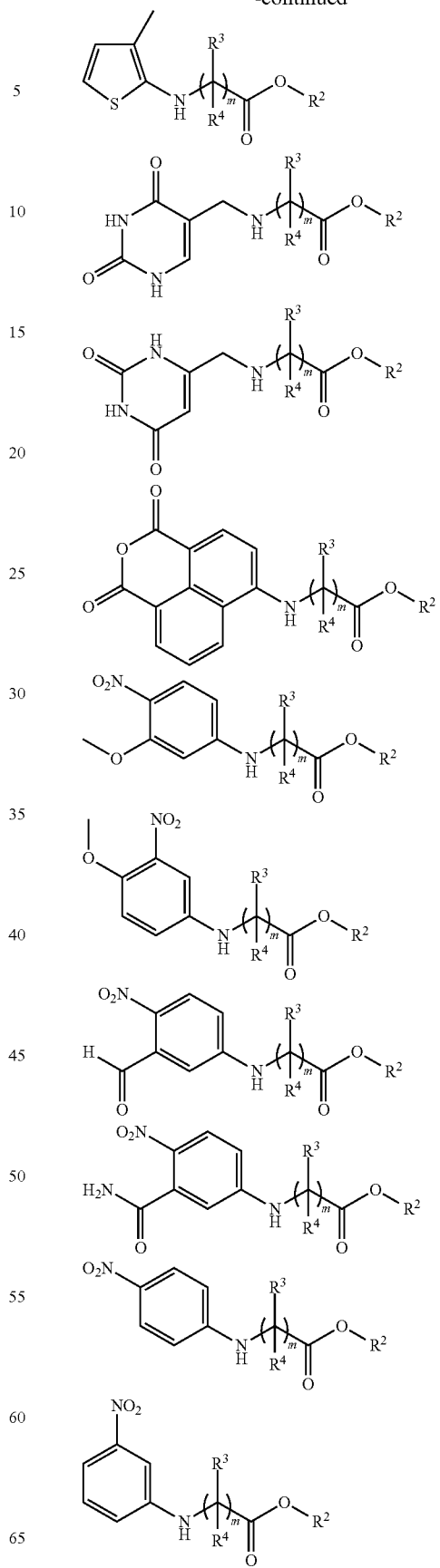

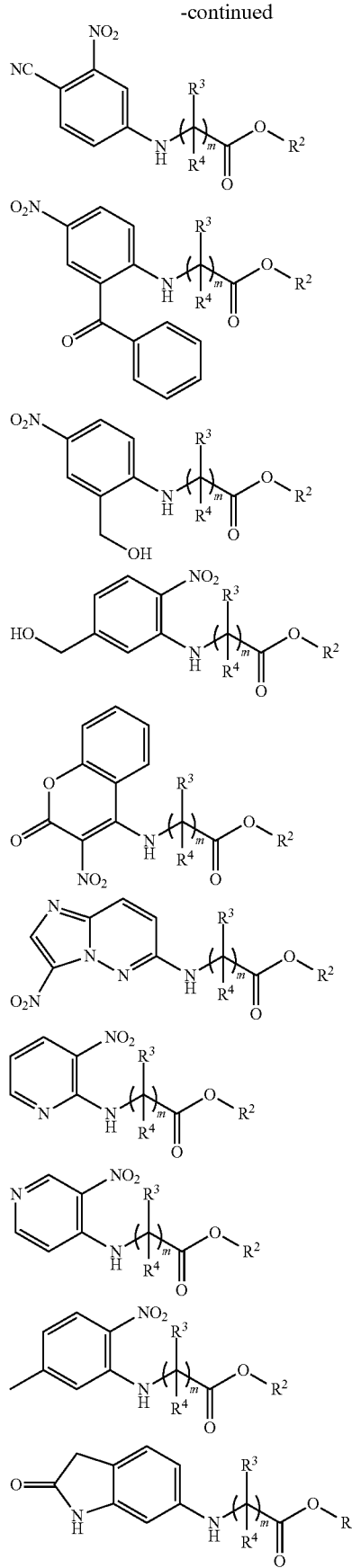
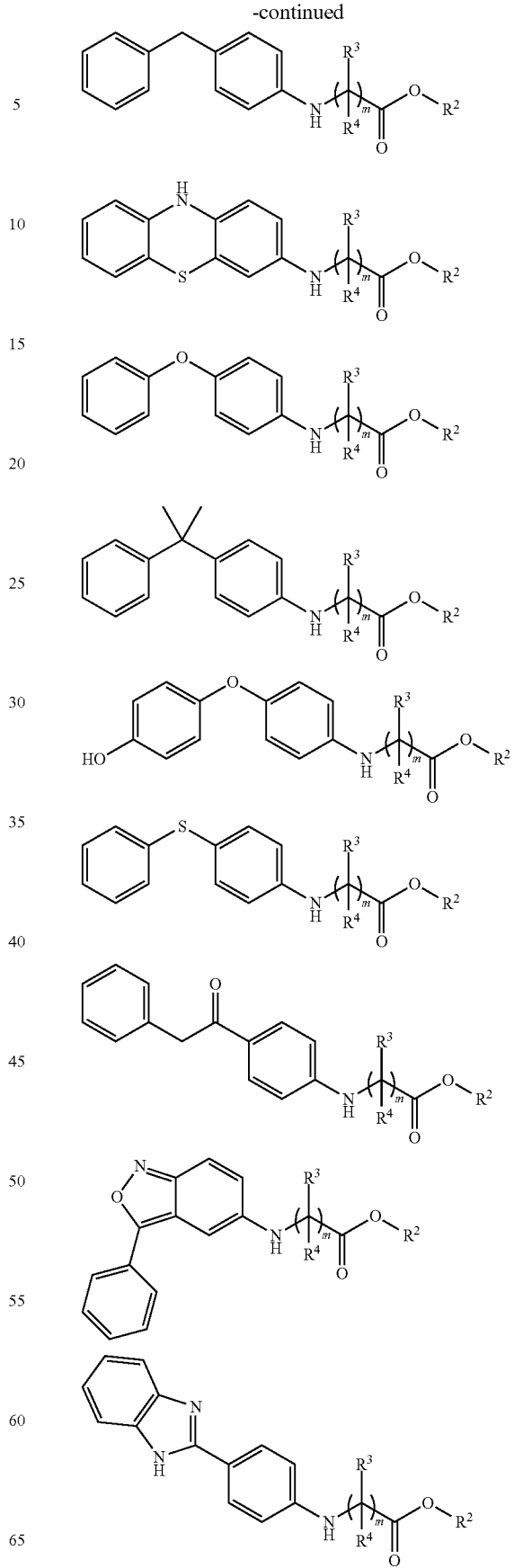

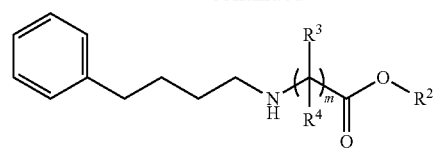
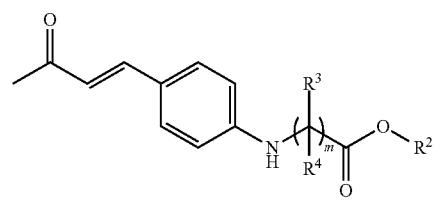
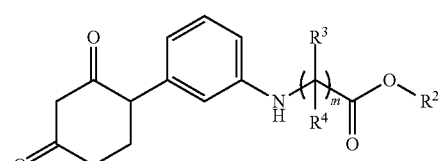
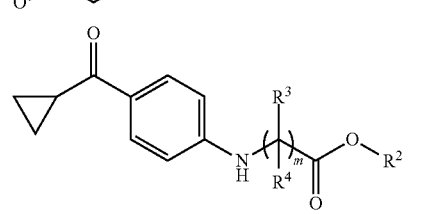
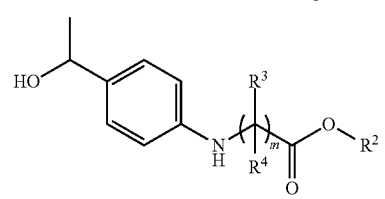
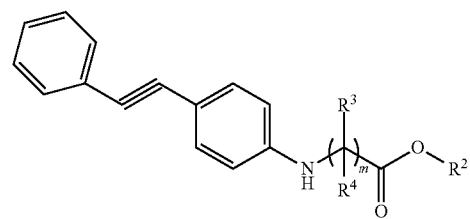
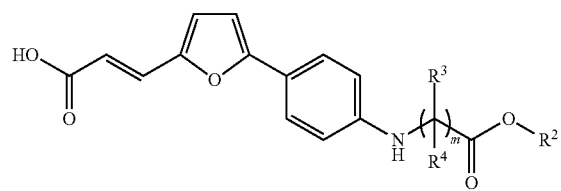
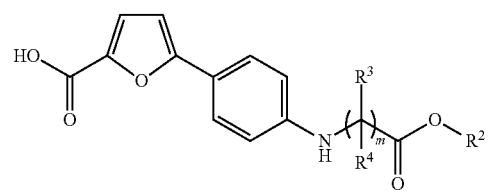
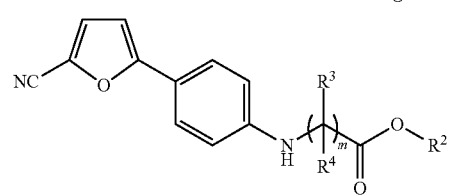
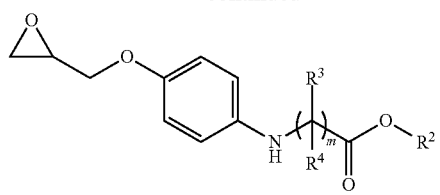
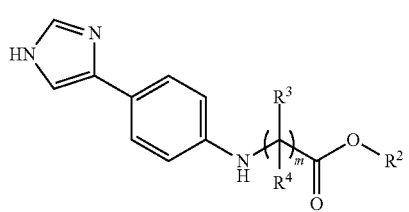
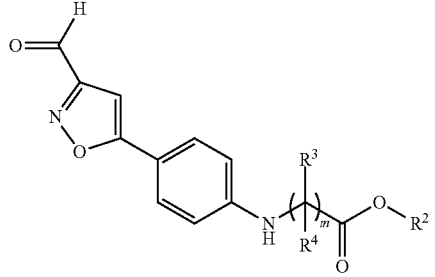
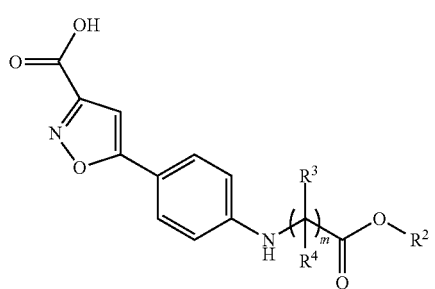
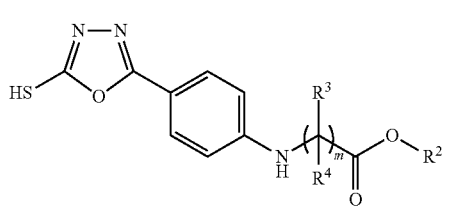
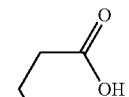
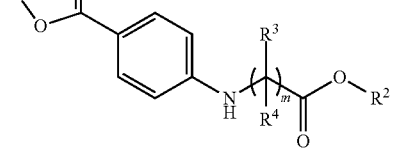
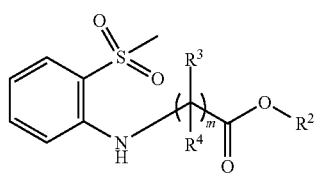

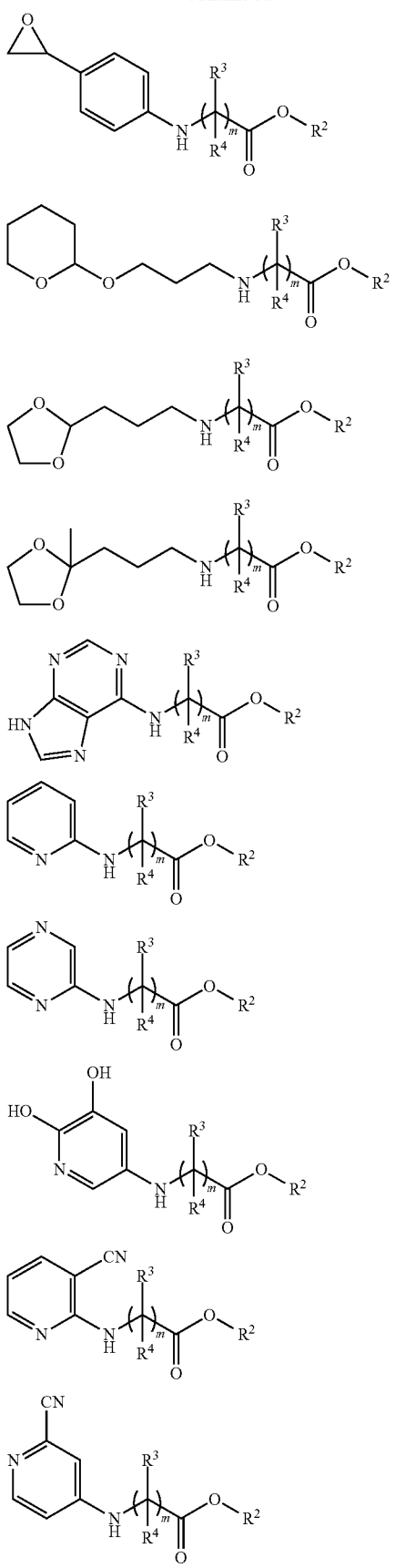
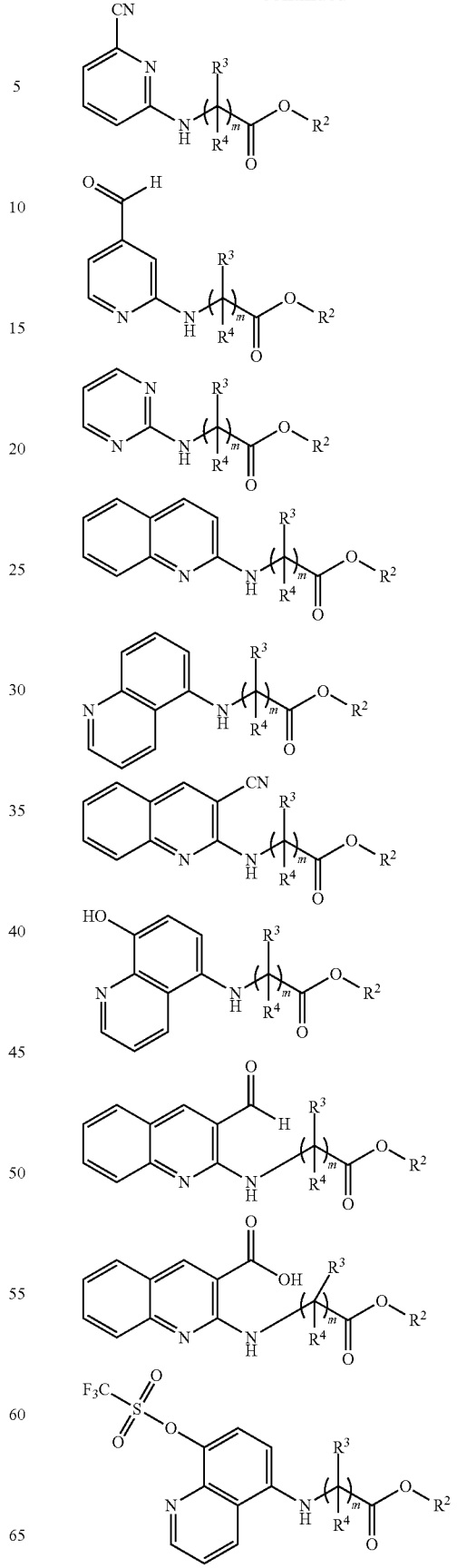

-continued
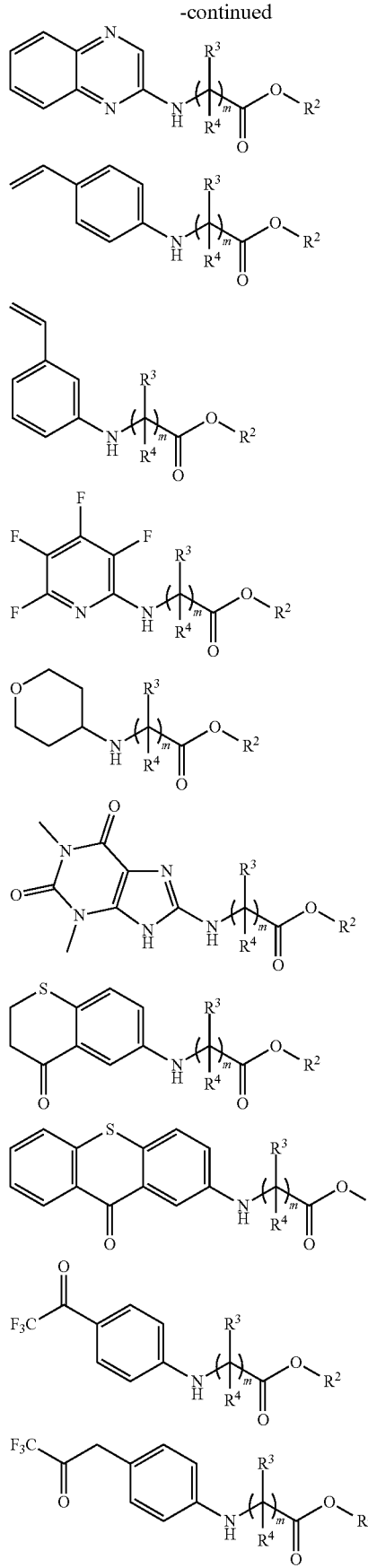
-continued
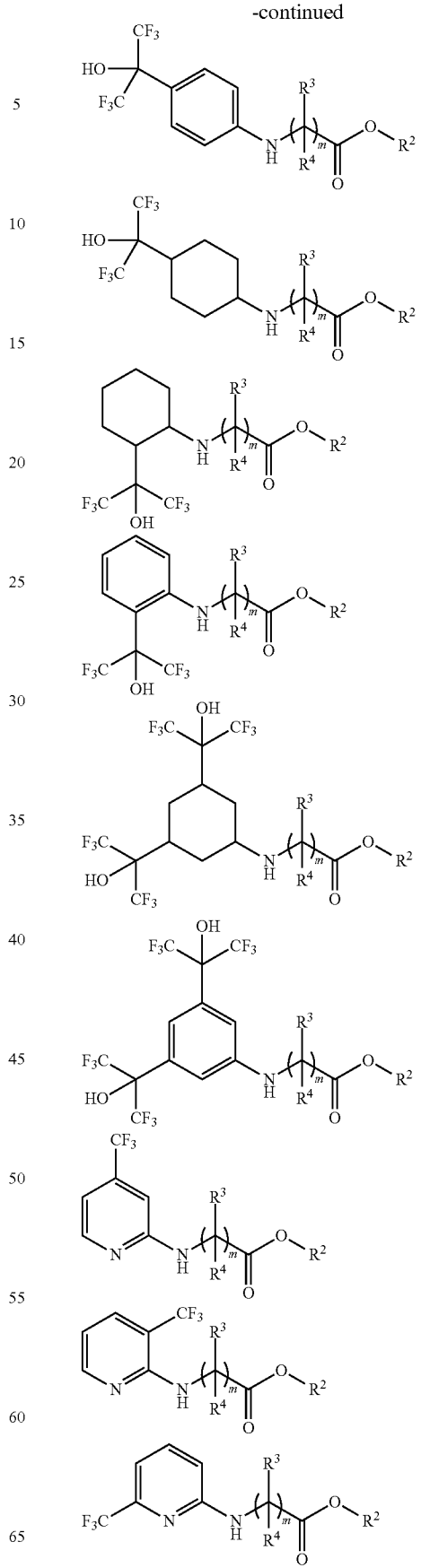

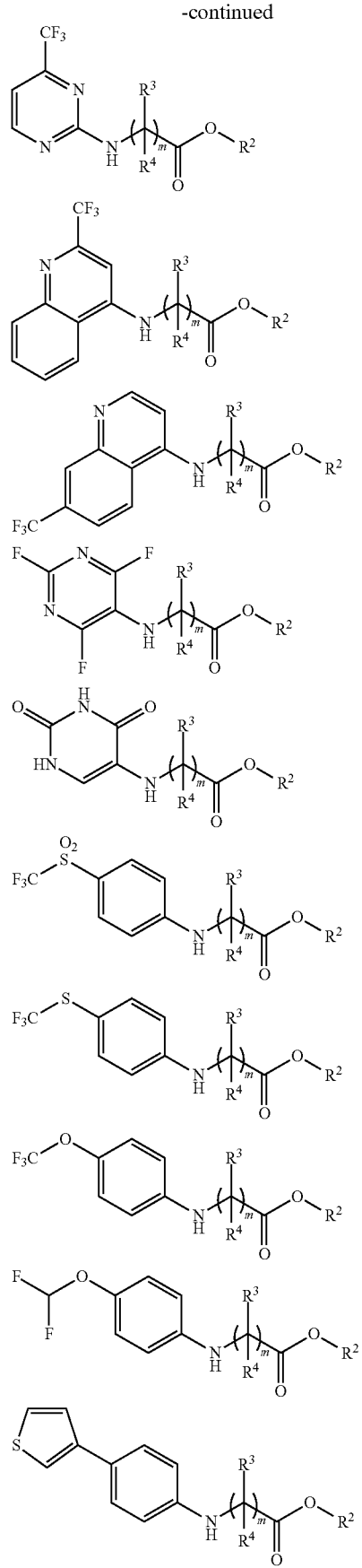
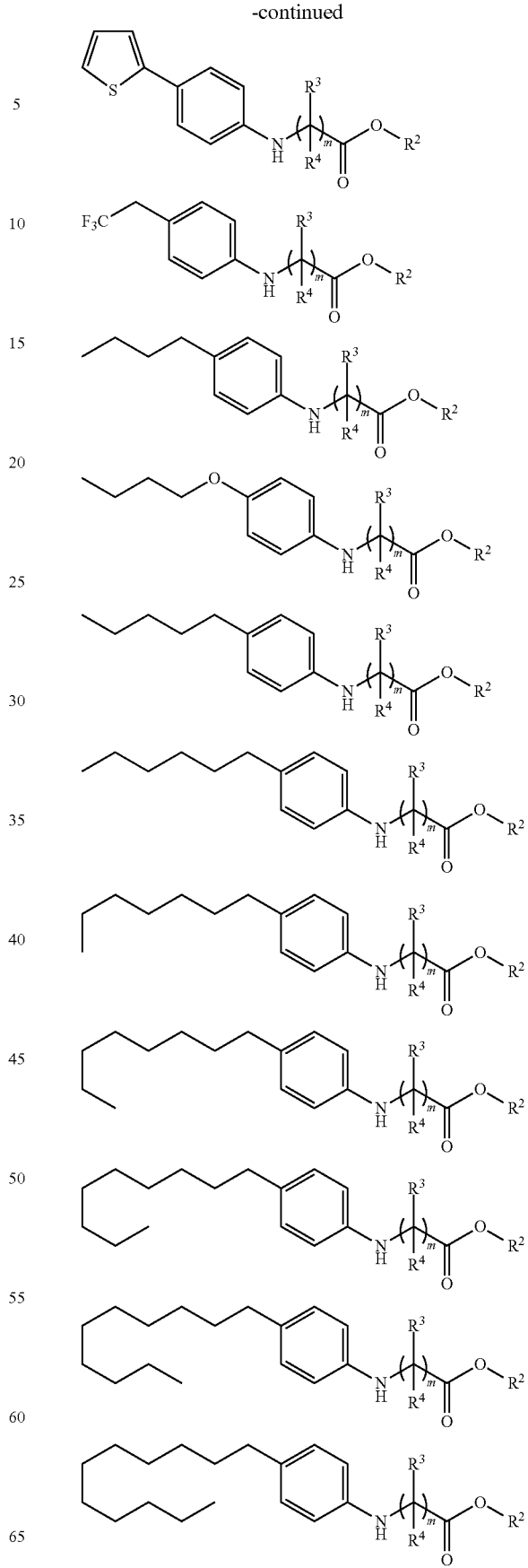

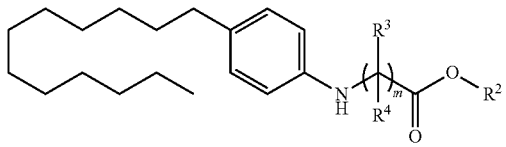
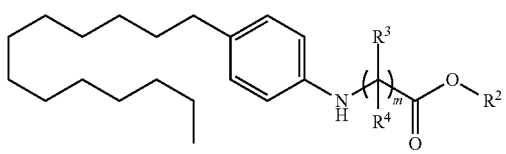
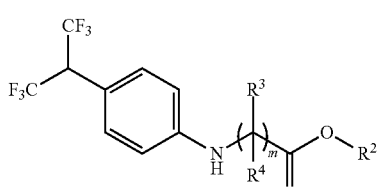
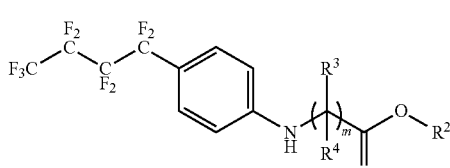
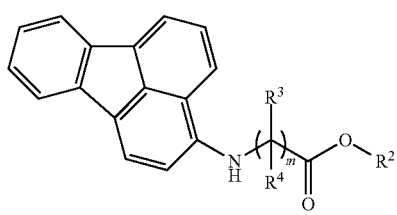
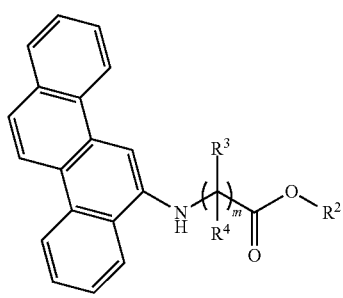
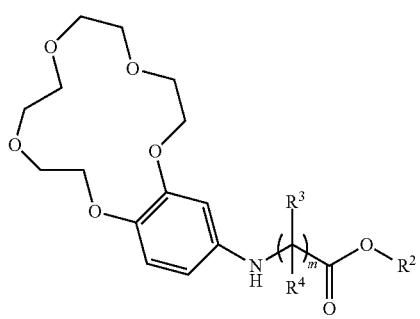

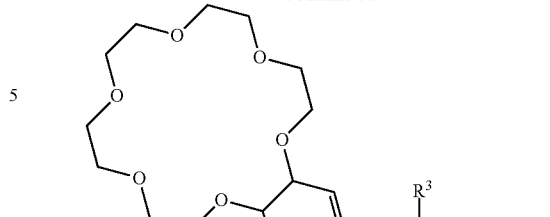
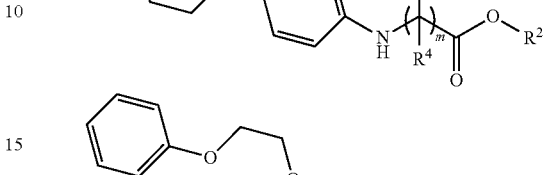
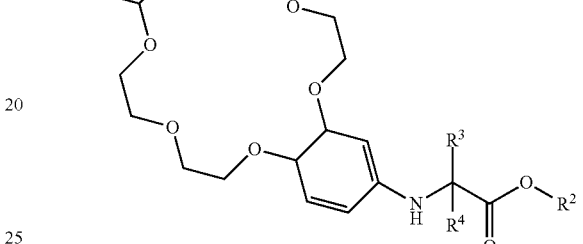

Herein $R^3$ and $R^4$ are as defined above, and D is heavy hydrogen. $R^2$ which is an acid labile group will be illustrated later in connection with the acid labile group in a photoresist base polymer.

The resist composition comprising the β-alanine, γ-aminobutyric acid or 5-aminovaleric acid derivative having an acid labile group-substituted carboxyl group may be either positive or negative, but should be a chemically amplified resist composition comprising an acid generator independent of whether it is positive or negative. The β-alanine, γ-aminobutyric acid or 5-aminovaleric acid derivative having an acid labile group-substituted carboxyl group acts in such a way that it may trap an acid to suppress acid diffusion in the unexposed region, while in the exposed region, it may form a β-alanine, γ-aminobutyric acid or 5-aminovaleric acid through elimination of the acid labile group with the aid of acid, and may also form a lactam through cyclization reaction with the aid of acid, leading to a lowering of basicity and a concomitant improvement in contrast. Accordingly, the β-alanine, γ-aminobutyric acid or 5-aminovaleric acid derivative is advantageously applied to a chemically amplified resist composition utilizing an acid as a catalyst.

The chemically amplified resist composition of the invention comprises the basic compound of formula (1), a base polymer, and an acid generator, both to be described below. From the standpoints of sensitivity and acid diffusion control, the basic compound of formula (1) is preferably present in the composition in an amount of 0.001 to 20 parts by weight, more preferably 0.01 to 10 parts by weight per 100 parts by weight of the base polymer.

In the embodiment wherein chemically amplified resist compositions are positive, the base polymer comprises recurring units having an acid labile group. Suitable recurring units having an acid labile group include recurring units of (meth)acrylate, styrenecarboxylic acid and vinylnaphthalenecarboxylic acid having an acid labile group substituted thereon, as represented by unit (a1) in the general formula (2), and recurring units of hydroxystyrene having an acid labile group substituted thereon, as represented by unit (a2) in the general formula (2).

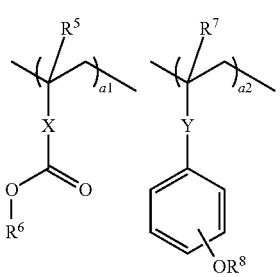
(2)

Herein, $R^5$ and $R^7$ which may be the same or different is hydrogen or methyl. X is a single bond, ester group, linking group of 1 to 12 carbon atoms having a lactone ring, phenylene group, or naphthylene group. Y is a single bond or ester group. $R^6$ and $R^8$ each are an acid labile group.

The recurring units (a1) having an acid labile group are preferably derived from (meth)acrylic acid, styrenecarboxylic acid and vinylnaphthalenecarboxylic acid by substituting an acid labile group for the hydrogen atom of carboxyl group. Illustrative, non-limiting, examples of recurring units (a1) are given below.

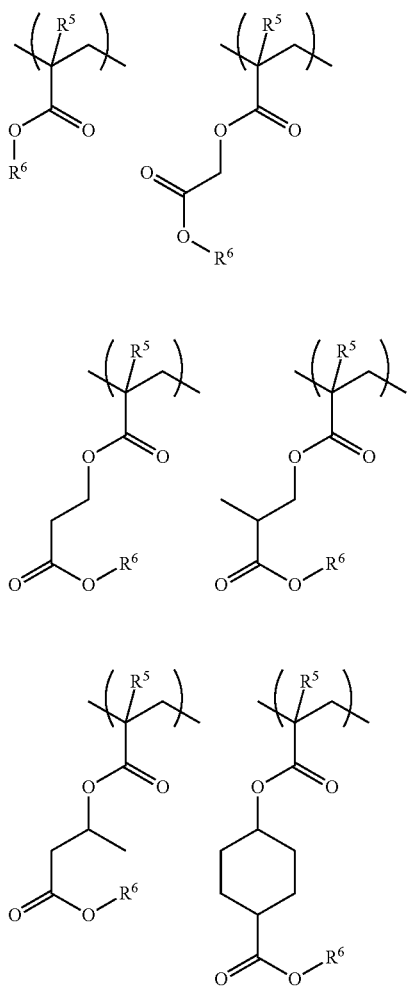

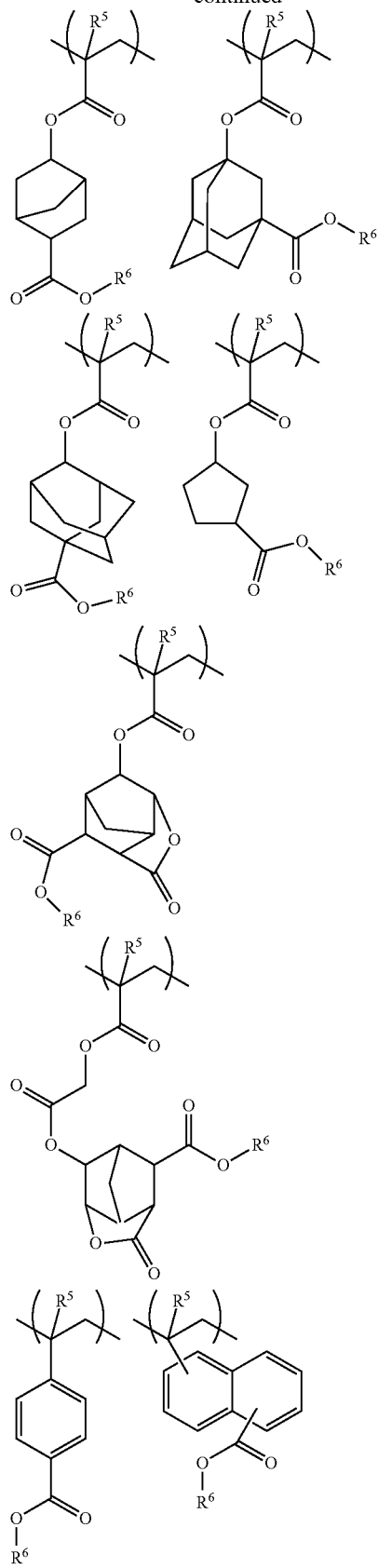

Herein $R^5$ and $R^6$ are as defined above.

The acid labile groups represented by $R^1$ and $R^2$ in formula (1), i.e., basic compound and $R^6$ and $R^8$ in the recurring units (a1) and (a2) may be selected from a variety of such groups. The acid labile groups may be the same or different and preferably include groups of the following formulae (A-1) to (A-3).

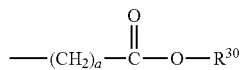
(A-1)

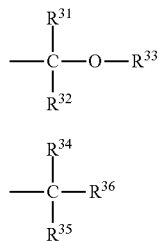
(A-2)

(A-3)

In formula (A-1), $R^{30}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (A-3). Exemplary tertiary alkyl groups are tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter "a" is an integer of 0 to 6.

In formula (A-2), $R^{31}$ and $R^{32}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, and n-octyl. $R^{33}$ is a monovalent hydrocarbon group of 1 to 18 carbon atoms, preferably 1 to 10 carbon atoms, which may contain a heteroatom such as oxygen, examples of which include straight, branched or cyclic alkyl groups and substituted forms of such alkyl groups in which some hydrogen atoms are replaced by hydroxyl, alkoxy, oxo, amino, alkylamino or the like. Illustrative examples of the substituted alkyl groups are shown below.

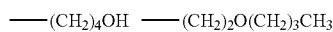
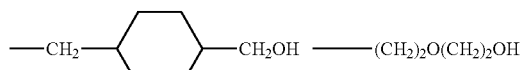
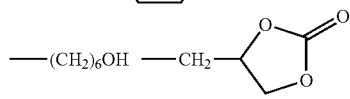

A pair of $R^{31}$ and $R^{32}$, $R^{31}$ and $R^{33}$, or $R^{32}$ and $R^{33}$ may bond together to form a ring with the carbon and oxygen atoms to which they are attached. Each of $R^{31}$, $R^{32}$ and $R^{33}$ is a straight or branched alkylene group of 1 to 18 carbon atoms, preferably 1 to 10 carbon atoms when they form a ring, while the ring preferably has 3 to 10 carbon atoms, more preferably 4 to 10 carbon atoms.

Examples of the acid labile groups of formula (A-1) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Also included are substituent groups having the formulae (A-1)-1 to (A-1)-10.

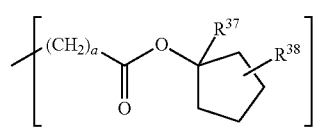
(A-1)-1

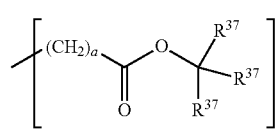
(A-1)-2

(A-1)-3

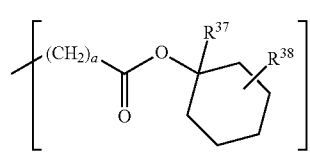
(A-1)-4

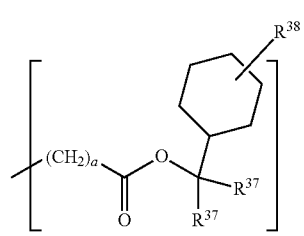
(A-1)-5

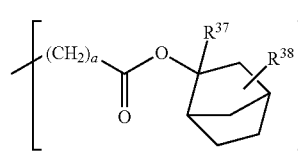
(A-1)-6

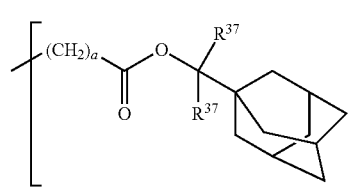
(A-1)-7

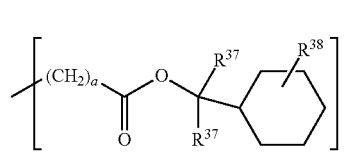
(A-1)-8

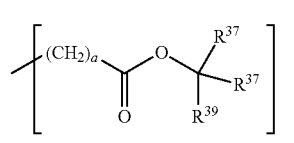

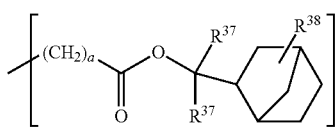
(A-1)-9

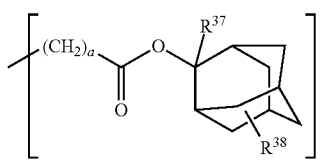
(A-1)-10

Herein $R^{37}$ is each independently a straight, branched or cyclic $C_1$-$C_{10}$ alkyl group or $C_6$-$C_{20}$ aryl group, $R^{38}$ is hydrogen or a straight, branched or cyclic $C_1$-$C_{10}$ alkyl group, $R^{39}$ is each independently a straight, branched or cyclic $C_2$-$C_{10}$ alkyl group or $C_6$-$C_{20}$ aryl group, and "a" is an integer of 0 to 6.

Of the acid labile groups of formula (A-2), the straight and branched ones are exemplified by the following groups having formulae (A-2)-1 to (A-2)-72.

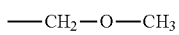
(A-2)-1

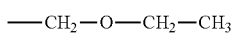
(A-2)-2

(A-2)-3

(A-2)-4

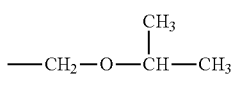
(A-2)-5

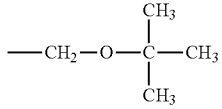
(A-2)-6

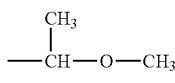
(A-2)-7

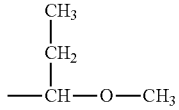
(A-2)-8

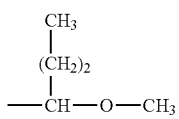
(A-2)-9

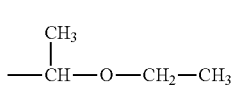
(A-2)-10

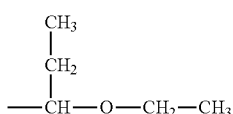
(A-2)-11

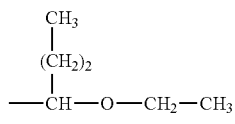
(A-2)-12

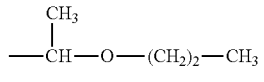
(A-2)-13

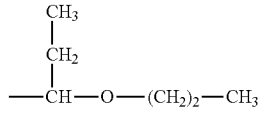
(A-2)-14

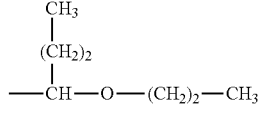
(A-2)-15

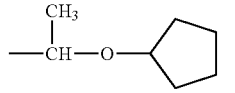
(A-2)-16

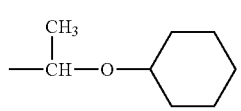
(A-2)-17

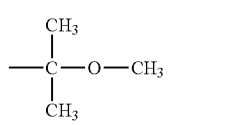
(A-2)-18

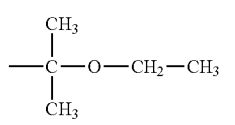
(A-2)-19

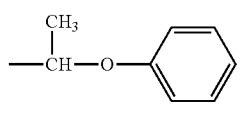
(A-2)-20

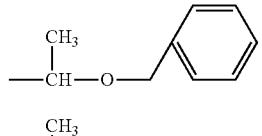
(A-2)-21

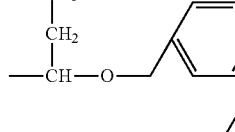
(A-2)-22

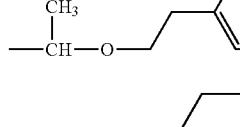
(A-2)-23

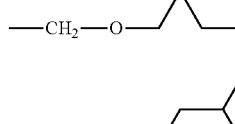
(A-2)-24

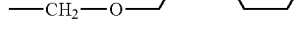
(A-2)-25

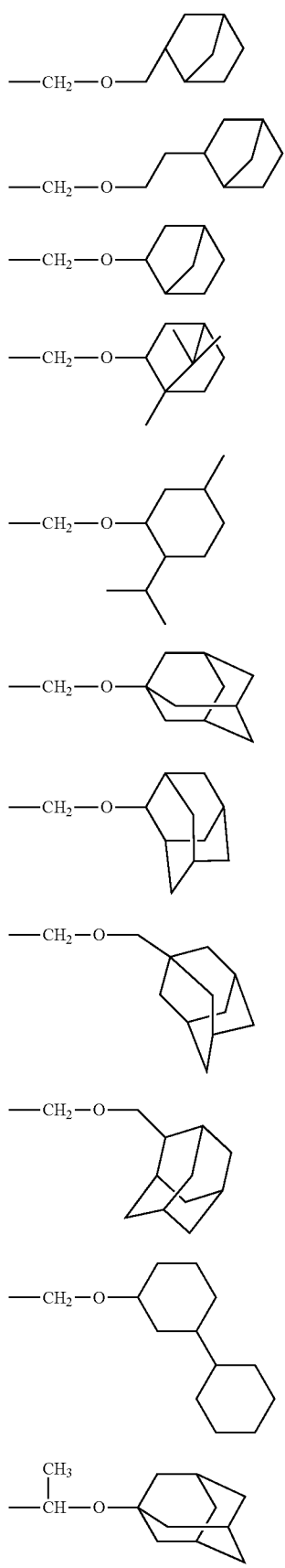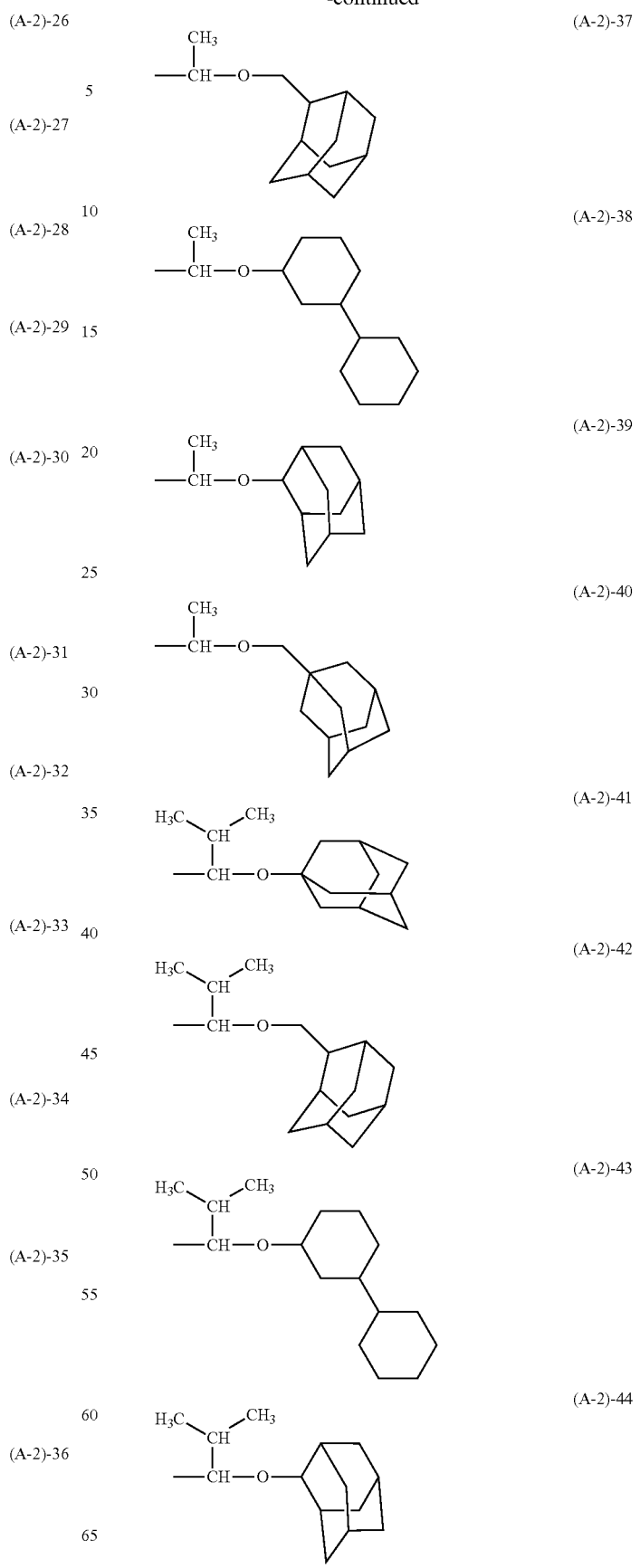

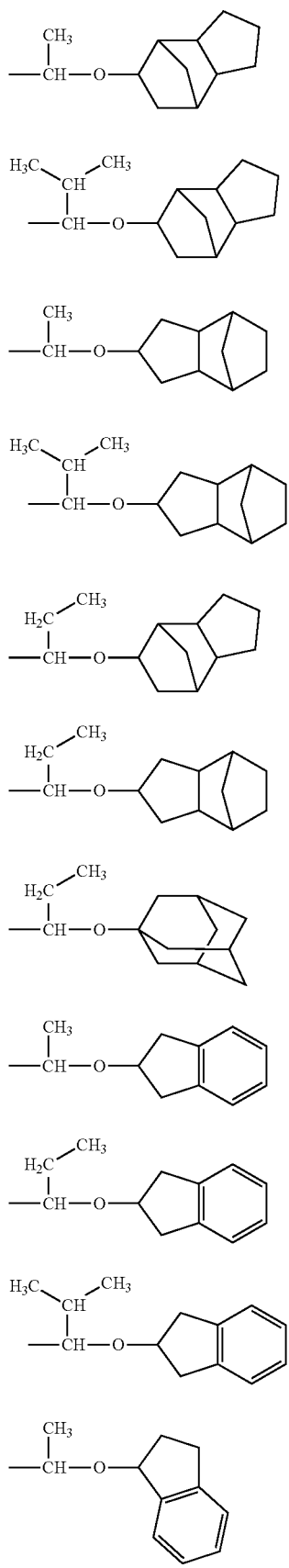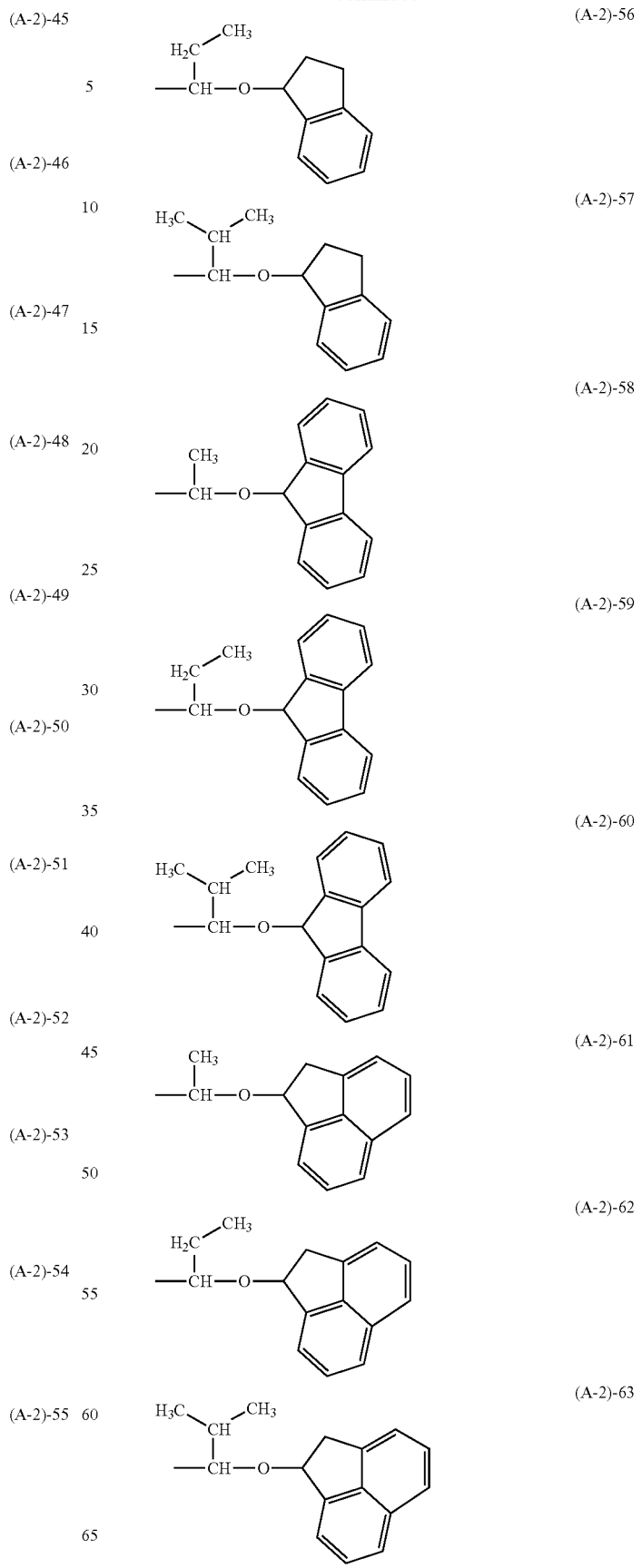

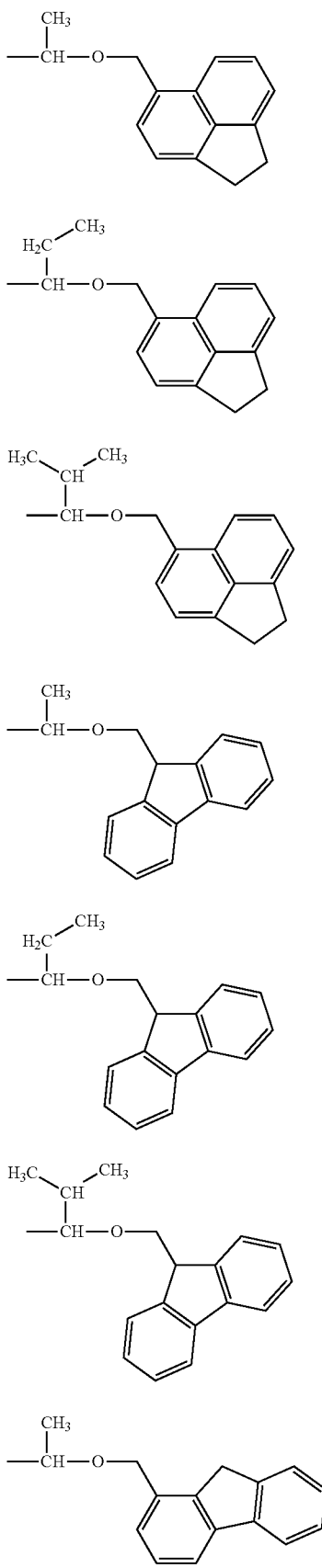
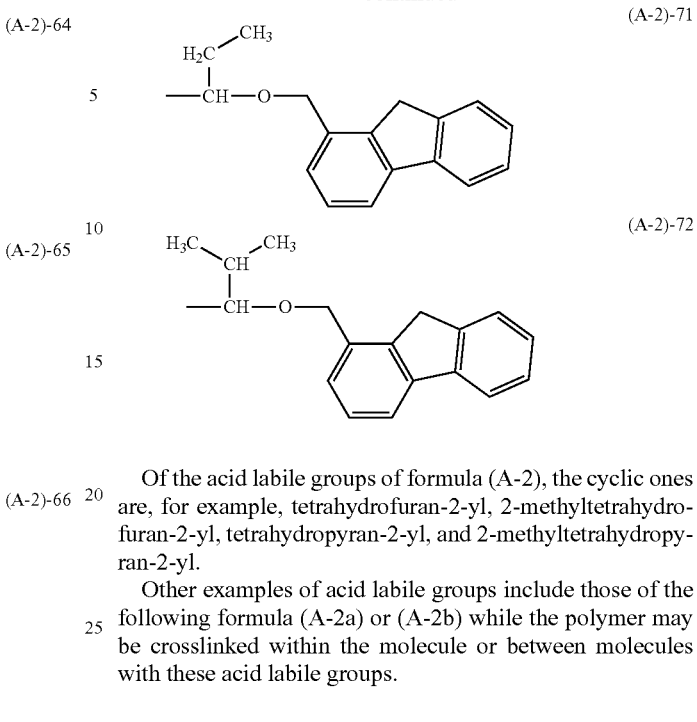

Of the acid labile groups of formula (A-2), the cyclic ones are, for example, tetrahydrofuran-2-yl, 2-methyltetrahydrofuran-2-yl, tetrahydropyran-2-yl, and 2-methyltetrahydropyran-2-yl.

Other examples of acid labile groups include those of the following formula (A-2a) or (A-2b) while the polymer may be crosslinked within the molecule or between molecules with these acid labile groups.

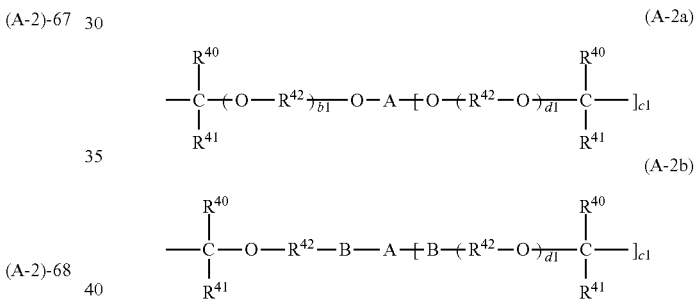

Herein $R^{40}$ and $R^{44}$ each are hydrogen or a straight, branched or cyclic $C_1$-$C_8$ alkyl group, or $R^{40}$ and $R^{41}$, taken together, may form a ring with the carbon atom to which they are attached, and $R^{40}$ and $R^{44}$ are straight or branched $C_1$-$C_8$ alkylene groups when they form a ring. $R^{42}$ is a straight, branched or cyclic $C_1$-$C_{10}$ alkylene group. Each of b1 and d1 is 0 or an integer of 1 to 10, preferably 0 or an integer of 1 to 5, and c1 is an integer of 1 to 7. "A" is a (c1+1)-valent aliphatic or alicyclic saturated hydrocarbon group, aromatic hydrocarbon group or heterocyclic group having 1 to 50 carbon atoms, which may be separated by a heteroatom or in which some of the hydrogen atoms attached to carbon atoms may be substituted by hydroxyl, carboxyl, carbonyl radicals or fluorine atoms. "B" is —CO—O—, —NHCO—O— or —NH-CONH—.

Preferably, "A" is selected from divalent to tetravalent, straight, branched or cyclic $C_1$-$C_{20}$ alkylene, alkyltriyl and alkyltetrayl groups, and $C_6$-$C_{30}$ arylene groups, which may contain a heteroatom or in which some of the hydrogen atoms attached to carbon atoms may be substituted by hydroxyl, carboxyl, acyl radicals or halogen atoms. The subscript c1 is preferably an integer of 1 to 3.

The crosslinking acetal groups of formulae (A-2a) and (A-2b) are exemplified by the following formulae (A-2)-73 through (A-2)-80.

 (A-2)-73

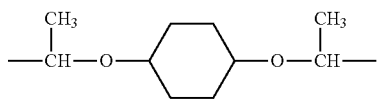 (A-2)-74

 (A-2)-75

 (A-2)-76

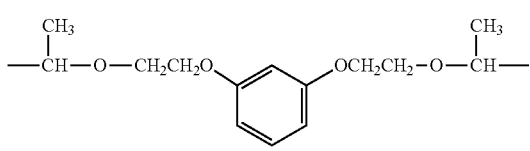 (A-2)-77

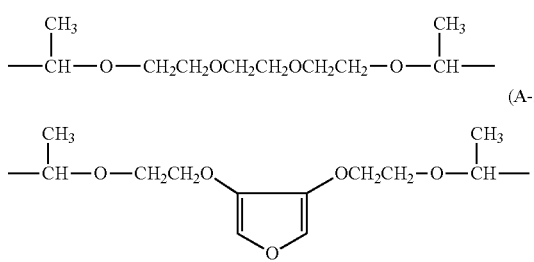 (A-2)-78

(A-2)-79

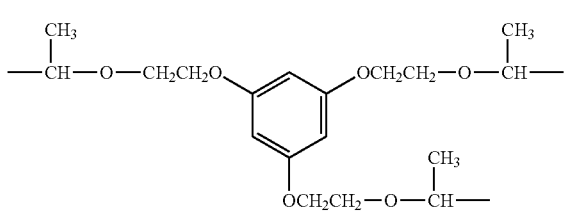

(A-2)-80

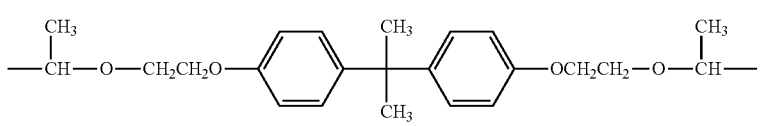

In formula (A-3), $R^{34}$, $R^{35}$ and $R^{36}$ each are hydrogen, or a monovalent hydrocarbon group, typically a straight, branched or cyclic $C_1$-$C_{20}$ alkyl group, aryl group or alkenyl group, which may contain a heteroatom such as oxygen, sulfur, nitrogen or fluorine. A pair of $R^{34}$ and $R^{35}$, $R^{34}$ and $R^{36}$, or $R^{35}$ and $R^{36}$ may bond together to form a $C_3$-$C_{20}$ ring with the carbon atom to which they are attached.

Exemplary tertiary alkyl groups of formula (A-3) include tert-butyl, triethylcarbyl, 1-ethylnorbornyl, 1-methylcyclohexyl, 1-ethylcyclopentyl, 2-(2-methyl)adamantyl, 2-(2-ethyl)adamantyl, and tert-amyl.

Other exemplary tertiary alkyl groups include those of the following formulae (A-3)-1 to (A-3)-18.

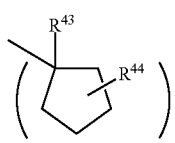 (A-3)-1

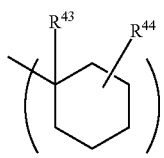 (A-3)-2

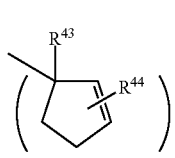 (A-3)-3

-continued

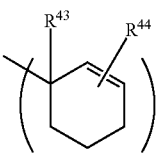 (A-3)-4

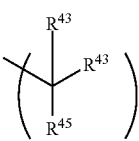 (A-3)-5

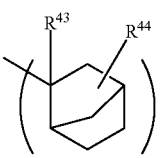 (A-3)-6

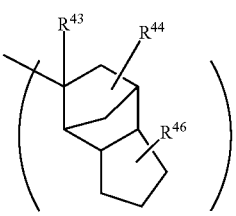 (A-3)-7

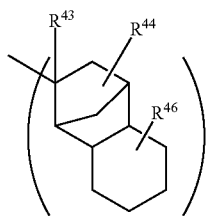
(A-3)-8

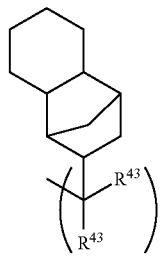
(A-3)-15

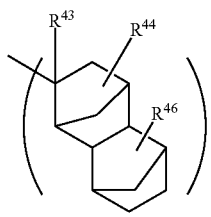
(A-3)-9

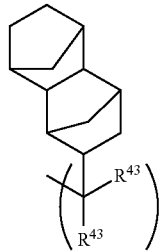
(A-3)-16

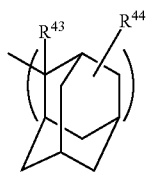
(A-3)-10

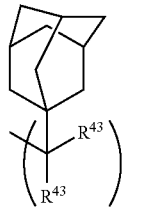
(A-3)-17

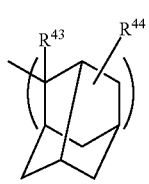
(A-3)-11

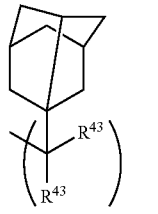
(A-3)-18

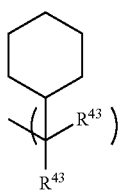
(A-3)-12

Herein $R^{43}$ is each independently a straight, branched or cyclic $C_1$-$C_8$ alkyl group or $C_6$-$C_{20}$ aryl group, typically phenyl or naphthyl. $R^{44}$ and $R^{46}$ each are hydrogen or a straight, branched or cyclic $C_1$-$C_{20}$ alkyl group. $R^{45}$ is a $C_6$-$C_{20}$ aryl group, typically phenyl.

The polymer may be crosslinked within the molecule or between molecules with groups having $R^{47}$ which is a di- or multi-valent alkylene or arylene group, as shown by the following formulae (A-3)-19 and (A-3)-20.

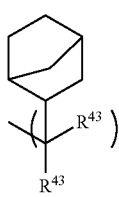
(A-3)-13

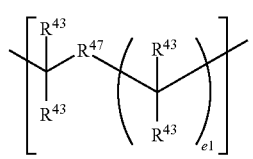
(A-3)-19

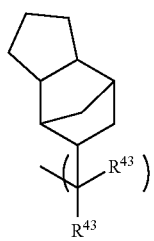
(A-3)-14

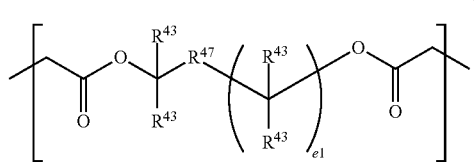
(A-3)-20

Herein $R^{43}$ is as defined above, $R^{47}$ is a straight, branched or cyclic $C_1$-$C_{20}$ alkylene group or arylene group, typically phenylene, which may contain a heteroatom such as oxygen, sulfur or nitrogen, and e1 is an integer of 1 to 3.

Examples of $R^{30}$, $R^{33}$ and $R^{36}$ in formulae (A-1), (A-2) and (A-3) include substituted or unsubstituted aryl groups such as phenyl, p-methylphenyl, p-ethylphenyl, and alkoxy-substituted phenyl groups, typically p-methoxyphenyl, and aralkyl groups such as benzyl and phenethyl, and modified forms of the foregoing groups in which an oxygen atom is introduced, and modified forms of alkyl groups in which a carbon-bonded hydrogen atom is replaced by a hydroxyl radical, or oxoalkyl groups in which two hydrogen atoms are replaced by an oxygen atom to form a carbonyl group, as represented by the following formulae.

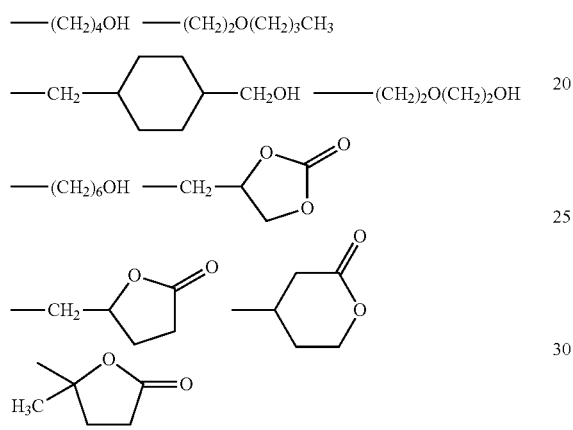

Of recurring units having acid labile groups of formula (A-3), recurring units of (meth)acrylate having an exo-form structure represented by the formula (A-3)-21 are preferred.

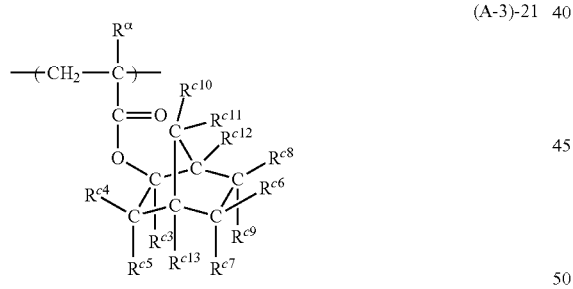

(A-3)-21

Herein, $R^\alpha$ is hydrogen or methyl; $R^{c3}$ is a straight, branched or cyclic $C_1$-$C_8$ alkyl group or an optionally substituted $C_6$-$C_{20}$ aryl group; $R^{c4}$ to $R^{c9}$, $R^{c12}$ and $R^{c13}$ are each independently hydrogen or a monovalent $C_1$-$C_{15}$ hydrocarbon group which may contain a heteroatom; and $R^{c10}$ and $R^{c11}$ each are hydrogen or a monovalent $C_1$-$C_{15}$ hydrocarbon group which may contain a heteroatom. Alternatively, a pair of $R^{c4}$ and $R^{c5}$, $R^{c6}$ and $R^{c8}$, $R^{c6}$ and $R^{c9}$, $R^{c7}$ and $R^{c9}$, $R^{c7}$ and $R^{c13}$, $R^{c8}$ and $R^{c12}$, $R^{c10}$ and $R^{c11}$, or $R^{c11}$ and $R^{c12}$, taken together, may form a non-aromatic ring with the carbon atom to which they are attached, and in that event, each ring-forming R is a divalent $C_1$-$C_{15}$ hydrocarbon group, typically alkylene which may contain a heteroatom. Also, a pair of $R^{c4}$ and $R^{c13}$, $R^{c10}$ and $R^{c13}$, or $R^{c6}$ and $R^{c8}$ which are attached to vicinal carbon atoms may bond together directly to form a double bond. The formula also represents an enantiomer.

The ester form monomers from which recurring units having an exo-form structure represented by formula (A-3)-21 are derived are described in U.S. Pat. No. 6,448,420 (JP-A 2000-327633). Illustrative non-limiting examples of suitable monomers are given below.

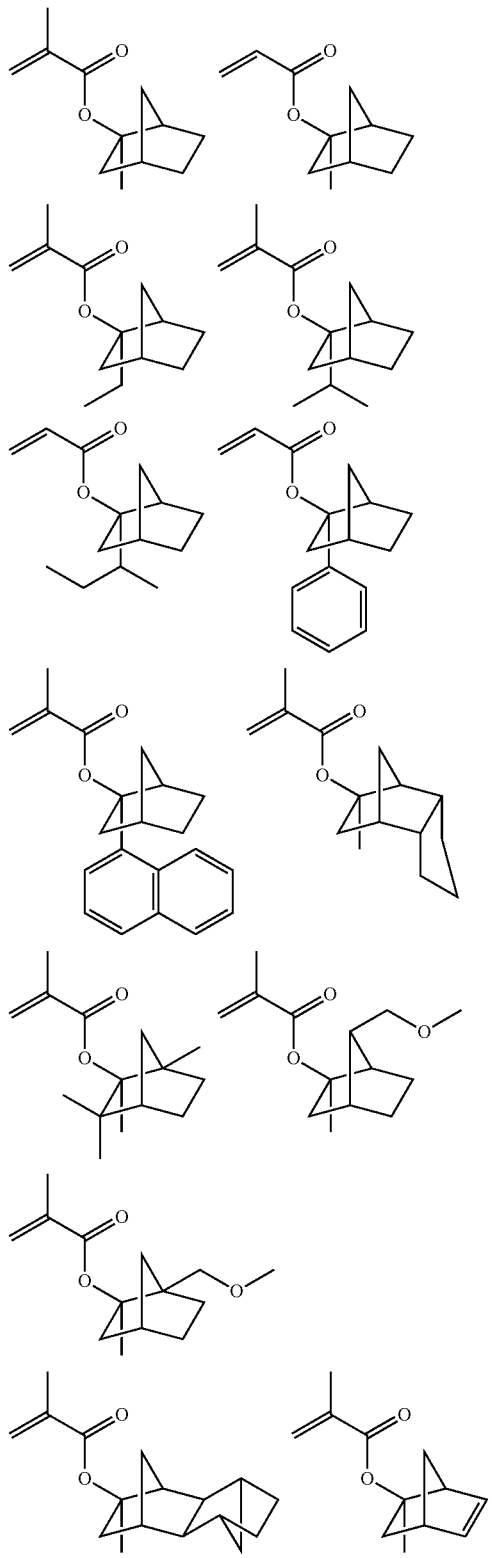

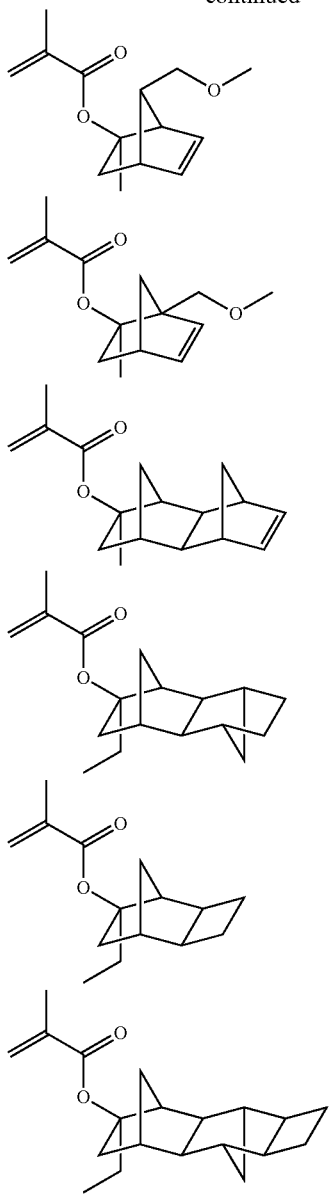

Also included in the acid labile groups of formula (A-3) are acid labile groups of (meth)acrylate having furandiyl, tetrahydrofurandiyl or oxanorbornanediyl as represented by the following formula (A-3)-22.

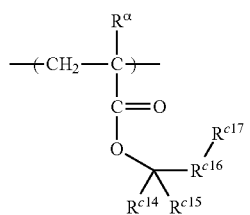

(A-3)-22

Herein, $R^\alpha$ is as defined above. $R^{c14}$ and $R^{c15}$ are each independently a monovalent, straight, branched or cyclic $C_1$-$C_{10}$ hydrocarbon group, or $R^{c14}$ and $R^{c15}$, taken together, may form a $C_3$-$C_8$ aliphatic hydrocarbon ring with the carbon atom to which they are attached. $R^{c16}$ is a divalent group selected from furandiyl, tetrahydrofurandiyl and oxanorbornanediyl. $R^{c17}$ is hydrogen or a monovalent, straight, branched or cyclic $C_1$-$C_{10}$ hydrocarbon group which may contain a heteroatom.

Examples of the monomers from which the recurring units substituted with acid labile groups having furandiyl, tetrahydrofurandiyl and oxanorbornanediyl are derived are shown below. Note that Me is methyl and Ac is acetyl.

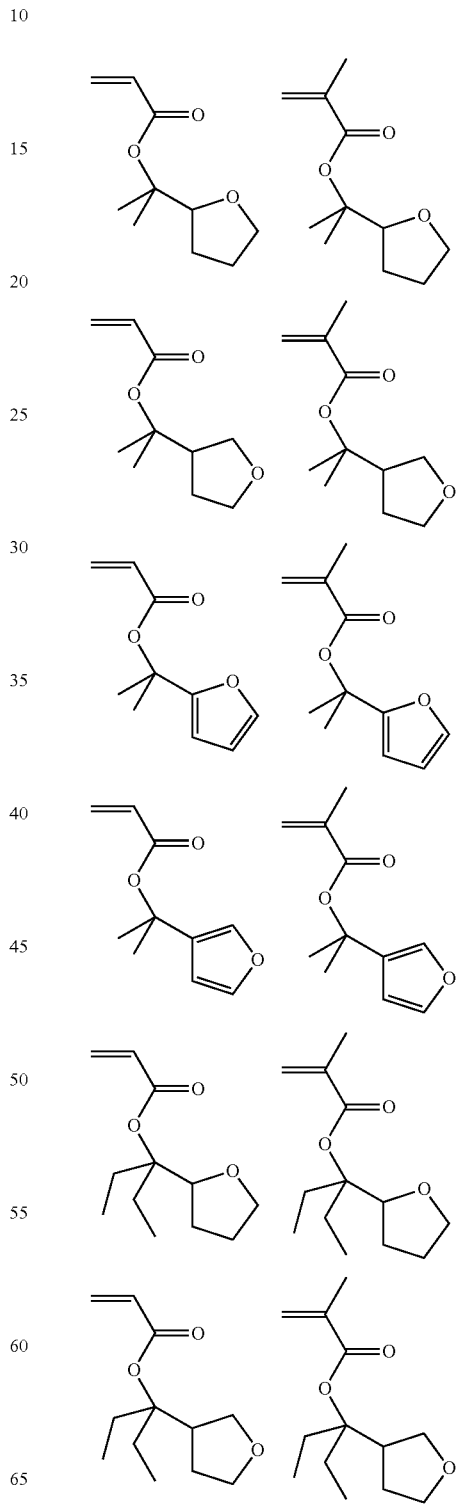

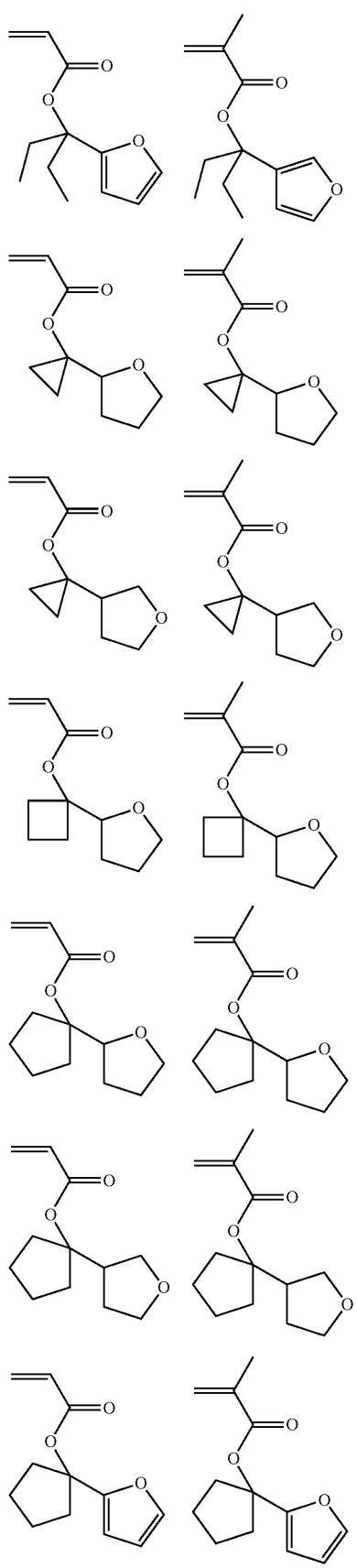
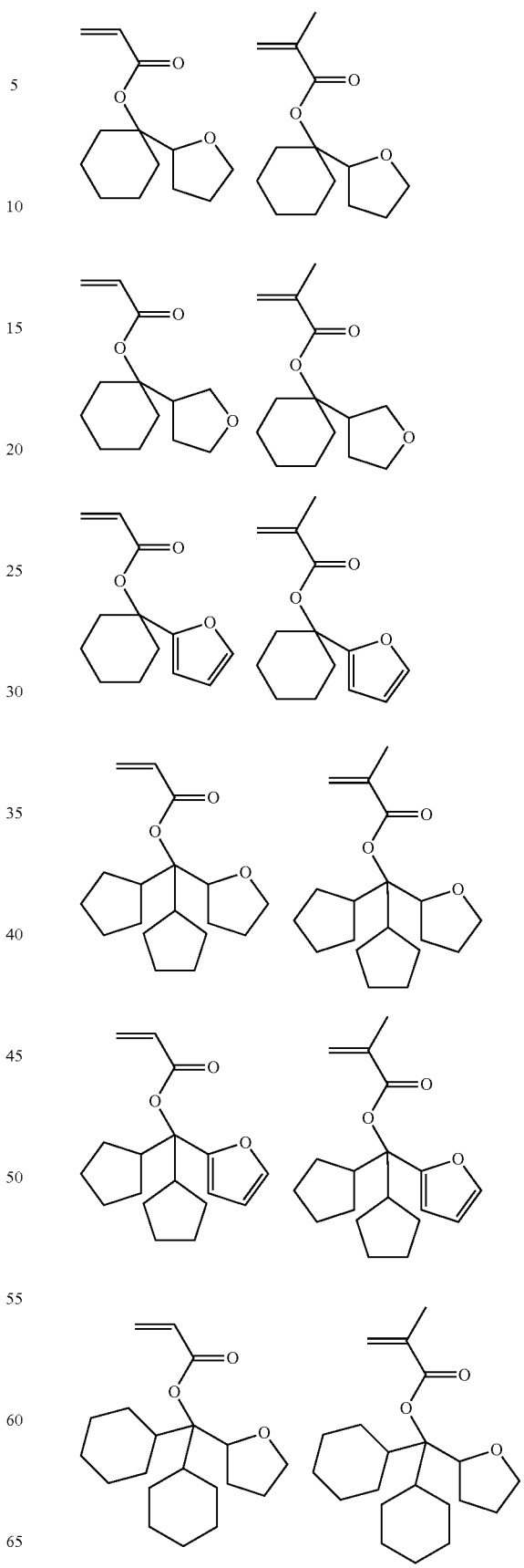

-continued
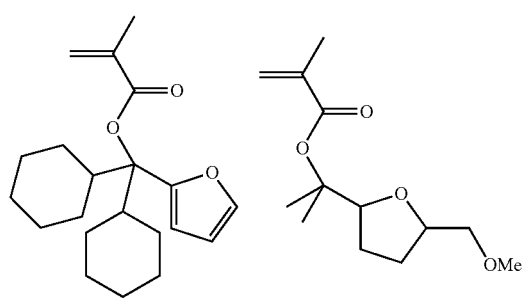
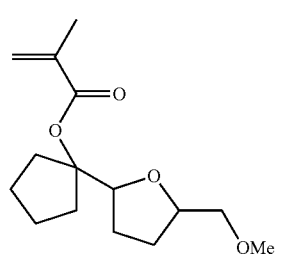
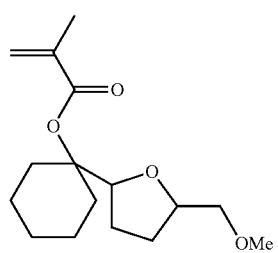
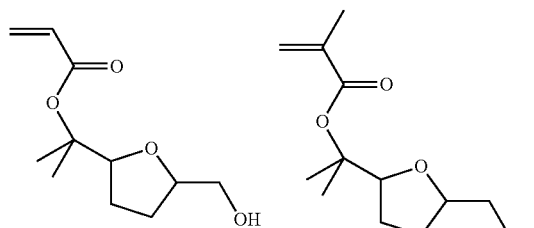
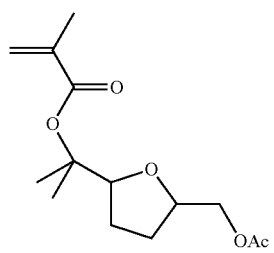
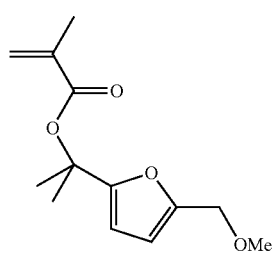
-continued
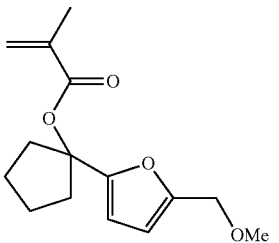
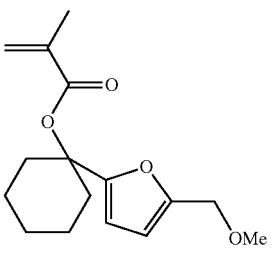
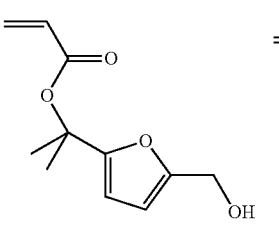
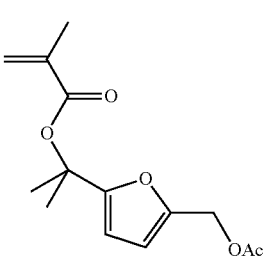
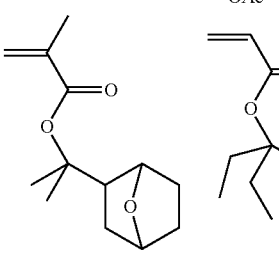
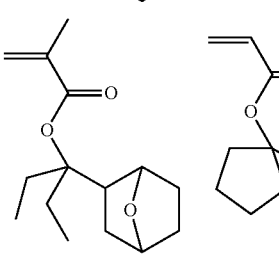
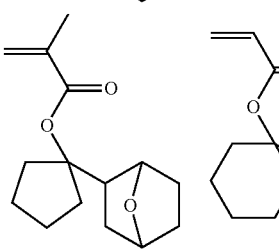

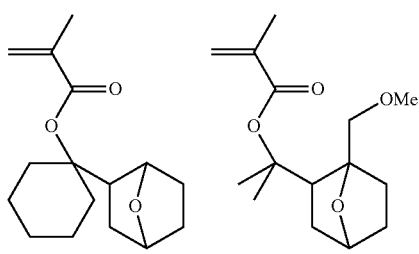
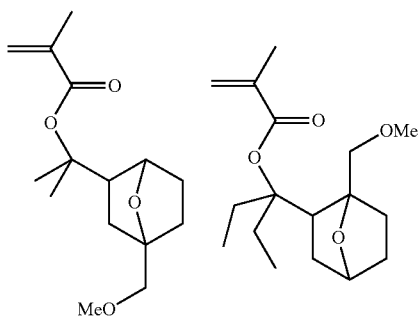
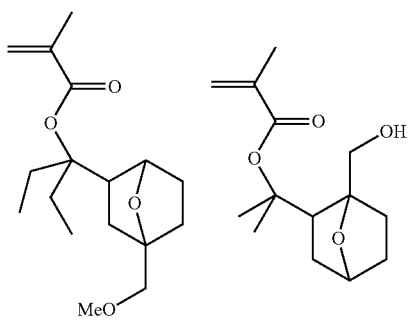
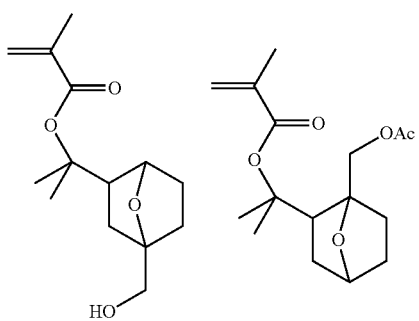
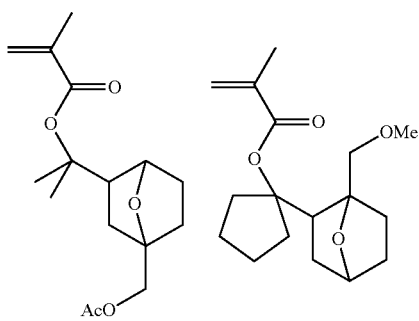
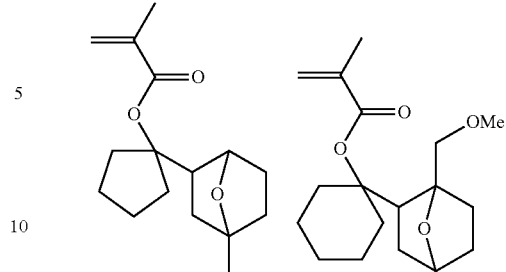
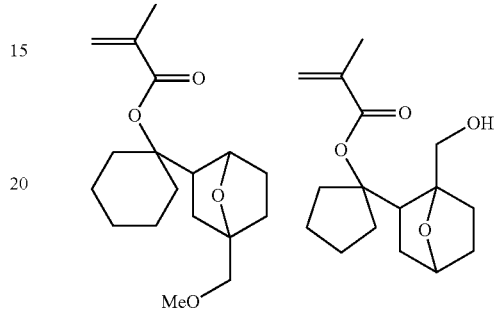
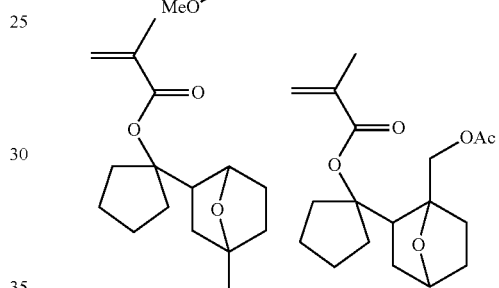
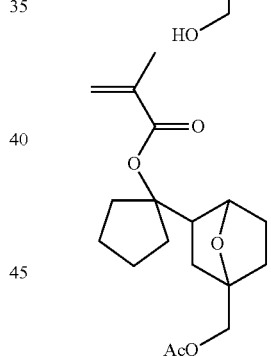
As the recurring units having an acid labile group, recurring units having a secondary acid labile group may also be copolymerized. Examples of suitable monomers from which units having a secondary acid labile group are derived are given below.
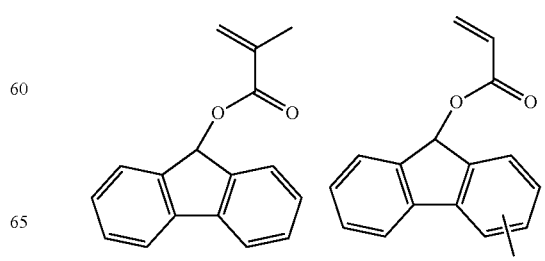

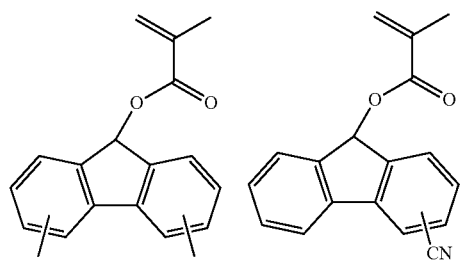
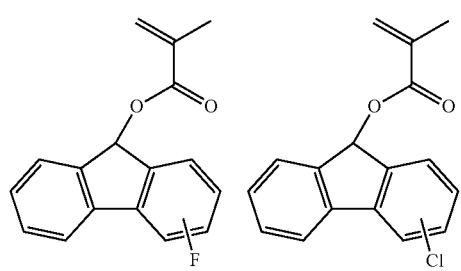
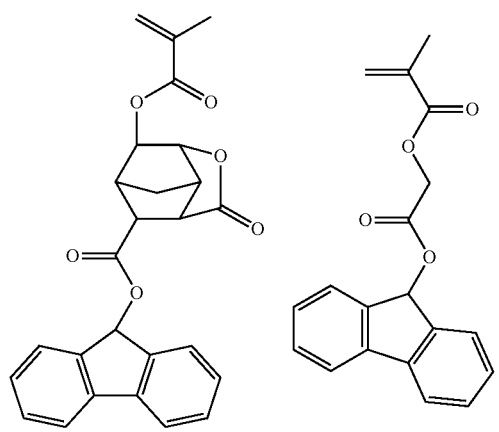
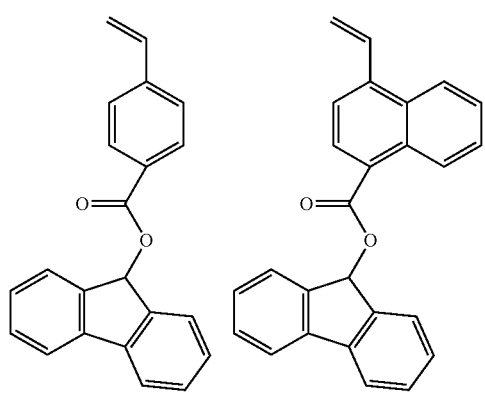
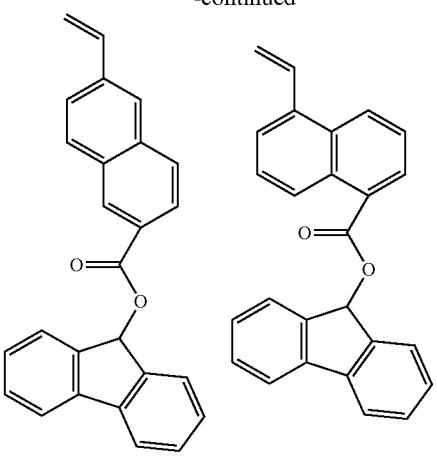
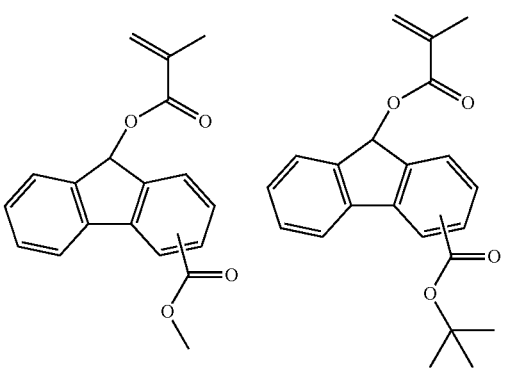
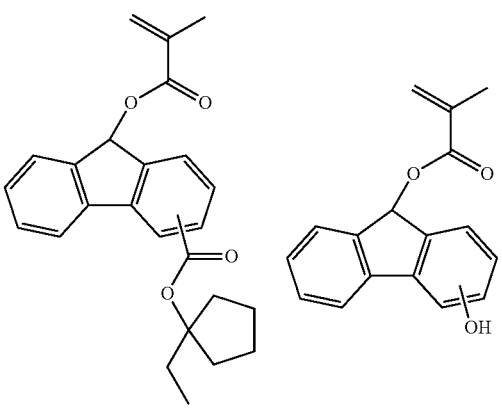
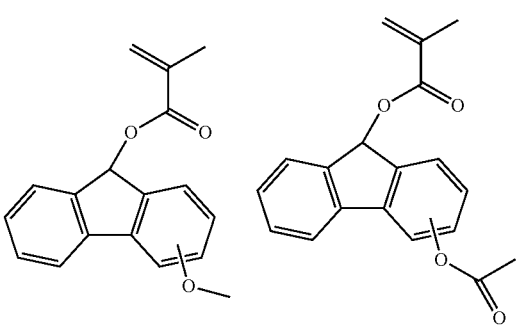

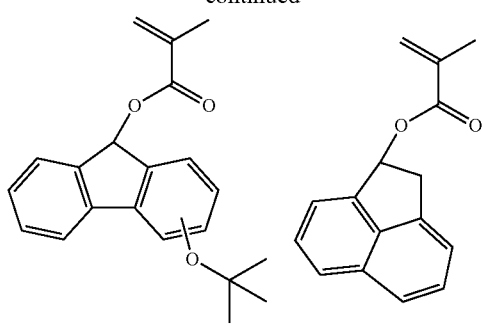
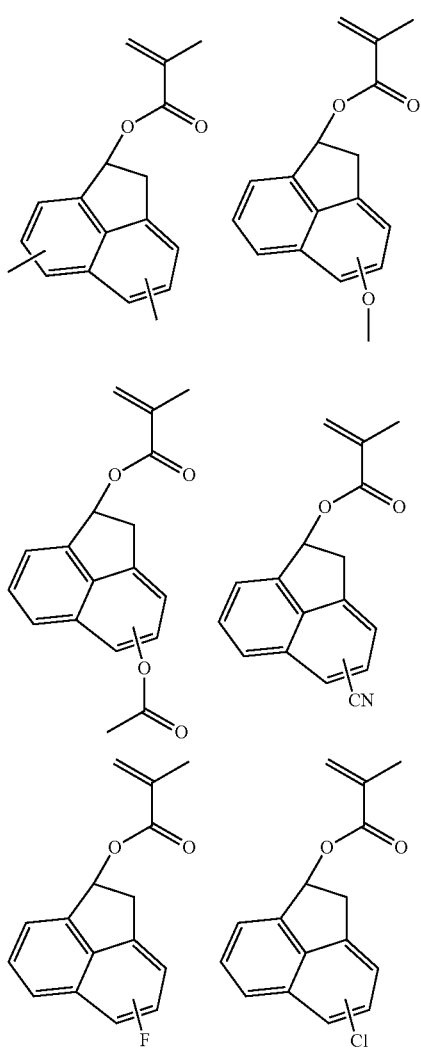
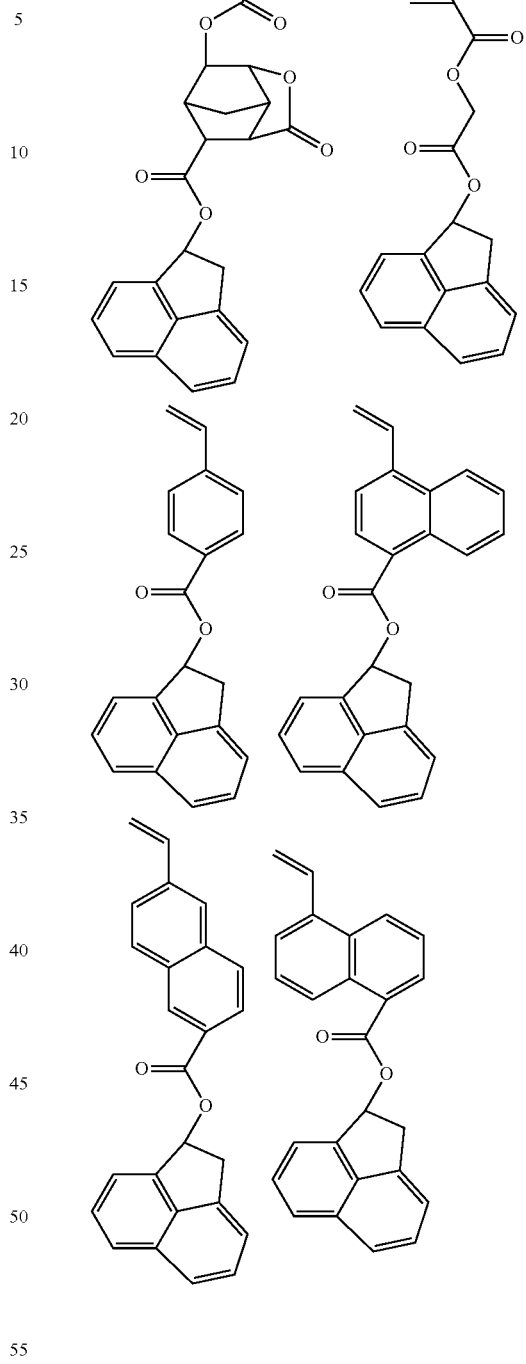

In addition to recurring units (a1) of (meth)acrylate, styrenecarboxylic acid and vinylnaphthalenecarboxylic acid having an acid labile group substituted thereon, and recurring units (a2) of hydroxystyrene having an acid labile group substituted thereon, the base polymer in the chemically amplified positive resist composition may have further copolymerized therein recurring units (b) having a phenolic hydroxyl group as an adhesive group. Examples of suitable monomers from which recurring units (b) having a phenolic hydroxyl group are derived are given below.

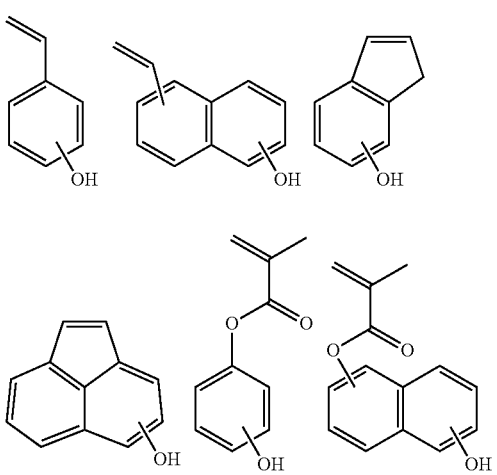
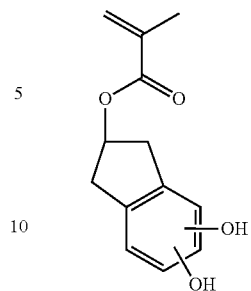
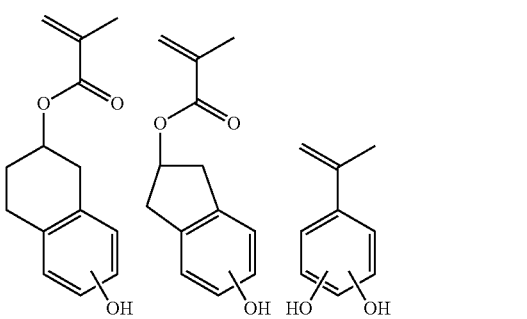
Further, recurring units (c) having another adhesive group selected from hydroxyl, lactone ring, ether, ester, carbonyl and cyano groups may also be copolymerized. Examples of suitable monomers from which recurring units (c) are derived are given below.
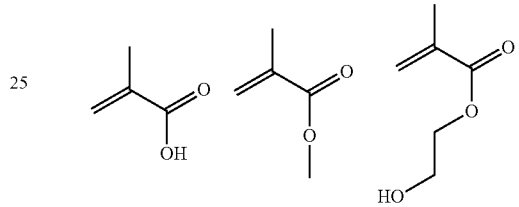
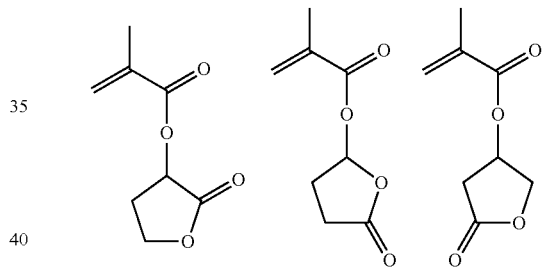
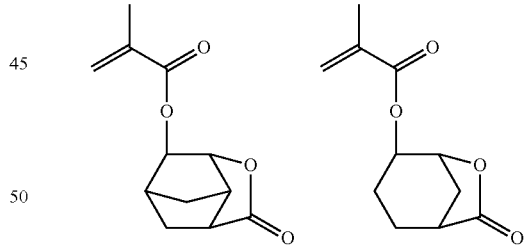
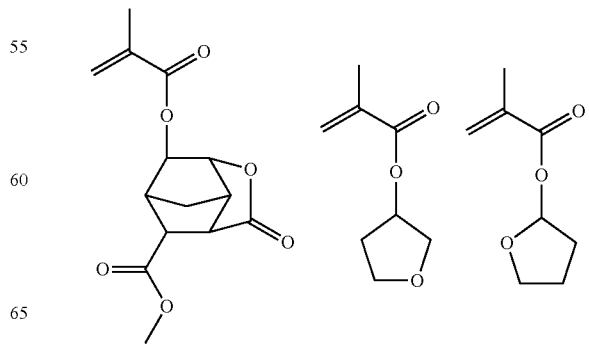

91
-continued
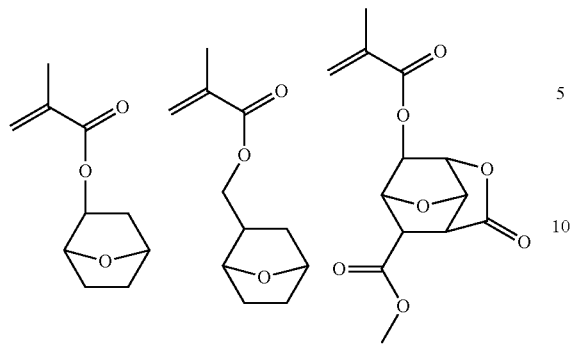
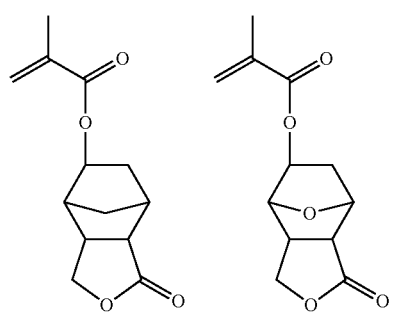
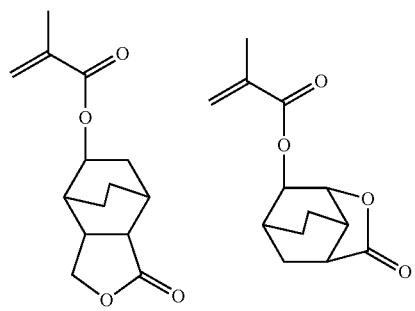
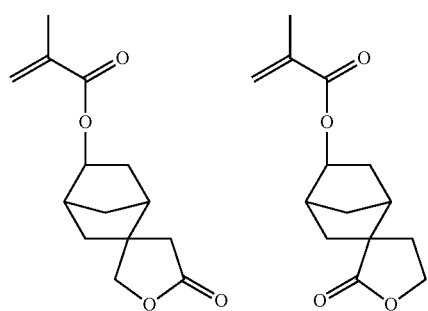
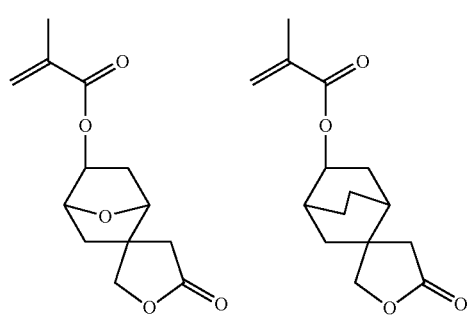
92
-continued
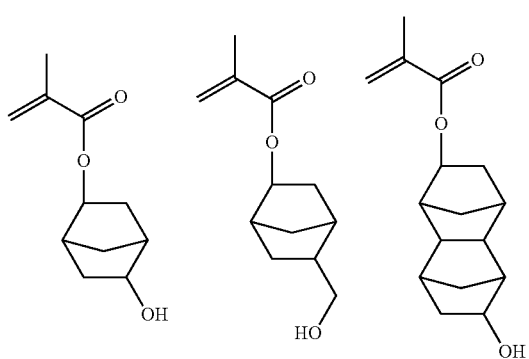
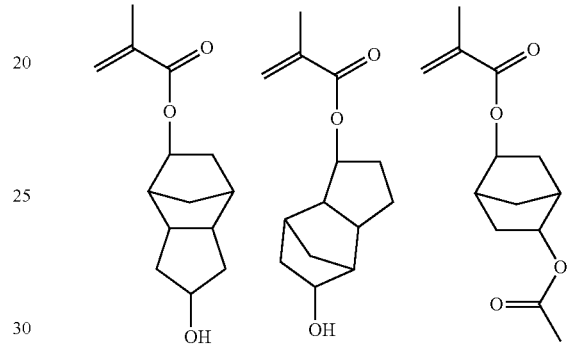
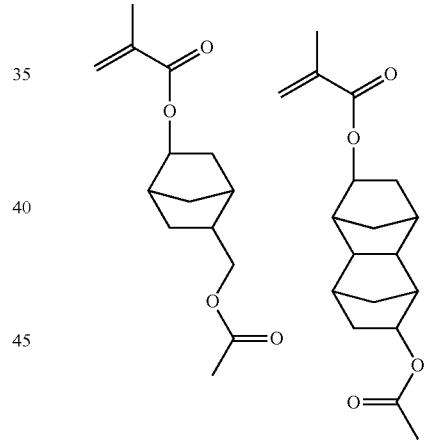
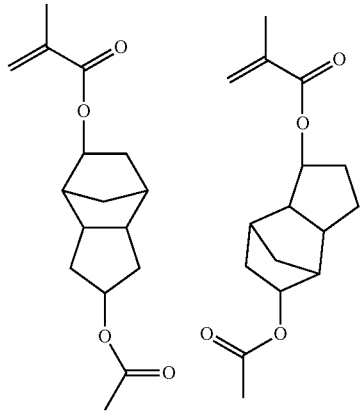

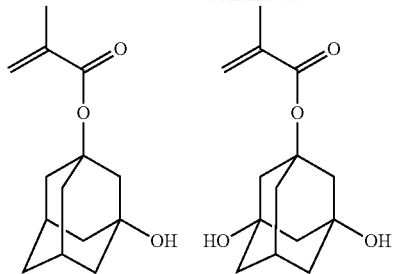
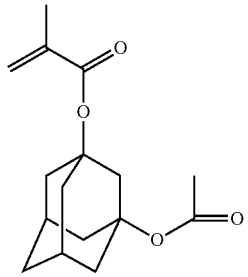
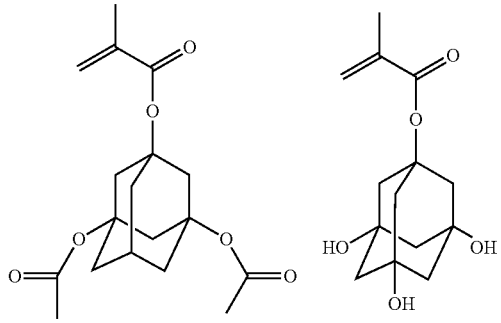
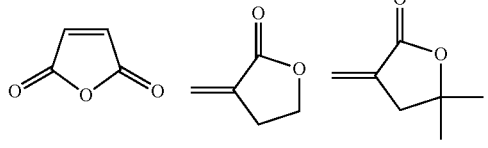
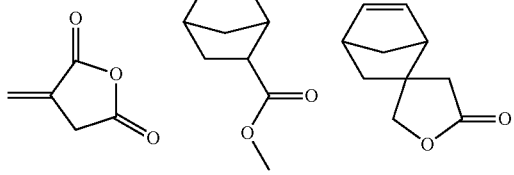
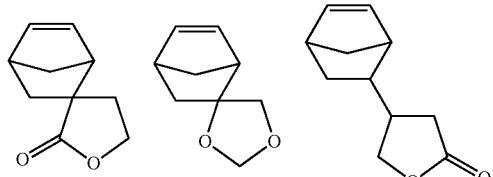
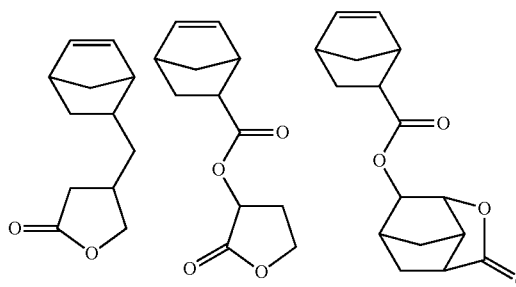
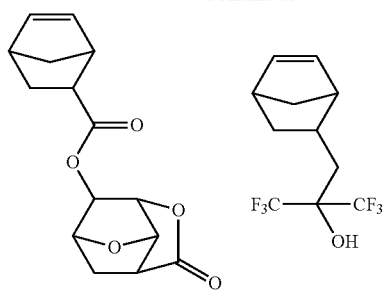
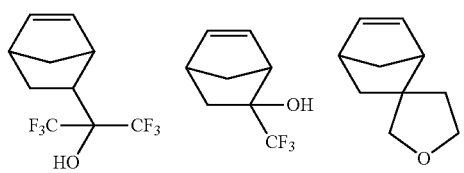
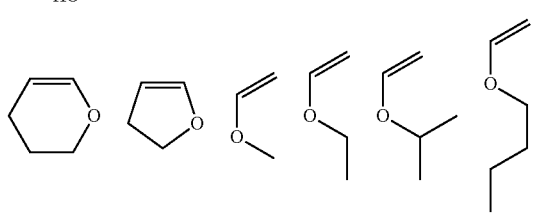
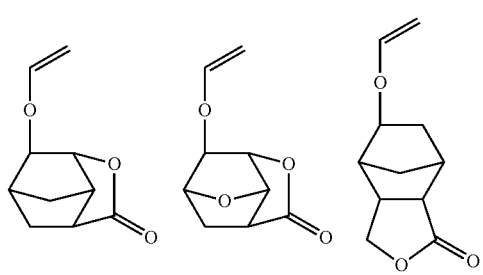
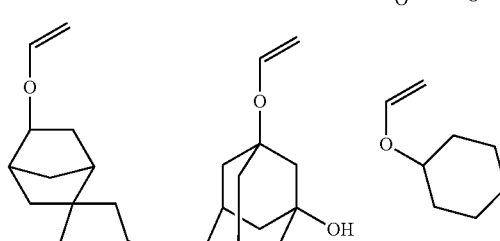
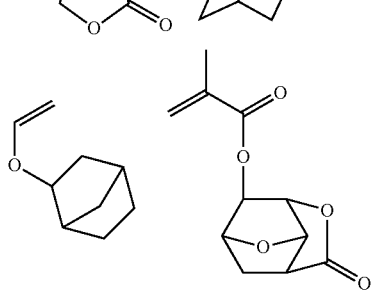
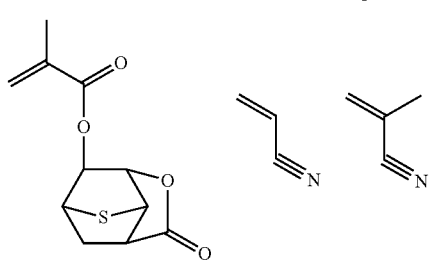

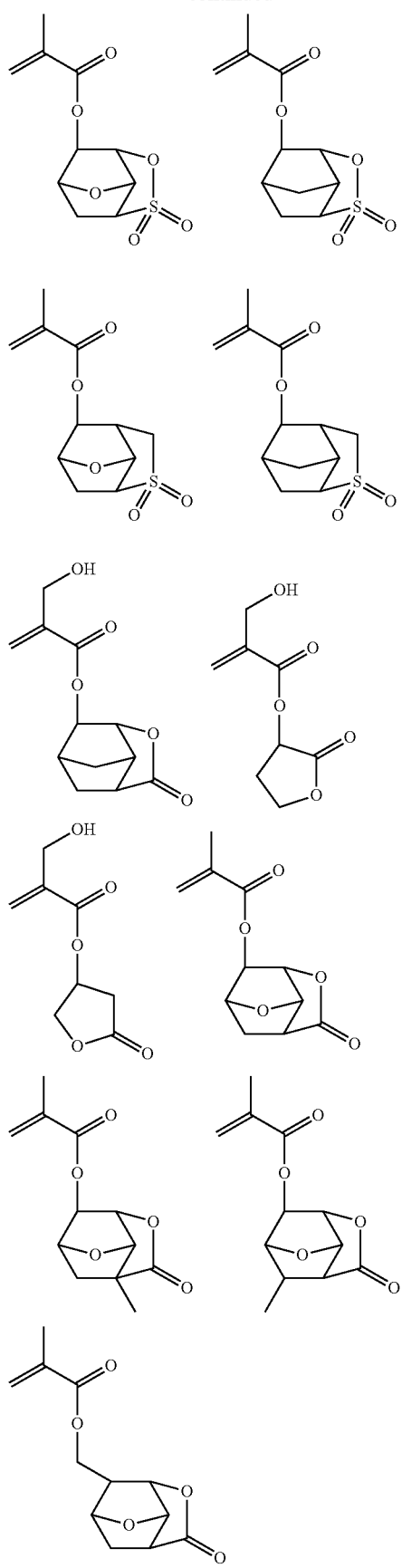
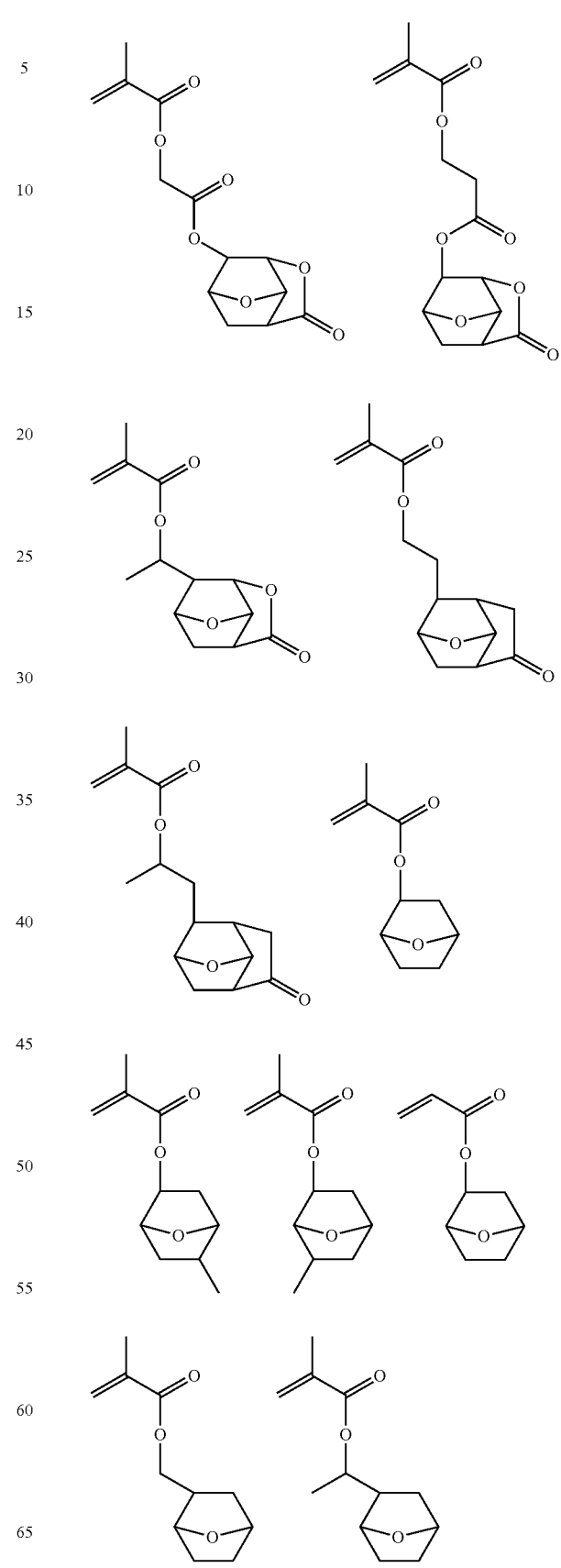

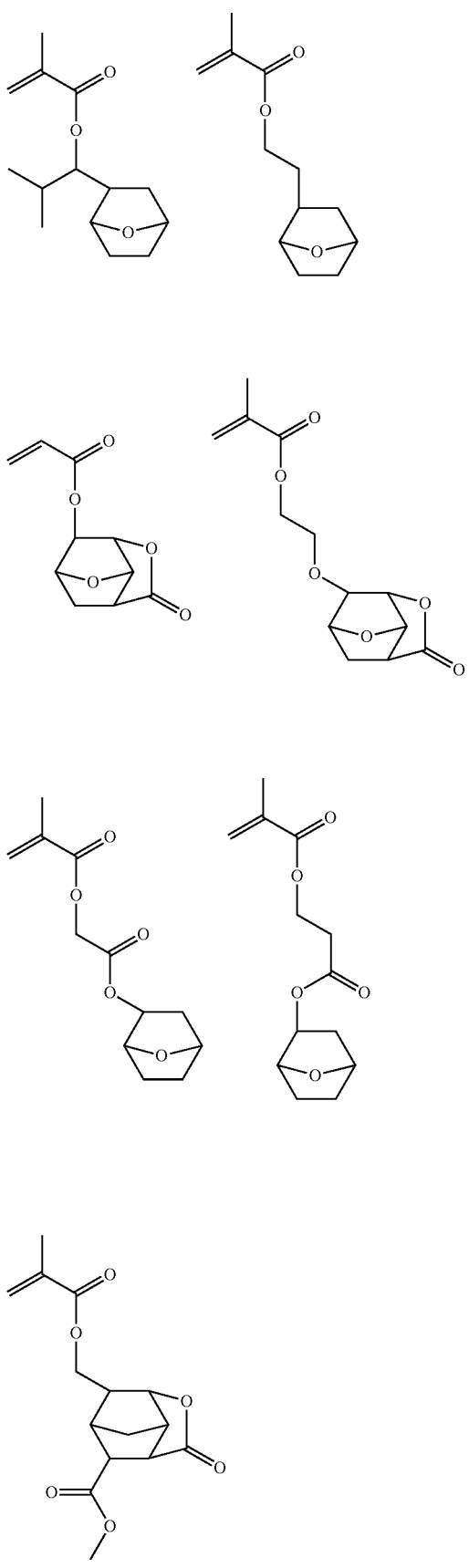
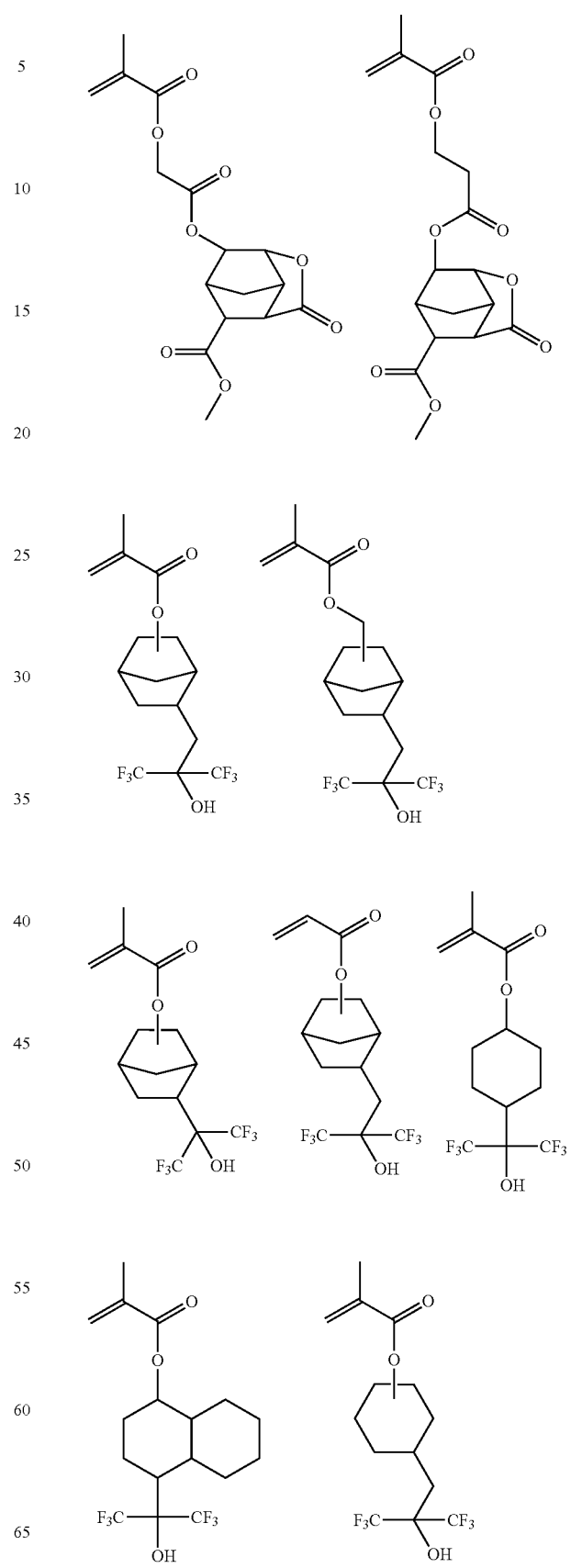

99
-continued
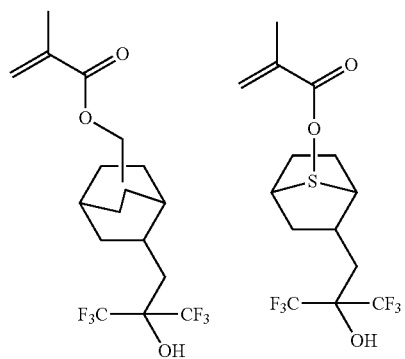
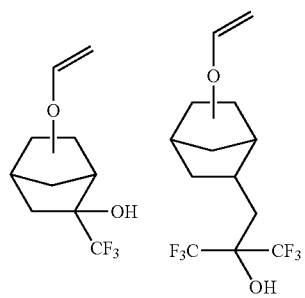
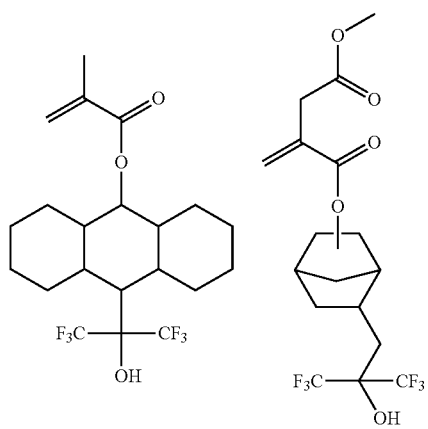
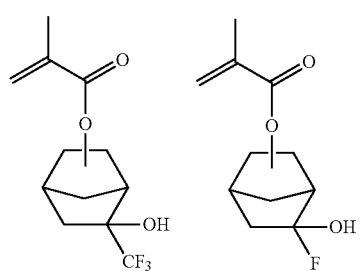
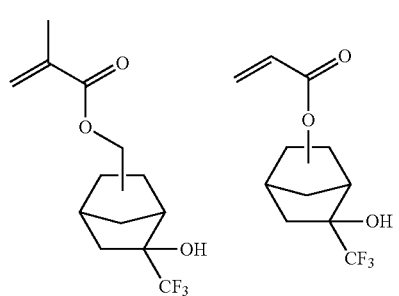
100
-continued
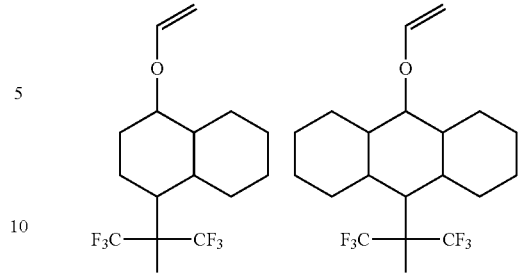
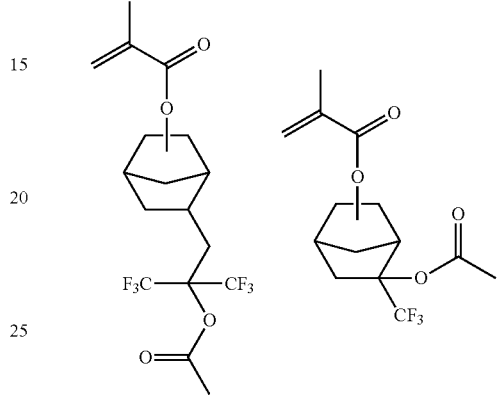
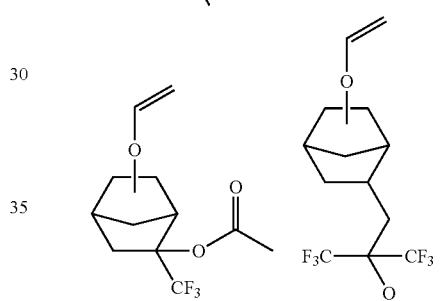
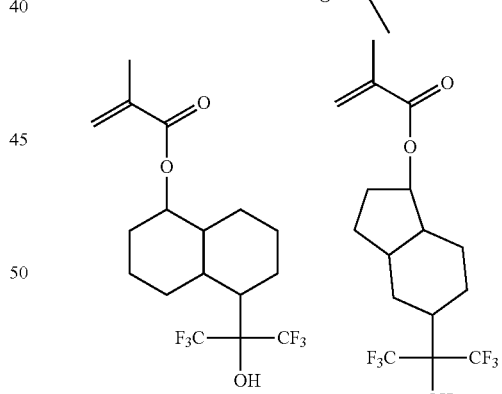
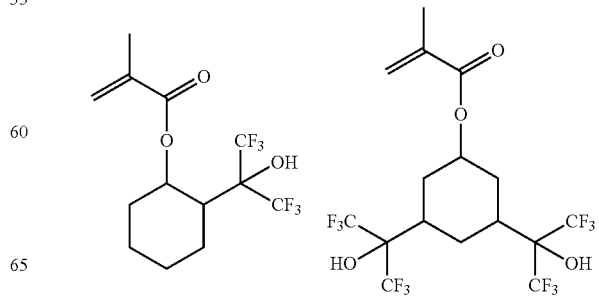

101
-continued
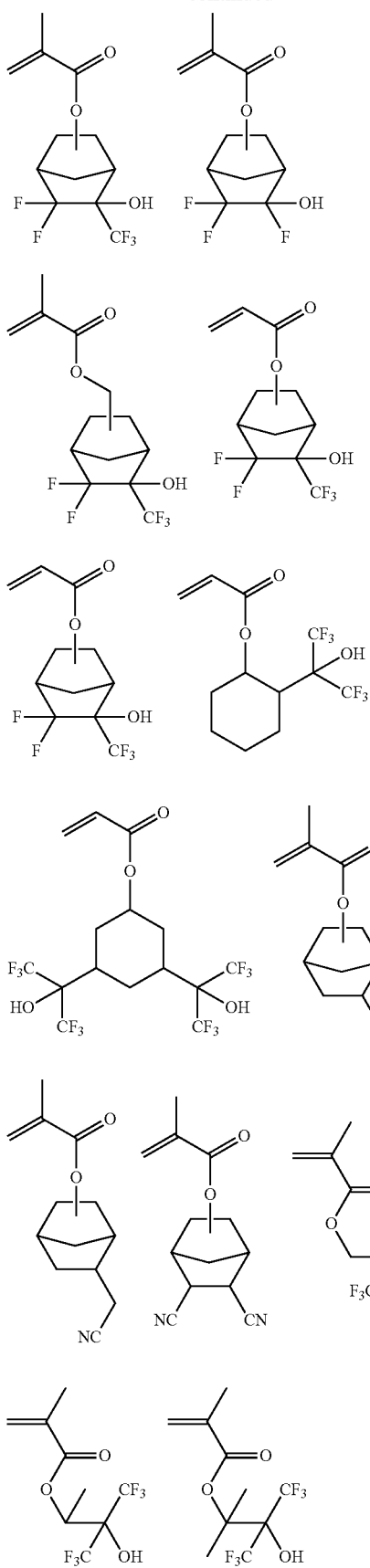
102
-continued
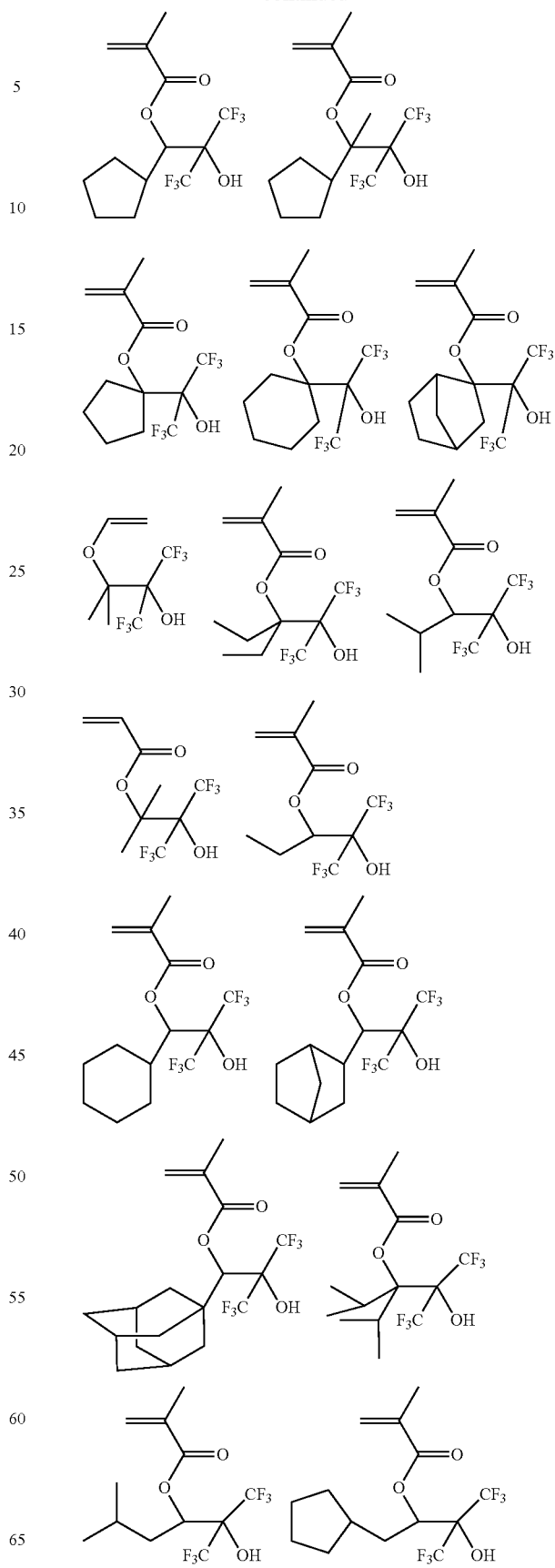

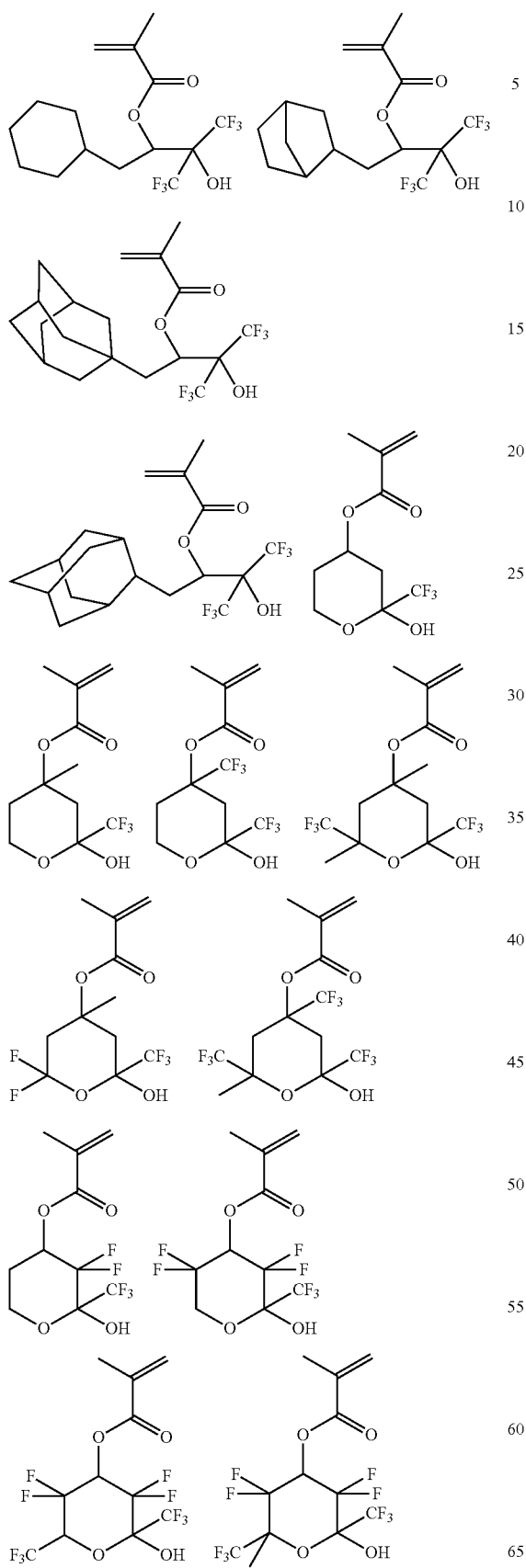
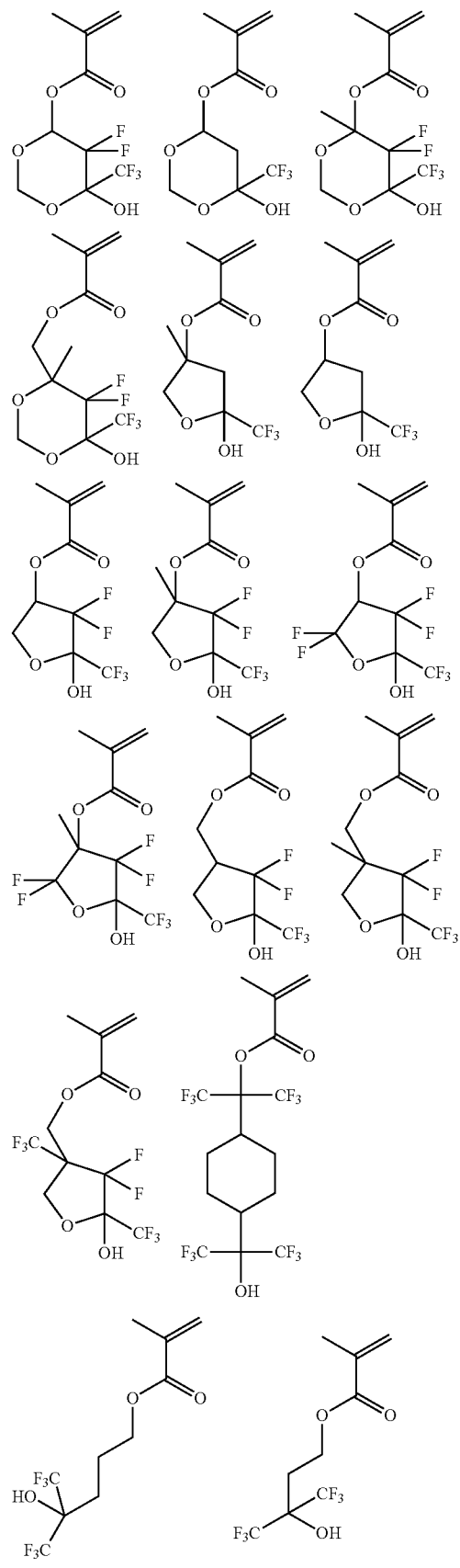

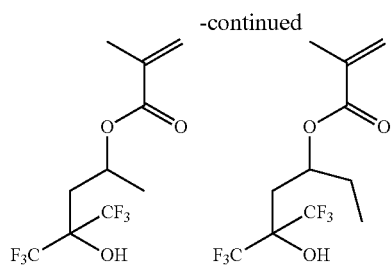
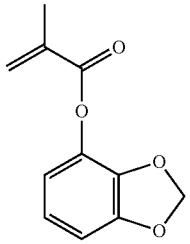
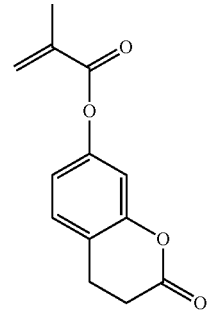
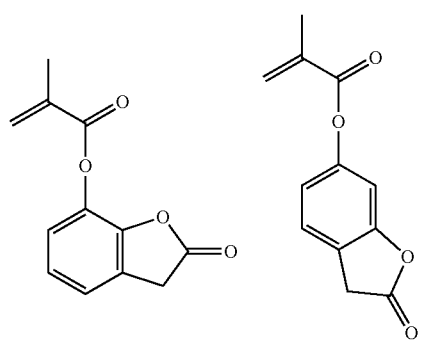
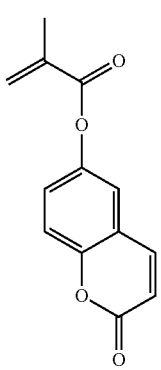
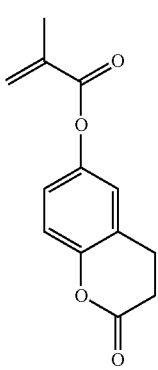
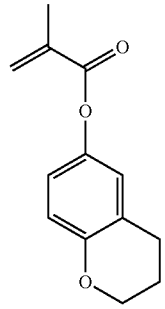
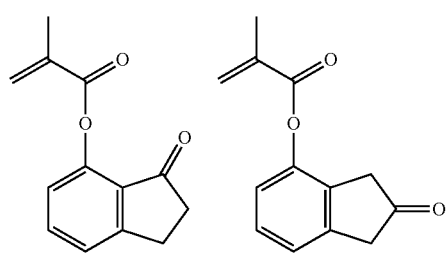
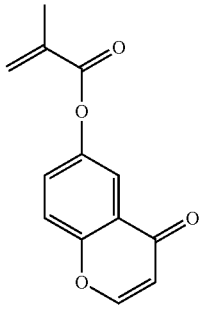
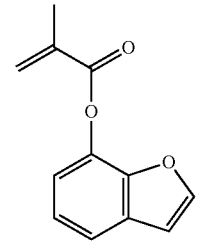
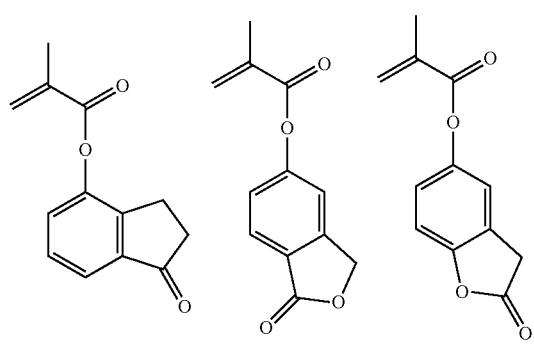
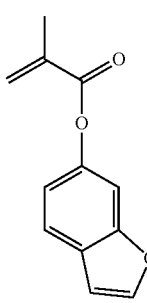
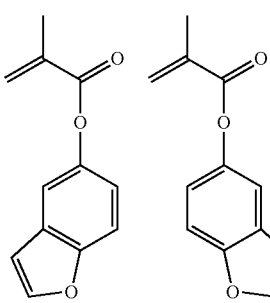
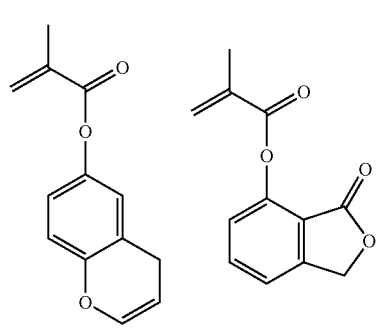
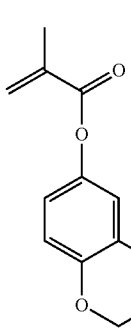
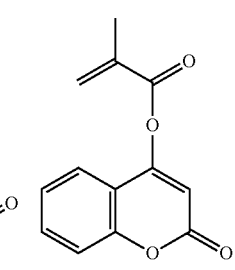

107
-continued
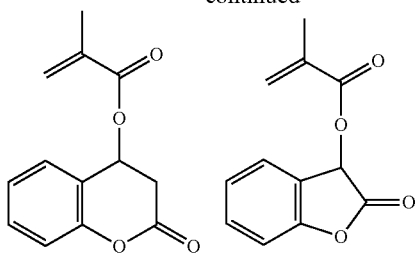
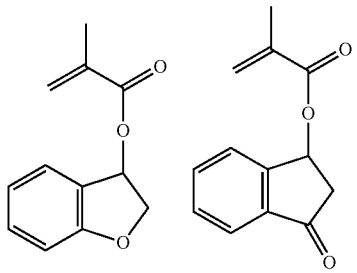
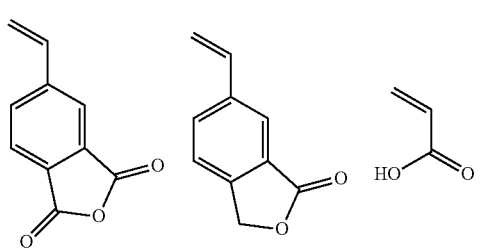
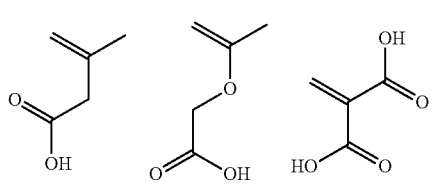
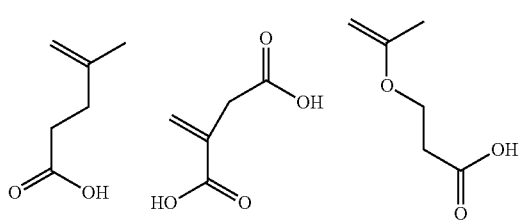
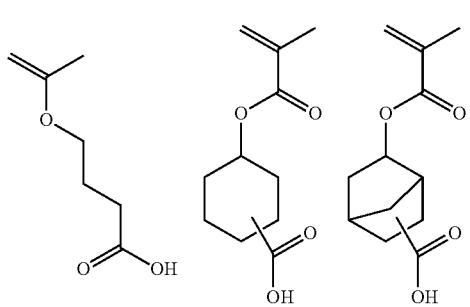
108
-continued
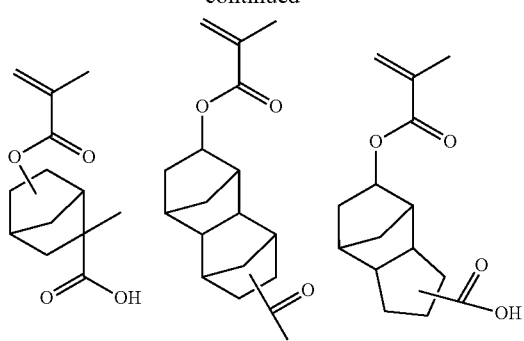
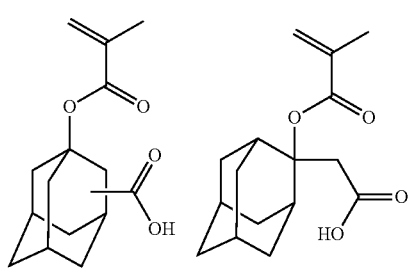
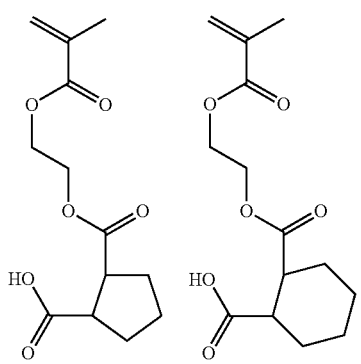
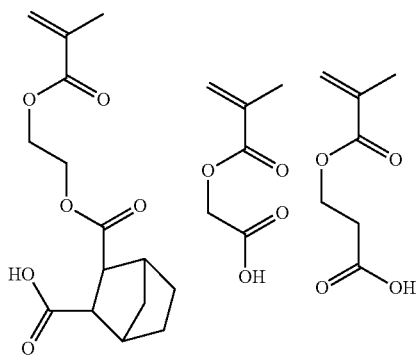
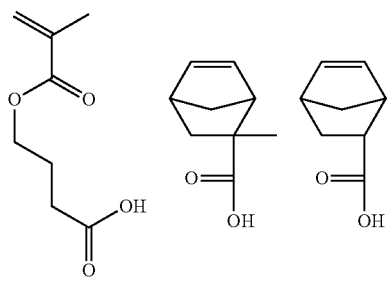

-continued

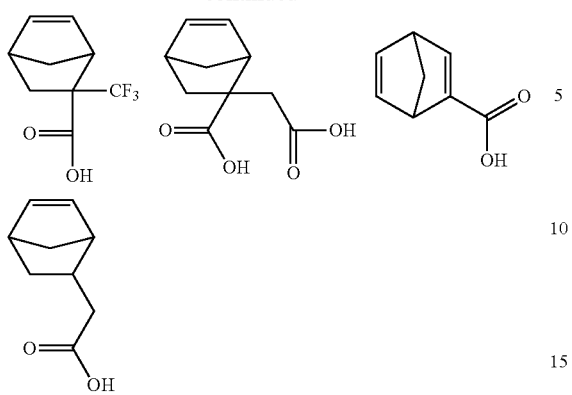
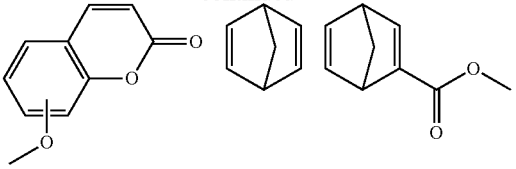

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxy group may be replaced by an acetyl, formyl, pivaloyl or similar group prior to polymerization, and the polymerization be followed by alkaline hydrolysis.

In another preferred embodiment, the copolymer may have further copolymerized therein recurring units (d) selected from units of indene, benzofuran, benzothiophene, acenaphthylene, chromone, coumarin, and norbornadiene, or derivatives thereof. Suitable monomers are exemplified below.

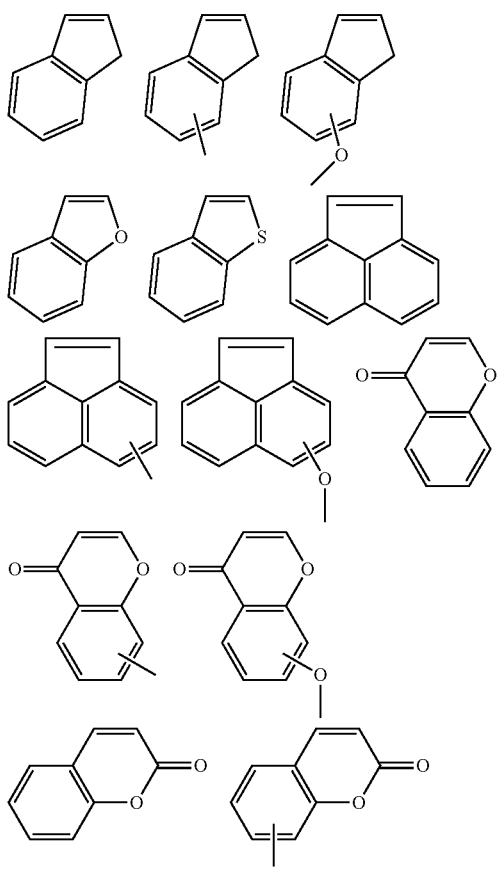

Besides the recurring units described above, further recurring units (e) can be copolymerized, examples of which include styrene, vinylnaphthalene, vinylanthracene, vinylpyrene, methyleneindene, vinylpyridine, and vinylcarbazole.

In a further embodiment, an acid generator (f) in the form of an onium salt having polymerizable olefin may be copolymerized with the foregoing monomers. JP-A 2005-084365 discloses sulfonium salts having polymerizable olefin capable of generating a sulfonic acid and similar iodonium salts. JP-A 2006-178317 discloses a sulfonium salt having sulfonic acid directly attached to the main chain.

In this embodiment, the copolymer may have further copolymerized therein recurring units having a sulfonium salt (f1) to (f3) represented by the general formula (3).

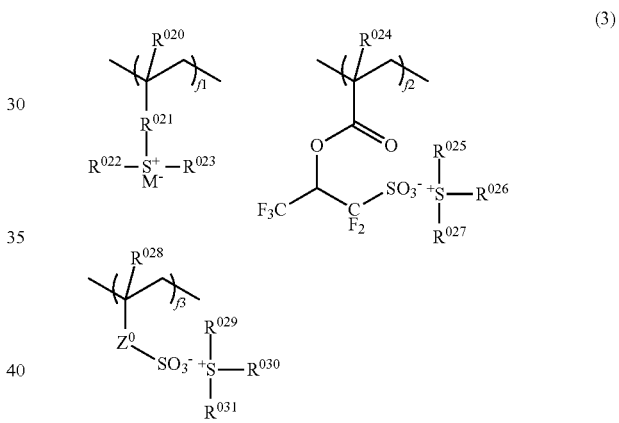

(3)

Herein $R^{020}$, $R^{024}$ and $R^{028}$ each are hydrogen or methyl. $R^{021}$ is phenylene, —O—$R^0$—, or —C(=O)—$Y^0$—$R^0$— wherein $Y^0$ is oxygen or NH and $R^0$ is a straight, branched or cyclic $C_1$-$C_6$ alkylene group, alkenylene group or phenylene group, which may contain a carbonyl (—CO—), ester (—COO—), ether (—O—) or hydroxyl radical. $R^{022}R^{023}R^{025}$, $R^{026}R^{027}$, $R^{029}$, $R^{030}$, and $R^{031}$ are each independently a straight, branched or cyclic $C_1$-$C_{12}$ alkyl group which may contain a carbonyl, ester or ether radical, or a $C_6$-$C_{12}$ aryl group, $C_7$-$C_{20}$ aralkyl group, or thiophenyl group. $Z^0$ is a single bond, methylene, ethylene, phenylene, fluorinated phenylene, —O—$R^{032}$—, or —C(=O)—$Z^1$—$R^{032}$— wherein $Z^1$ is oxygen or NH and $R^{032}$ is a straight, branched or cyclic $C_1$-$C_6$ alkylene group, alkenylene group or phenylene group, which may contain a carbonyl, ester, ether or hydroxyl radical. $M^-$ is a non-nucleophilic counter ion, and f1, f2 and f3 are in the range: $0 \le f1 \le 0.3$, $0 \le f2 \le 0.3$, $0 \le f3 \le 0.3$, and $0 \le f1+f2+f3 \le 0.3$.

Examples of the non-nucleophilic counter ion $M^-$ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; methidates such as tris(trifluoromethylsulfonyl)methide and tris(perfluoroethylsulfonyl)methide.

Also included are sulfonates having fluorine substituted at α-position as represented by the general formula (K-1) and sulfonates having fluorine substituted at α- and β-positions as represented by of the general formula (K-2).

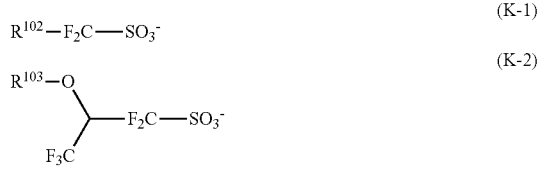

In formula (K-1), $R^{102}$ is hydrogen, or a straight, branched or cyclic $C_1$-$C_{20}$ alkyl group, $C_2$-$C_{20}$ alkenyl group, or $C_6$-$C_{20}$ aryl group, which may have an ether, ester, carbonyl radical, lactone ring, or fluorine atom. In formula (K-2), $R^{103}$ is hydrogen, or a straight, branched or cyclic $C_1$-$C_{30}$ alkyl or acyl group, $C_2$-$C_{20}$ alkenyl group, or $C_6$-$C_{20}$ aryl or aryloxy group, which may have an ether, ester, carbonyl radical or lactone ring.

Onium salts such as sulfonium salts, iodonium salts and ammonium salts of sulfonic acids which are not fluorinated at α-position as described in US 2008153030 (JP-A 2008-158339) and similar onium salts of carboxylic acid may also be used as the quencher. While an α-fluorinated sulfonic acid, imidic acid, and methidic acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction. In particular, since sulfonium salts and iodonium salts of an α-non-fluorinated sulfonic acid and a carboxylic acid are photo-decomposable, those portions receiving a high light intensity are reduced in quenching capability and increased in the concentration of a α-fluorinated sulfonic acid, imidic acid, or methidic acid. As a result, the exposed portions are improved in contrast. When a negative tone pattern is formed using an organic solvent, the improvement in the contrast of exposed portions leads to an improvement in the rectangularity of negative pattern. Onium salts including sulfonium salts, iodonium salts and ammonium salts of an α-non-fluorinated sulfonic acid and a carboxylic acid are highly effective in controlling the diffusion of an α-fluorinated sulfonic acid, imidic acid and methidic acid. This is because the onium salt resulting from salt exchange is less mobile due to a higher molecular weight. In the event that a hole pattern is formed by negative tone development, since acid is generated in many regions, it is very important to control the diffusion of acid from the exposed area to the unexposed area. The addition of onium salts including sulfonium salts, iodonium salts and ammonium salts of an α-non-fluorinated sulfonic acid and a carboxylic acid as well as the amine quencher defined herein is very important from the aspect of acid diffusion control.

The attachment of an acid generator to the polymer main chain is effective in restraining acid diffusion, thereby preventing a reduction of resolution due to blur by acid diffusion. Also roughness (LER or LWR) is improved since the acid generator is uniformly distributed.

The base polymer for formulating the positive resist composition comprises recurring units (a1) and/or (a2) having an acid labile group as essential components and additional recurring units (b), (c), (d), (e), (f1), (f2) and/or (f3) as optional components. A copolymerization proportion of units (a1), (a2), (b), (c), (d), (e), (f1), (f2) and (f3) is: $0 \le a1 < 1.0$, $0 \le a2 < 1.0$, $0 < a1+a2 < 1.0$, $0 \le b \le 0.9$, $0 \le c \le 0.9$, $0 \le d \le 0.8$, $0 \le e \le 0.8$, $0 \le f1 \le 0.5$, $0 \le f2 \le 0.5$, and $0 \le f3 \le 0.5$; preferably $0 \le a1 \le 0.9$, $0 \le a2 \le 0.9$, $0.1 \le a1+a2 \le 0.9$, $0 \le b \le 0.8$, $0 \le c \le 0.8$, $0 \le d \le 0.7$, $0 \le e \le 0.7$, $0 \le f1 \le 0.4$, $0 \le f2 \le 0.4$, and $0 \le f3 \le 0.4$; and more preferably $0 \le a1 \le 0.8$, $0 \le a2 \le 0.8$, $0.1 \le a1+a2 \le 0.8$, $0 \le b \le 0.75$, $0 \le c \le 0.75$, $0 \le d \le 0.6$, $0 \le e \le 0.6$, $0 \le f1 \le 0.3$, $0 \le f2 \le 0.3$, and $0 \le f3 \le 0.3$. Note $a1+a2+b+c+d+e+f1+f2+f3=1.0$.

For the base polymer for formulating the negative resist composition, an acid labile group is not necessarily essential. The base polymer comprises recurring units (b), (c), (d), (e), (f1), (f2) and (f3) in a copolymerization proportion: $0 < b \le 1.0$, $0 \le c \le 1.0$, $0 \le d \le 0.8$, $0 \le e \le 0.8$, $0 \le f1 \le 0.5$, $0 \le f2 \le 0.5$, and $0 \le f3 \le 0.5$; preferably $0.2 \le b \le 1.0$, $0 \le c \le 0.8$, $0 \le d \le 0.7$, $0 \le e \le 0.7$, $0 \le f1 \le 0.4$, $0 \le f2 \le 0.4$, and $0 \le f3 \le 0.4$; and more preferably $0.3 \le b \le 1.0$, $0 \le c \le 0.75$, $0 \le d \le 0.6$, $0 \le e \le 0.6$, $0 \le f1 \le 0.3$, $0 \le f2 \le 0.3$, and $0 \le f3 \le 0.3$. Note $b+c+d+e+f1+f2+f3=1.0$.

These polymers may be synthesized by any desired methods, for example, by dissolving one or more monomers selected from the monomers to form the recurring units (a1), (a2), (b), (c), (d), (e), (f1), (f2) and (f3) in an organic solvent, adding a radical polymerization initiator thereto, and effecting heat polymerization. Examples of the organic solvent which can be used for polymerization include toluene, benzene, tetrahydrofuran, diethyl ether and dioxane. Examples of the polymerization initiator used herein include 2,2'-azobisisobutyronitrile (AIBN), 2,2'-azobis(2,4-dimethyl-valeronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis as mentioned above, for thereby converting the polymer product to polyhydroxystyrene or hydroxypolyvinylnaphthalene. For alkaline hydrolysis, a base such as aqueous ammonia or triethylamine may be used. The reaction temperature is −20° C. to 100° C., preferably 0° C. to 60° C., and the reaction time is 0.2 to 100 hours, preferably 0.5 to 20 hours.

The polymer used in the resist composition should preferably have a weight average molecular weight (Mw) in the range of 1,000 to 500,000, and more preferably 2,000 to 30,000, as measured by gel permeation chromatography (GPC) versus polystyrene standards using tetrahydrofuran as a solvent. With too low a Mw, the resist composition may become less heat resistant. A polymer with too high a Mw may lose alkaline solubility and give rise to a footing phenomenon after pattern formation.

If a multi-component polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the multi-component copolymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, molecular weight or dispersity is acceptable.

The basic compound of formula (1) is advantageously used in a chemically amplified positive or negative resist composition having an acid generator added thereto. Specifically, the basic compound is added to the polymer serving as a base resin, which may be further combined with any desired components including an organic solvent, dissolution inhibitor, surfactant, crosslinker and the like to formulate a positive or negative resist composition. This positive or negative resist composition has a very high sensitivity in that the dissolution rate in developer of the polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs. Particularly when an acid generator is incorporated to formulate a chemically amplified positive resist composition capable of utilizing acid catalyzed reaction, the composition has a higher sensitivity and is further improved in the properties described above.

The positive or negative resist composition may include an acid generator in order for the composition to function as a chemically amplified positive or negative resist composition in the pattern forming process defined herein. Typical of the acid generator used herein is a photoacid generator (PAG) capable of generating an acid in response to actinic light or radiation. It is any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators. The acid generators may be used alone or in admixture of two or more. Exemplary acid generators are described in U.S. Pat. No. 7,537,880 (JP-A 2008-111103, paragraphs [0122] to [0142]).

While the resist composition of the invention should comprise the base polymer, the basic compound, and the acid generator, described above, it may further comprise an organic solvent, dissolution inhibitor, crosslinker, surfactant, acetylene alcohol, and conventional basic compound, alone or in combination.

Examples of the organic solvent used herein are described in JP-A 2008-111103, paragraphs [0144] to [0145] (U.S. Pat. No. 7,537,880). Exemplary solvents include ketones such as cyclohexanone, cyclopentanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

Any conventional basic compounds may be added along with the basic compound of formula (1) for further suppressing the diffusion rate of acid in the resist film or correcting the pattern profile. Addition of a surfactant may improve or control the coating characteristics of the resist composition.

Suitable conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl, ether, ester, lactone ring, cyano, or sulfonic acid ester group as described in JP-A 2008-111103, paragraphs to [0164], and compounds having a carbamate group as described in JP 3790649.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film loss of resist pattern or rounding of pattern top.

Exemplary surfactants are described in JP-A 2008-111103, paragraphs [0165] to [0166].

In the case of positive resist compositions, inclusion of a dissolution inhibitor may lead to an increased difference in dissolution rate between exposed and unexposed areas and a further improvement in resolution. In the case of negative resist compositions, a negative pattern may be formed by adding a crosslinker to reduce the dissolution rate of exposed area.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a weight average molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in US 2008090172 (JP-A 2008-122932, paragraphs [0155] to [0178]).

Suitable crosslinkers which can be used herein include melamine compounds, guanamine compounds, glycoluril compounds and urea compounds having substituted thereon at least one group selected from among methylol, alkoxymethyl and acyloxymethyl groups, epoxy compounds, isocyanate compounds, azide compounds, and compounds having a double bond such as an alkenyl ether group. These compounds may be used as an additive or introduced into a polymer side chain as a pendant. Hydroxy-containing compounds may also be used as the crosslinker.

Of the foregoing crosslinkers, examples of suitable epoxy compounds include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether. Suitable acetylene alcohols are described in US 2008090172 (JP-A 2008-122932).

In preferred embodiments, the respective components are used in the following amounts, provided that all amounts are expressed in parts by weight relative to 100 parts by weight of the base polymer. An amount of the PAG used is 0.1 to 50 parts, and more preferably 1 to 40 parts. An amount of the organic solvent used is 100 to 10,000 parts, and more preferably 200 to 8,000 parts. In positive resist compositions, an amount of the dissolution inhibitor blended is 0 to 50 parts, and more preferably 5 to 40 parts. In negative resist compositions, an amount of the crosslinker blended is 0.1 to 50 parts, and more preferably 1 to 40 parts. An amount of the surfactant blended is 0.0001 to 10 parts. An amount of the acetylene alcohol blended is 0 to 5 parts. An amount of the conventional basic compound other than the basic compound of formula (1) is 0 to 5 parts, and more preferably 0 to 4 parts. An amount of the polymeric quencher is 0 to 5 parts and more preferably 0 to 4 parts.

Process

The positive resist composition, typically chemically amplified positive resist composition comprising a base polymer, a basic compound of formula (1), and an acid generator in an organic solvent is used in the fabrication of various integrated circuits. Pattern formation using the resist composition may be performed by well-known lithography processes. The process generally involves coating, prebaking, exposure, post-exposure baking (PEB), and development. If necessary, any additional steps may be added.

The positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, MoSi, or $SiO_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably 80 to 120° C. for 30 seconds to 20 minutes. The resulting resist film is generally 0.1 to 2.0 μm thick.

The resist film is then exposed to a desired pattern of high-energy radiation such as UV, deep-UV, electron beam, x-ray, excimer laser light, γ-ray, synchrotron radiation or EUV (soft x-ray), directly or through a mask. The exposure dose is preferably about 1 to 200 $mJ/cm^2$, more preferably about 10 to 100 $mJ/cm^2$, or about 0.1 to 100 $\mu C/cm^2$, more preferably about 0.5 to 50 $\mu C/cm^2$. The resist film is further baked (PEB) on a hot plate at 60 to 150° C. for 10 seconds to 30 minutes, preferably 80 to 120° C. for 30 seconds to 20 minutes.

Thereafter the resist film is developed with a developer in the form of an aqueous base solution for 3 seconds to 3 minutes, preferably 5 seconds to 2 minutes by conventional techniques such as dip, puddle and spray techniques. A typical developer is a 0.1 to 5 wt %, preferably 2 to 3 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate. It is appreciated that the resist composition of the invention is best suited for micropatterning using such high-energy radiation as EB, EUV (soft x-ray), x-ray, y-ray and synchrotron radiation among others.

From the chemically amplified negative resist composition, a pattern may be formed by well-known lithography processes.

Novel Basic Compound

A basic compound with a molecular weight of at least 240 having the general formula (Q) is novel and can be advantageously used in resist compositions.

(Q)

Herein $R^{Q1}$ is hydrogen, or a straight, branched or cyclic $C_1$-$C_{30}$ alkyl, $C_6$-$C_{30}$ aryl, $C_7$-$C_{30}$ aralkyl, $C_2$-$C_{30}$ alkenyl, $C_2$-$C_{10}$ alkynyl, or $C_4$-$C_{12}$ heterocyclic-bearing group, or a combination of such groups, which group may contain a hydroxyl, mercapto, carboxyl, ether, thio ether, ester, sulfonic acid ester, sulfonyl, lactone ring, carbonyl, cyano, nitro, halogen, trifluoromethyl, amide, imide, sulfonamide, carbonate, sulfide, —N═CR—O—, —N═CR—S—, or ═N—O—N═ moiety, or $R^{Q1}$ may be an acid labile group. R is hydrogen, mercapto, hydroxyl or $C_1$-$C_3$ alkyl, or may bond with the nitrogen atom in formula (Q) to form a ring. $R^{Q2}$ is a tertiary alkyl group. $R^{Q3}$ and $R^{Q4}$ each are hydrogen or a straight or branched $C_2$-$C_4$ alkyl group, and m is an integer of 2 to 4.

Referring to formula (Q), examples of the substituent group $R^{Q1}$ may be the same as the substituent group $R^1$ in formula (1). The substituent group $R^{Q2}$ stands for a tertiary alkyl group, which may be selected from the same examples illustrated for the tertiary alkyl group of formula (A-3) wherein $R^{34}$, $R^{35}$ and $R^{36}$ are not hydrogen, included in the definition of the acid labile group $R^2$ in formula (1). The substituent groups $R^{Q3}$ and $R^{Q4}$ each stand for hydrogen or a straight or branched $C_1$-$C_4$ alkyl group. The alkyl group may be the same as exemplified for the substituent groups $R^3$ and $R^4$ in formula (1). For availability of reactants and ease of preparation, it is preferred that both $R^{Q3}$ and $R^{Q4}$ be hydrogen. The subscript m is an integer of 2 to 4. For availability of reactants and ease of preparation, it is preferred that m be 3 or 4.

The basic compound of formula (Q) should have a molecular weight of at least 240. A molecular weight of less than 240 is undesirable because a corresponding basic compound is so volatile that the profile of a resist pattern may be degraded.

The basic compound of formula (Q) may be prepared according to the following reaction scheme although the method is not limited thereto.

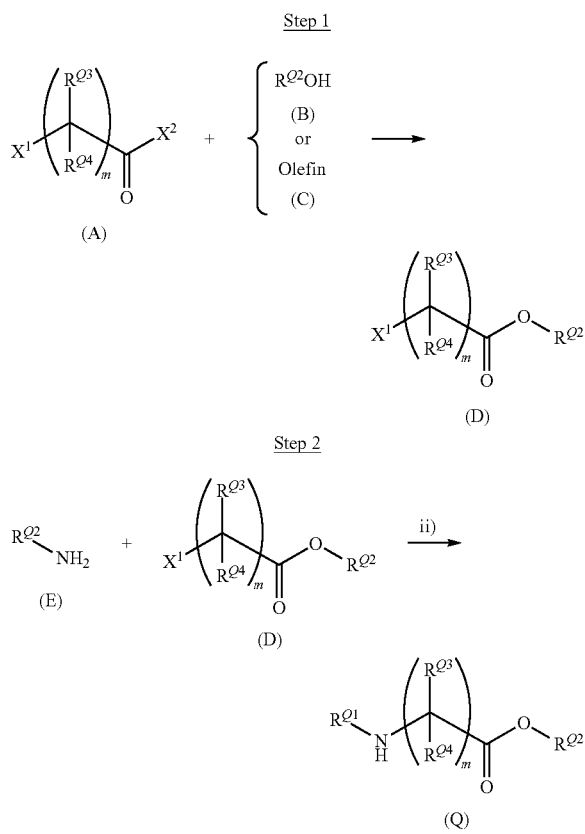

Herein $R^{Q1}$ to $R^{Q4}$ and m are as defined above, $X^1$ is halogen, and $X^2$ is halogen or hydroxyl. In the scheme, "Olefin (C)" stands for a tri- or tetra-substituted olefin obtained from elimination of $H_2O$ (i.e., dehydration) from a tertiary alcohol $R^{Q2}OH$ of formula (B).

The first reaction designated as Step 1 in the reaction scheme is a reaction of haloalkanecarboxylic acid halide (A) with tertiary alcohol (B) or haloalkanecarboxylic acid (A) with olefin (C) to synthesize haloalkanecarboxylic acid ester (D).

When haloalkanecarboxylic acid halide of formula (A) wherein $X^2$ is halogen is used as the reactant, it is preferably an acid chloride of formula (A) wherein $X^2$ is chlorine. When the acid chloride is used, the reaction may be conducted in a solventless system or in a solvent such as methylene chloride, acetonitrile, diethyl ether, tetrahydrofuran, toluene or hexane, by sequentially or simultaneously adding the corresponding haloalkanecarboxylic acid chloride such as 4-chlorobutyric acid chloride or 5-chlorovaleric acid chloride, the tertiary alcohol (B), and a base (e.g., triethylamine, pyridine, 2,6-lutidine, N,N-dimethylaniline, 4-(dimethylamino)pyridine, alkyllithium, alkylmagnesium halide or potassium carbonate), and allowing the reaction to take place while cooling or heating if necessary. An amount of tertiary alcohol (B) used is desirably 1.0 to 5.0 moles, more desirably 1.0 to 3.0 moles per mole of the reactant, haloalkanecarboxylic acid chloride (A). An amount of the base used varies with other reaction conditions, and is desirably 0 to 10 moles, more desirably 0 to 5.0 moles per mole of the reactant, haloalkanecarboxylic acid chloride (A). It is desired for higher yields that the reaction time be determined by monitoring the progress of reaction by gas chromatography (GC) or silica gel thin-layer chromatography (TLC) until the completion of reaction. The reaction time is usually about 0.5 to 24 hours. The desired haloalkanecarboxylic acid ester (D) may be recovered from the reaction mixture by ordinary aqueous work-up. If necessary, it can be purified by any standard technique such as distillation or chromatography.

When haloalkanecarboxylic acid of formula (A) wherein $X^2$ is hydroxyl is used as the reactant, the desired haloalkanecarboxylic acid ester (D) may be obtained by reacting haloalkanecarboxylic acid (A) with olefin (C) in a solvent such as toluene or hexane in the presence of an acid catalyst. The reaction may be readily carried out by a standard technique. Suitable acid catalysts include mineral acids such as hydrochloric acid, sulfuric acid, nitric acid and perchloric acid and organic acids such as p-toluenesulfonic acid and benzenesulfonic acid. The reaction may be performed by cooling or heating as desired.

The second reaction designated as Step 2 in the reaction scheme is a reaction of primary amine (E) with haloalkanecarboxylic acid ester (D) to synthesize basic compound (Q). The reaction may be readily carried out by a standard technique. The reaction may be conducted in a solventless system or in a solvent such as N-methylpyrrolidone, N,N-dimethylformamide or dimethyl sulfoxide, by sequentially or simultaneously adding the primary amine (E), the halo-ester (D), a base (e.g., pyridine, 2,6-lutidine, triethylamine or N,N-dimethylaniline), and optionally a catalytic amount of sodium iodide or tetrabutylammonium iodide, and allowing the reaction to take place while cooling or heating if necessary. An amount of primary amine (E) used is desirably 1 to 10 moles, more desirably 1 to 5 moles per mole of the reactant, haloalkanecarboxylic acid ester (D). An amount of the base used varies with other reaction conditions, and is desirably 0 to 10 moles, more desirably 0 to 5 moles per mole of the reactant, haloalkanecarboxylic acid ester (D). The reaction temperature varies with other conditions and usually ranges from 40° C. to the boiling point of the solvent. It is desired for higher yields that the reaction time be determined by monitoring the progress of reaction by gas chromatography (GC) or silica gel thin-layer chromatography (TLC) until the completion of reaction. The reaction time is usually about 0.5 to 72 hours. The desired basic compound (Q) may be recovered from the reaction mixture by ordinary aqueous work-up. If necessary, it can be purified by any standard technique such as distillation or chromatography.

EXAMPLE

Examples and Comparative Examples are given below for further illustrating the invention, but they should not be construed as limiting the invention thereto. Mw is a weight average molecular weight as measured versus polystyrene standards by gel permeation chromatography (GPC) using tetrahydrofuran as solvent, and Mw/Mn designates molecular weight distribution or dispersity. All parts (pbw and ppm) are by weight. Me stands for methyl.

Basic compounds of the invention were synthesized as follows.

Synthesis Example 1-1

Synthesis of 1-ethylcyclopentyl 4-chlorobutyrate

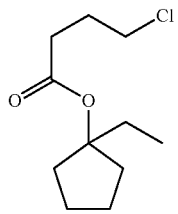

In a nitrogen atmosphere, a mixture of 69 g of 1-cyclopentyl alcohol, 118 g of 4-chlorobutyric acid chloride, and 250 g of tetrahydrofuran was ice cooled, and a mixture of 64 g of pyridine and 60 g of tetrahydrofuran was added dropwise thereto below 15° C. The reaction mixture was stirred for one day at room temperature and then ice cooled, after which 100 g of water was added dropwise to quench the reaction. This was followed by ordinary aqueous work-up and vacuum distillation (93° C./40 Pa), recovering 122 g (yield 93%) of 1-ethylcyclopentyl 4-chlorobutyrate.

Synthesis Example 1-2

Synthesis of 1-ethylcyclopentyl 4-(phenylamino)butyrate (Amine 1)

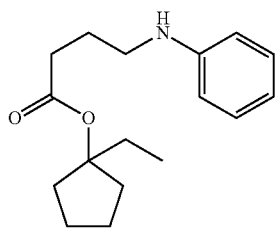 [SMILES: CCC1(OC(=O)CCCNc2ccccc2)CCCC1]

In a nitrogen atmosphere, a mixture of 15 g of 1-ethylcyclopentyl 4-chlorobutyrate, 19 g of aniline, 7.3 g of 2,6-lutidine, and 1.5 g of sodium iodide was heated at 80° C. and stirred for 36 hours at the temperature. The reaction mixture was cooled, after which 15 g of water was added dropwise to quench the reaction. This was followed by ordinary aqueous work-up and vacuum distillation (135° C./13 Pa), recovering 14 g (yield 76%) of 1-ethylcyclopentyl 4-(phenylamino)butyrate.

IR (D-ATR): ν=3403, 2966, 2876, 1724, 1603, 1507, 1449, 1435, 1380, 1322, 1261, 1164, 991, 954, 842, 750, 693 cm$^{-1}$

1H-NMR (300 MHz in DMSO-$d_6$):

δ=7.04 (2H, m), 6.50 (3H, m), 5.55 (1H, m), 2.98 (2H, m), 2.35 (2H, t), 2.10-1.85 (4H, m), 1.74 (2H, m), 1.69-1.45 (6H, m), 0.80 (3H, t) ppm

Synthesis Example 2

Synthesis of 1-ethylcyclopentyl 4-(4-methoxyphenylamino)-butyrate (Amine 2)

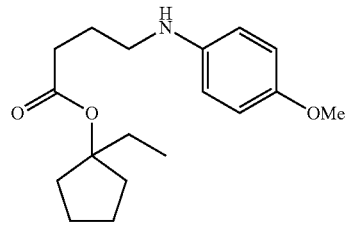 [SMILES: CCC1(OC(=O)CCCNc2ccc(OC)cc2)CCCC1]

Synthesis was performed by the same procedure as in Synthesis Example 1-2 aside from using 4-methoxyaniline instead of aniline, obtaining 1-ethylcyclopentyl 4-(4-methoxyphenylamino)butyrate (yield 73%).

Synthesis Example 3-1

Synthesis of 1-ethylcyclopentyl 4-chlorovalerate

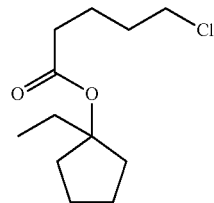

Synthesis was performed by the same procedure as in Synthesis Example 1-1 aside from using 4-chlorovaleric acid chloride instead of 4-chlorobutyric acid chloride, obtaining 1-ethylcyclopentyl 4-chlorovalerate (yield 89%).

Synthesis Example 3-2

Synthesis of 1-ethylcyclopentyl 4-(phenylamino)valerate (Amine 3)

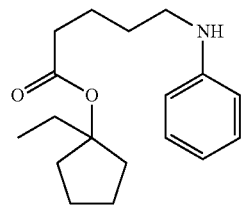 [SMILES: CCC1(OC(=O)CCCCNc2ccccc2)CCCC1]

Synthesis was performed by the same procedure as in Synthesis Example 1-2 except that 1-ethylcyclopentyl 4-chlorovalerate (Synthesis Example 3-1) was used instead of 1-ethylcyclopentyl 4-chlorobutyrate and the product was purified by chromatography with hexane and ethyl acetate. There was obtained 1-ethylcyclopentyl 4-(phenylamino)valerate, Amine 3 (yield 69%).

Synthesis Examples 4-1 to 4-39
Synthesis of Amines 4 to 42
As in Synthesis Examples 1 to 3, Amines 4 to 42 were synthesized by reacting corresponding haloalkanecarboxylic acid esters with amines.
Amines 1 to 42 are identified below by their structure.
Amine 1
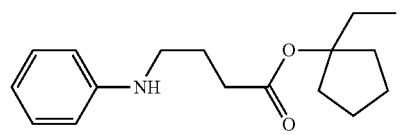
Amine 2
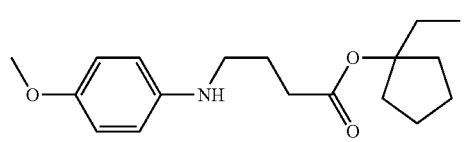
Amine 3
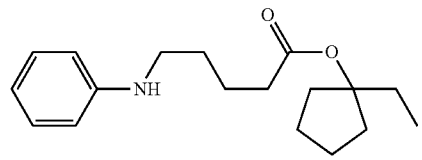
Amine 4
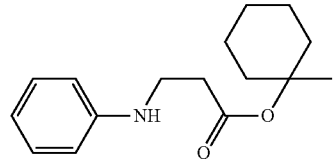
Amine 5
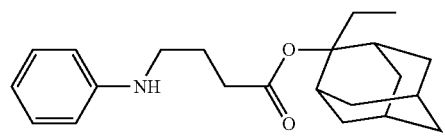
Amine 6
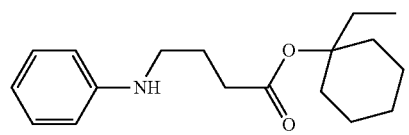
Amine 7
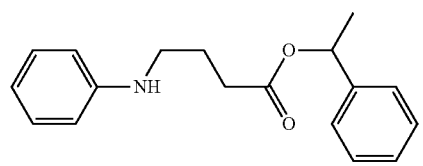
Amine 8
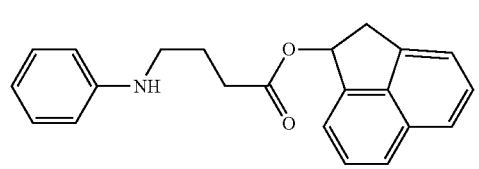
-continued
Amine 9
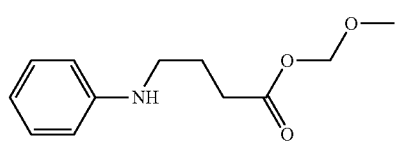
Amine 10
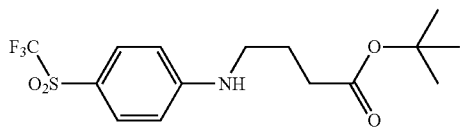
Amine 11
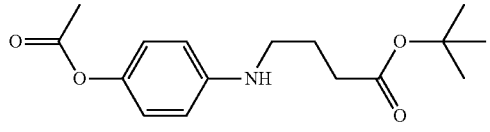
Amine 12
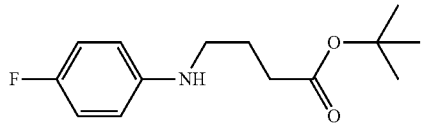
Amine 13
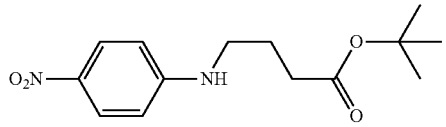
Amine 14
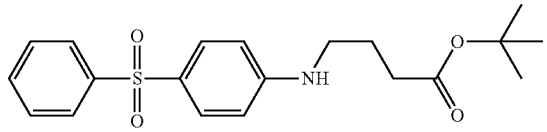
Amine 15
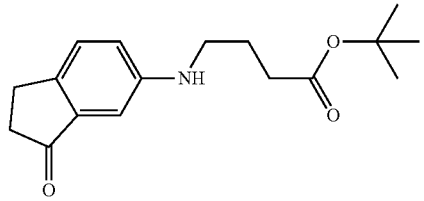
Amine 16
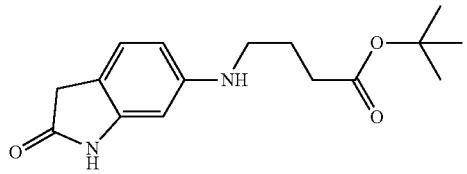
Amine 17
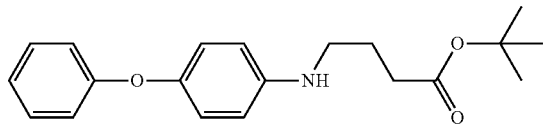

Amine 18
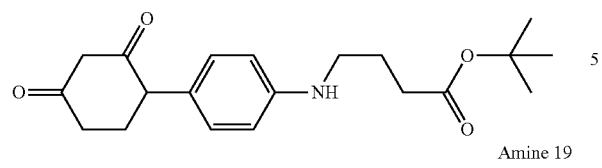
Amine 19
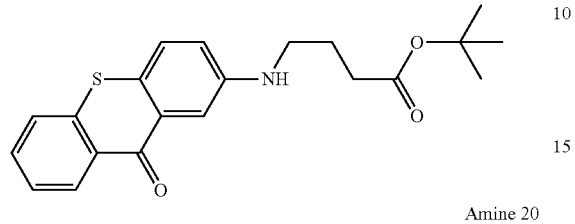
Amine 20
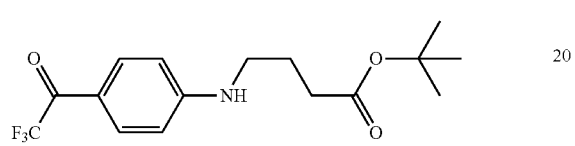
Amine 21
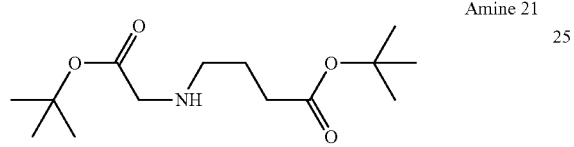
Amine 22
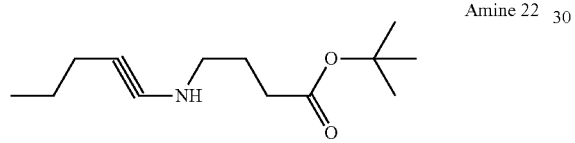
Amine 23
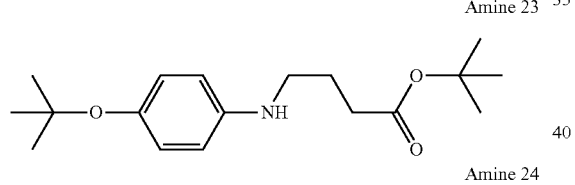
Amine 24
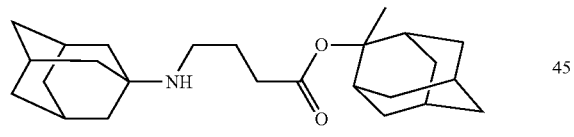
Amine 25
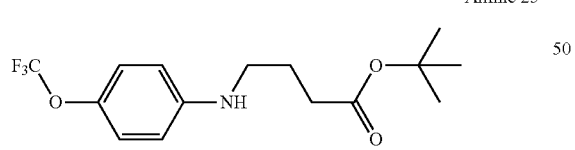
Amine 26
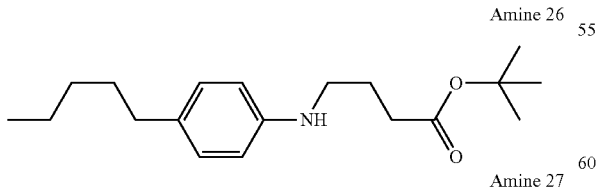
Amine 27
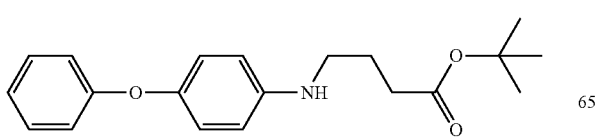
Amine 28
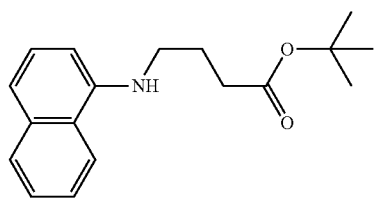
Amine 29
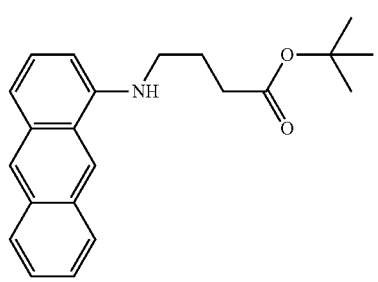
Amine 30
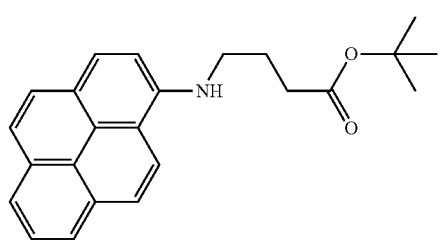
Amine 31
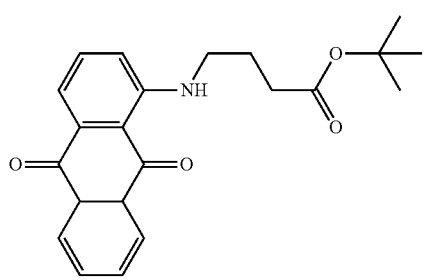
Amine 32
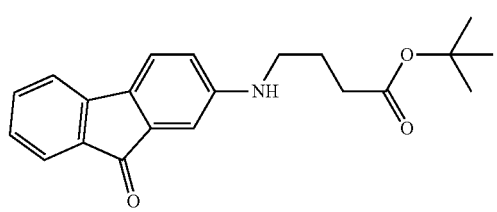
Amine 33
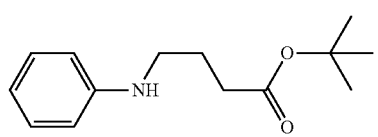
Amine 34

-continued

Amine 35
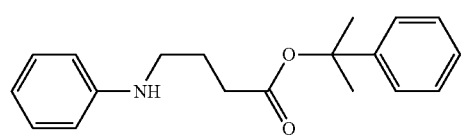

Amine 36
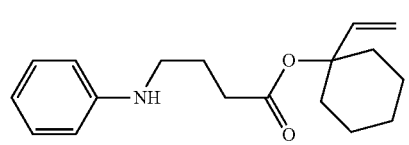

Amine 37
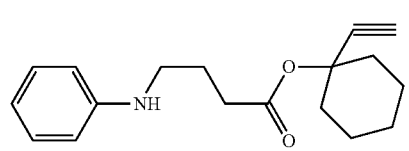

Amine 38
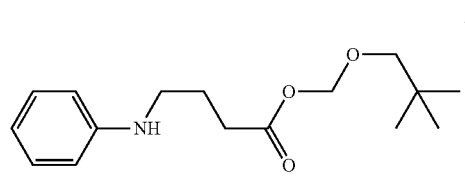

Amine 39
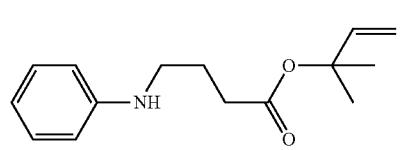

Amine 40
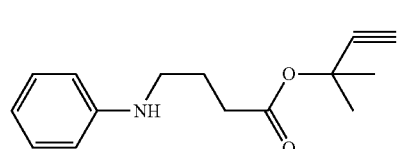

Amine 41
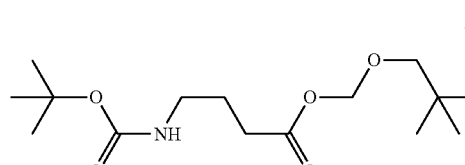

Amine 42
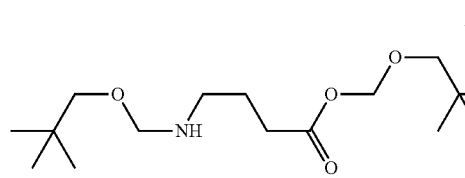

Synthesis Examples 5-1 to 5-12

Synthesis of polymers (Polymers 1 to 12)

Polymers to be added to resist compositions were prepared by combining suitable monomers, effecting copolymerization reaction thereof in tetrahydrofuran solvent, pouring the reaction solution into methanol for precipitation, repeatedly washing with hexane, isolation, and drying. The resulting polymers, designated Polymers 1 to 12, were analyzed for composition by $^1$H-NMR, and for Mw and Mw/Mn by GPC.

Polymer 1
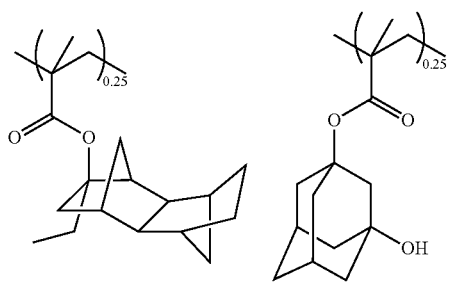
Mw = 8,500
Mw/Mn = 1.78

Polymer 2
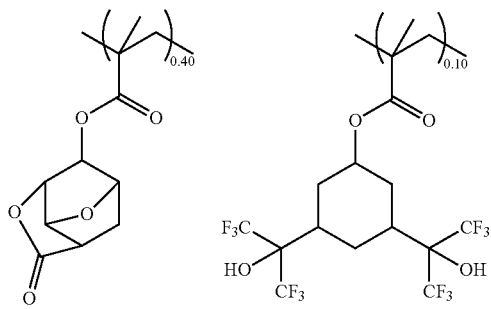

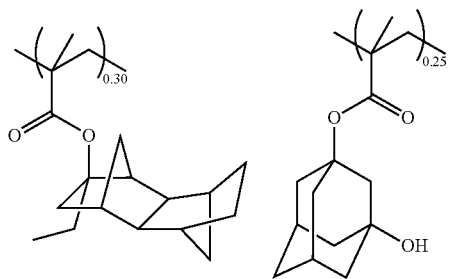

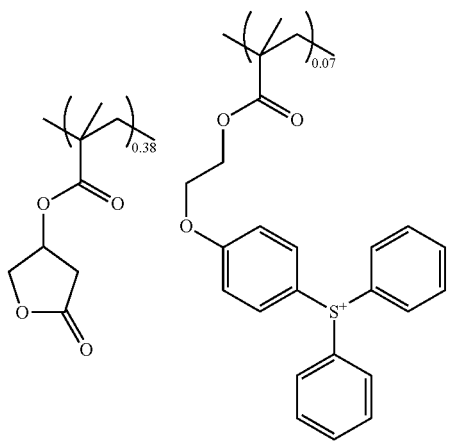

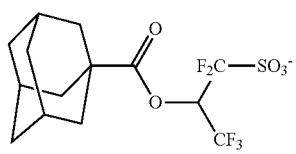
Mw = 8,700
Mw/Mn = 1.89

-continued
Polymer 3
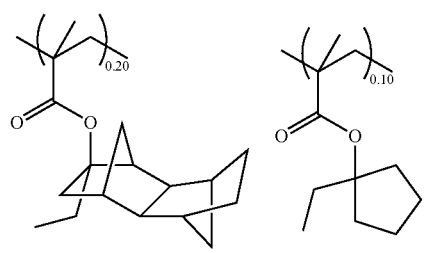
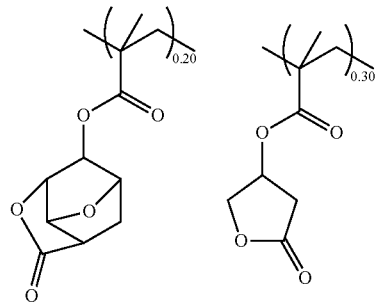
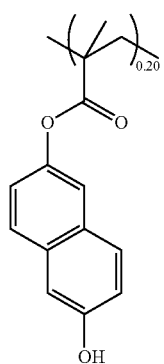
Mw = 7,600
Mw/Mn = 1.69
Polymer 4
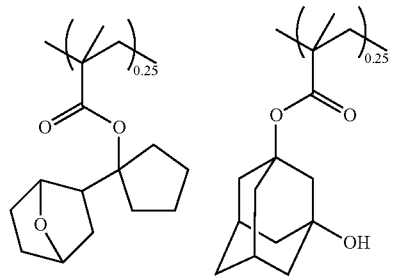
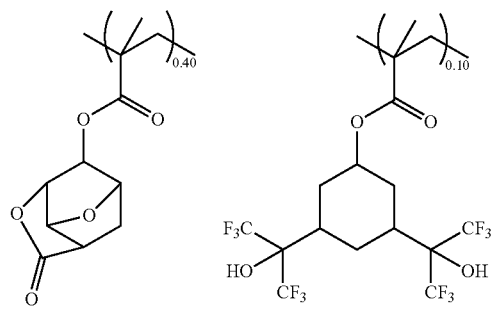
Mw = 8,900
Mw/Mn = 1.72
-continued
Polymer 5
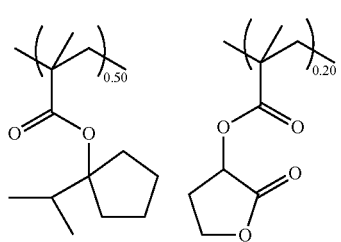
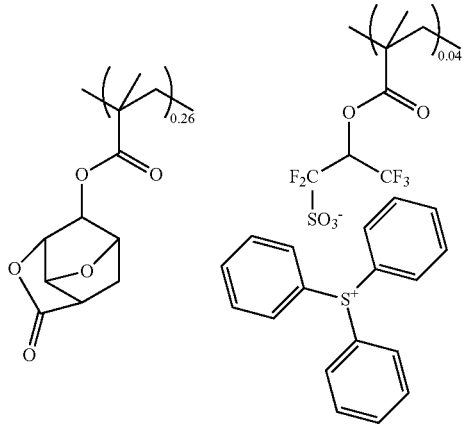
Mw = 7,800
Mw/Mn = 1.98
Polymer 6
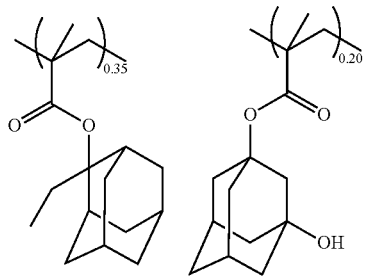
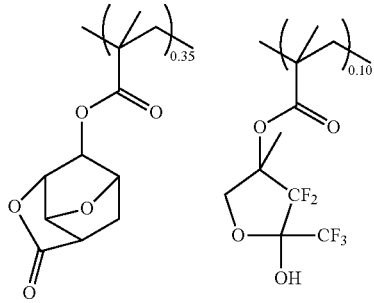
Mw = 8,500
Mw/Mn = 1.78
Polymer 7
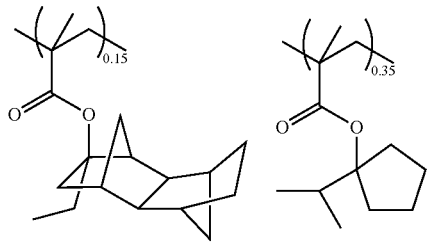

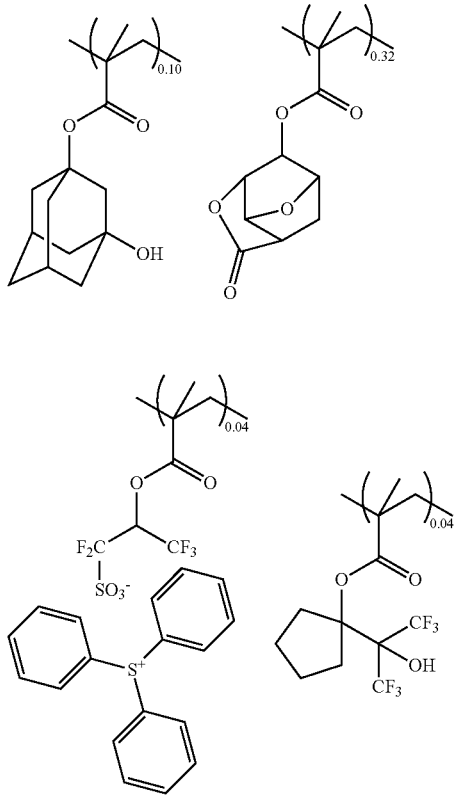
Mw = 7,900
Mw/Mn = 1.69
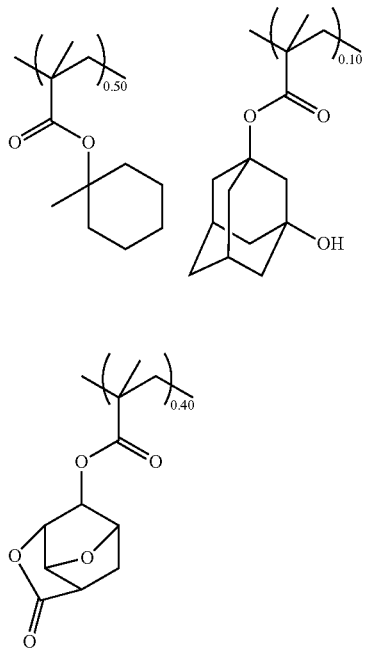
Mw = 11,300
Mw/Mn = 1.89
Polymer 8
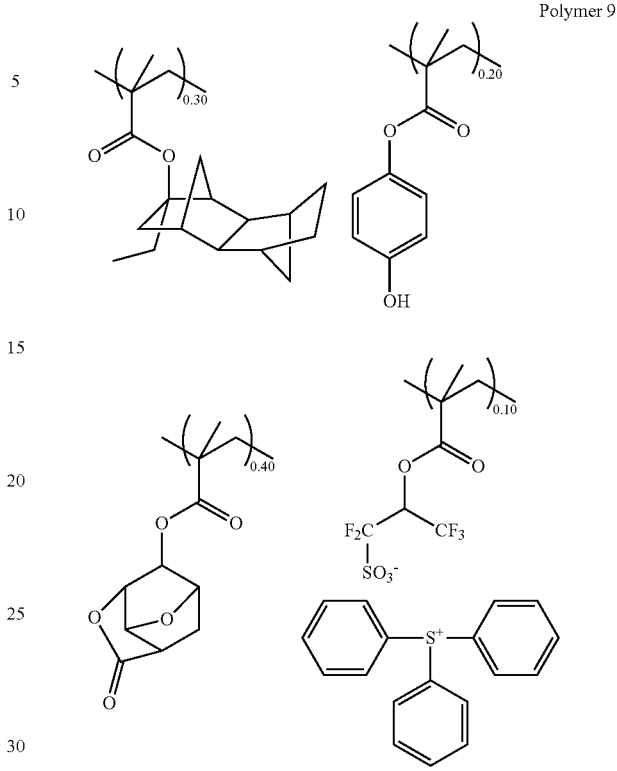
Polymer 9
Mw = 7,600
Mw/Mn = 1.73
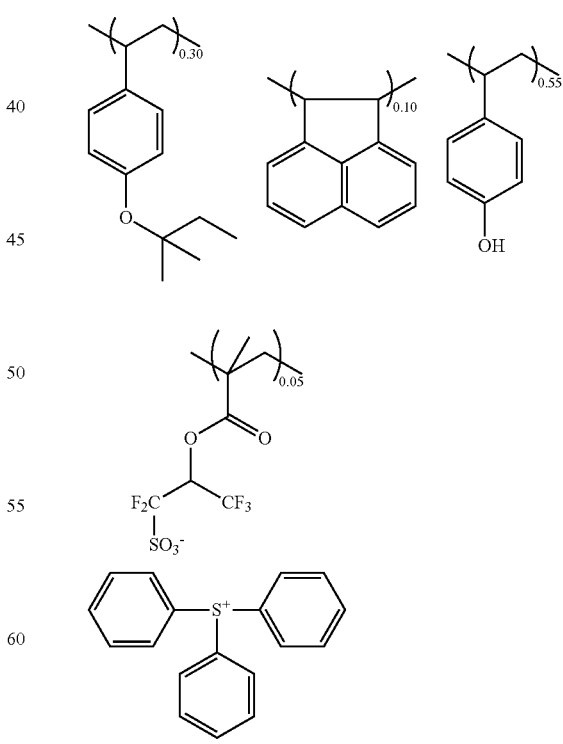
Polymer 10
Mw = 5,500
Mw/Mn = 1.76

131

-continued

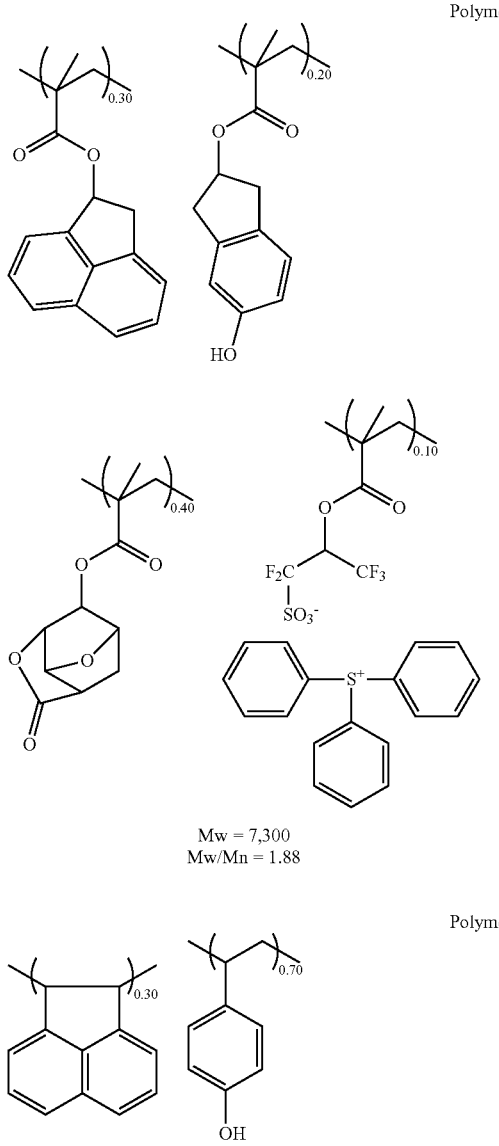

132

Acid generators: PAG1 and PAG2

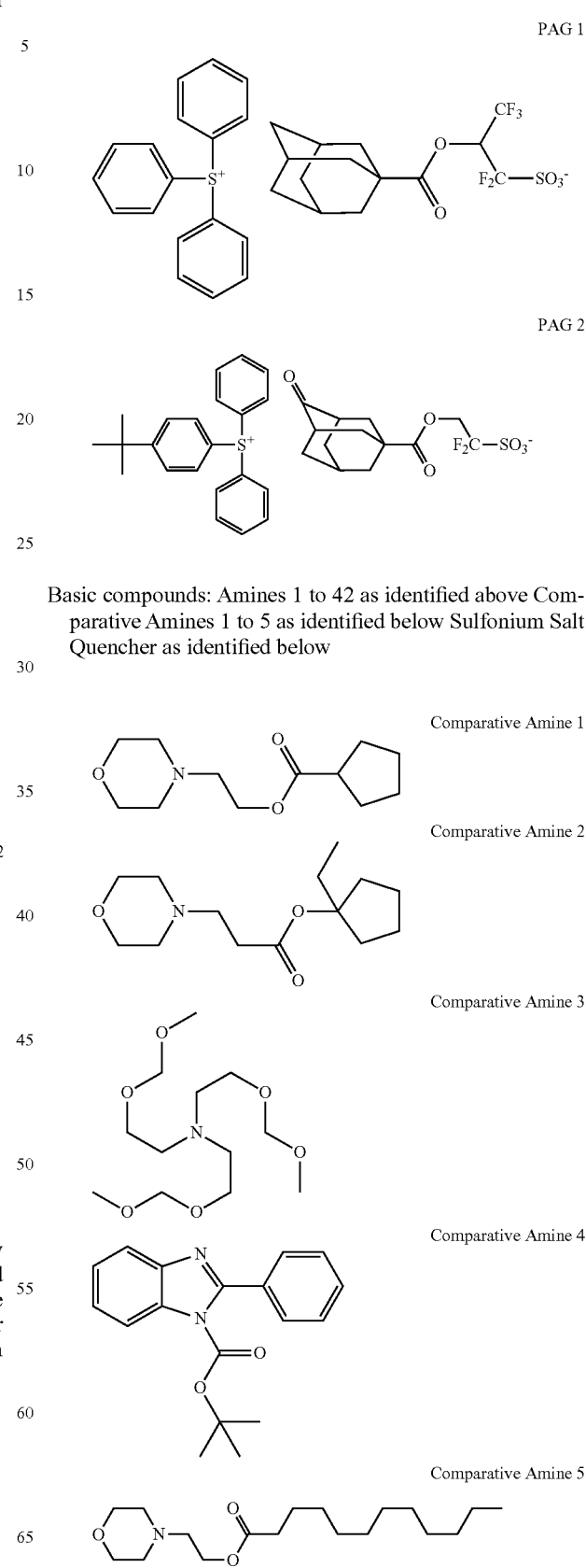

Basic compounds: Amines 1 to 42 as identified above Comparative Amines 1 to 5 as identified below Sulfonium Salt Quencher as identified below

Examples and Comparative Examples

Positive or negative resist compositions were prepared by dissolving each of the polymers synthesized above and selected components in a solvent in accordance with the recipe shown in Tables 1 to 5, and filtering through a filter having a pore size of 0.2 μm. The solvent contained 100 ppm of a surfactant FC-4430 (3M-Sumitomo Co., Ltd.).

The components in Tables 1 to 5 are as identified below.
Polymers: Polymers 1 to 12 as identified above
Organic solvents:
  propylene glycol monomethyl ether acetate (PGMEA)
  cyclohexanone (CyH)
  propylene glycol monomethyl ether (PGME)
  cyclopentanone (CyP)

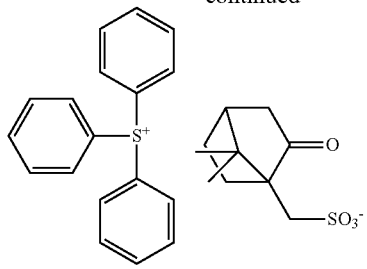

Sulfonium-salt Type Quencher

Water repellent polymer 1:

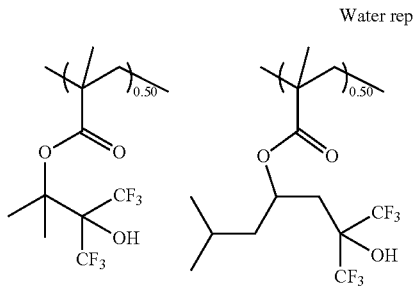

Mw = 8,900
Mw/Mn = 1.96

Crosslinker 1:

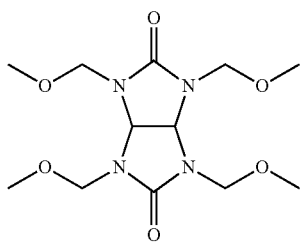

ArF Dry Lithography Test

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, each of the resist compositions in Tables 1 to 3 was spin coated, then baked on a hot plate at 100° C. for 60 seconds to form a resist film of 80 nm thick. Using an ArF excimer laser scanner model NSR-S610C (Nikon Corp., NA 1.30, σ 0.98/0.78, 35° cross-pole illumination, azimuthally polarized illumination, 6% halftone phase shift mask), the resist film was exposed through a mask bearing a pattern having a space of 70 nm and a pitch of 200 nm (on-wafer size) while varying the exposure dose and focus. The resist film was baked (PEB) at the temperature shown in Tables 1 to 3 for 60 seconds and then developed for 30 seconds with a 2.38 wt % TMAH aqueous solution, obtaining a trench pattern having a space of 60 nm and a pitch of 200 nm.

Pattern size was measured by measuring SEM (CG-4000 by Hitachi Hitechnologies Ltd.). As exposure was done in a varying dose, a sensitivity was determined as the exposure dose which produced a trench size of 60 nm. As exposure was done at a varying focus, a focus margin was determined as a depth of focus (DOF) where the trench size fell in the range of 55 to 65 nm.

The results are shown in Tables 1 to 3.

TABLE 1

| | | Polymer (pbw) | Acid generator (pbw) | Base (pbw) | Water-repellent polymer (pbw) | Organic solvent (pbw) | PEB temperature (° C.) | Sensitivity (mJ/cm$^2$) | DOF (nm) |
|---|---|---|---|---|---|---|---|---|---|
| Example | 1-1 | Polymer 1 (100) | PAG1 (10.0) | Amine 1 (2.75) | Water-repellent polymer 1 (4.0) | PGMEA (2,000) CyH (500) | 100 | 33 | 155 |
| | 1-2 | Polymer 1 (100) | PAG1 (10.0) | Amine 2 (3.05) | water-repellent polymer 1 (4.0) | PGMEA (2,000) CyH (500) | 100 | 35 | 140 |
| | 1-3 | Polymer 1 (100) | PAG1 (10.0) | Amine 3 (2.89) | water-repellent polymer 1 (4.0) | PGMEA (2,000) CyH (500) | 100 | 37 | 150 |
| | 1-4 | Polymer 1 (100) | PAG1 (10.0) | Amine 4 (2.61) | water-repellent polymer 1 (4.0) | PGMEA (2,000) CyH (500) | 100 | 42 | 135 |
| | 1-5 | Polymer 1 (100) | PAG1 (10.0) | Amine 5 (3.41) | water-repellent polymer 1 (4.0) | PGMEA (2,000) CyH (500) | 100 | 34 | 150 |
| | 1-6 | Polymer 1 (100) | PAG1 (10.0) | Amine 6 (2.89) | Water repellent polymer 1 (4.0) | PGMEA (2,000) CyH (500) | 100 | 35 | 150 |
| | 1-7 | Polymer 1 (100) | PAG1 (10.0) | Amine 7 (2.42) | Water-repellent polymer 1 (4.0) | PGMEA (2,000) CyH (500) | 100 | 36 | 150 |
| | 1-8 | Polymer 1 (100) | PAG1 (10.0) | Amine 8 (3.31) | Water-repellent polymer 1 (4.0) | PGMEA (2,000) CyH (500) | 100 | 33 | 145 |

TABLE 1-continued

|  | Polymer (pbw) | Acid generator (pbw) | Base (pbw) | Water-repellent polymer (pbw) | Organic solvent (pbw) | PEB temperature (° C.) | Sensitivity (mJ/cm$^2$) | DOF (nm) |
| --- | --- | --- | --- | --- | --- | --- | --- | --- |
| 1-9 | Polymer 1 (100) | PAG1 (10.0) | Amine 9 (2.23) | Water-repellent polymer 1 (4.0) | PGMEA (2,000) CyH (500) | 100 | 33 | 145 |
| 1-10 | Polymer 1 (100) | PAG1 (10.0) | Amine 10 (3.69) | Water-repellent polymer 1 (4.0) | PGMEA (2,000) CyH (500) | 100 | 35 | 150 |
| 1-11 | Polymer 1 (100) | PAG1 (10.0) | Amine 11 (2.93) | Water-repellent polymer 1 (4.0) | PGMEA (2,000) CyH (500) | 100 | 35 | 150 |
| 1-12 | Polymer 1 (100) | PAG1 (10.0) | Amine 12 (2.53) | Water-repellent polymer 1 (4.0) | PGMEA (2,000) CyH (500) | 100 | 35 | 150 |
| 1-13 | Polymer 1 (100) | PAG1 (10.0) | Amine 13 (2.80) | Water-repellent polymer 1 (4.0) | PGMEA (2,000) CyH (500) | 100 | 35 | 150 |
| 1-14 | Polymer 1 (100) | PAG1 (10.0) | Amine 14 (3.75) | Water-repellent polymer 1 (4.0) | PGMEA (2,000) CyH (500) | 100 | 36 | 150 |
| 1-15 | Polymer 1 (100) | PAG1 (10.0) | Amine 15 (2.89) | Water-repellent polymer 1 (4.0) | PGMEA (2,000) CyH (500) | 100 | 37 | 150 |
| 1-16 | Polymer 1 (100) | PAG1 (10.0) | Amine 16 (2.90) | Water-repellent polymer 1 (4.0) | PGMEA (2,000) CyH (500) | 100 | 35 | 150 |
| 1-17 | Polymer 1 (100) | PAG1 (10.0) | Amine 17 (3.27) | Water-repellent polymer 1 (4.0) | PGMEA (2,000) CyH (500) | 100 | 38 | 150 |
| 1-18 | Polymer 1 (100) | PAG1 (10.0) | Amine 18 (3.45) | Water-repellent polymer 1 (4.0) | PGMEA (2,000) CyH (500) | 100 | 39 | 150 |
| 1-19 | Polymer 1 (100) | PAG1 (10.0) | Amine 19 (3.69) | Water-repellent polymer 1 (4.0) | PGMEA (2,000) CyH (500) | 100 | 35 | 145 |
| 1-20 | Polymer 1 (100) | PAG1 (10.0) | Amine 20 (3.31) | Water-repellent polymer 1 (4.0) | PGMEA (2,000) CyH (500) | 100 | 39 | 155 |

TABLE 2

|  |  | Polymer (pbw) | Acid generator (pbw) | Base (pbw) | Water-repellent polymer (pbw) | Organic solvent (pbw) | PEB temperature (° C.) | Sensitivity (mJ/cm$^2$) | DOF (nm) |
| --- | --- | --- | --- | --- | --- | --- | --- | --- | --- |
| Example | 1-21 | Polymer 1 (100) | PAG1 (10.0) | Amine 21 (2.73) | Water-repellent polymer 1 (4.0) | PGMEA (2,000) CyH (500) | 100 | 33 | 155 |
|  | 1-22 | Polymer 1 (100) | PAG1 (10.0) | Amine 22 (2.25) | Water-repellent polymer 1 (4.0) | PGMEA (2,000) CyH (500) | 100 | 26 | 130 |
|  | 1-23 | Polymer 1 (100) | PAG1 (10.0) | Amine 23 (3.07) | Water-repellent polymer 1 (4.0) | PGMEA (2,000) CyH (500) | 100 | 35 | 155 |
|  | 1-24 | Polymer 2 (100) | — | Amine 2 (3.05) | Water-repellent polymer 1 (4.0) | PGMEA (2,000) CyH (500) | 95 | 38 | 155 |
|  | 1-25 | Polymer 3 (100) | PAG1 (10.0) | Amine 2 (3.05) | Water-repellent polymer 1 (4.0) | PGMEA (2,000) CyH (500) | 95 | 37 | 155 |
|  | 1-26 | Polymer 4 (100) | PAG1 (10.0) | Amine 2 (3.05) | Water-repellent polymer 1 (4.0) | PGMEA (2,000) CyH (500) | 100 | 33 | 135 |
|  | 1-27 | Polymer 5 (100) | — | Amine 2 (3.05) | Water-repellent polymer 1 (4.0) | PGMEA (2,000) CyH (500) | 90 | 40 | 160 |
|  | 1-28 | Polymer 6 (100) | PAG2 (10.0) | Amine 2 (3.05) | Water-repellent polymer 1 (4.0) | PGMEA (2,000) CyH (500) | 105 | 32 | 145 |
|  | 1-29 | Polymer 7 (100) | — | Amine 2 (3.05) | Water-repellent polymer 1 (4.0) | PGMEA (2,000) CyH (500) | 90 | 39 | 155 |
|  | 1-30 | Polymer 8 (100) | PAG2 (10.0) | Amine 11 (2.93) | Water-repellent polymer 1 (4.0) | PGMEA (2,000) CyH (500) | 100 | 38 | 150 |

TABLE 2-continued

| | | Polymer (pbw) | Acid generator (pbw) | Base (pbw) | Water-repellent polymer (pbw) | Organic solvent (pbw) | PEB temperature (° C.) | Sensitivity (mJ/cm$^2$) | DOF (nm) |
|---|---|---|---|---|---|---|---|---|---|
| | 1-31 | Polymer 7 (100) | — | Amine 15 (1.75) Sulfonium-salt Type Quencher (5.0) | Water-repellent polymer 1 (4.0) | PGMEA (2,000) CyH (500) | 100 | 40 | 140 |
| | 1-32 | Polymer 7 (100) | — | Amine 15 (1.75) Comparative Amine 4 (1.50) | Water-repellent polymer 1 (4.0) | PGMEA (2,000) CyH (500) | 100 | 38 | 145 |
| | 1-33 | Polymer 7 (100) | — | Amine 15 (1.75) Comparative Amine 5 (1.56) | Water-repellent polymer 1 (4.0) | PGMEA (2,000) CyH (500) | 100 | 36 | 145 |
| | 1-34 | Polymer 1 (100) | PAG1 (10.0) | Amine 24 (3.85) | Water-repellent polymer 1 (4.0) | PGMEA (2,000) CyH (500) | 100 | 37 | 155 |
| | 1-35 | Polymer 1 (100) | PAG1 (10.0) | Amine 25 (3.19) | Water-repellent polymer 1 (4.0) | PGMEA (2,000) CyH (500) | 100 | 37 | 150 |
| | 1-36 | Polymer 1 (100) | PAG1 (10.0) | Amine 26 (3.05) | Water-repellent polymer 1 (4.0) | PGMEA (2,000) CyH (500) | 100 | 37 | 155 |
| | 1-37 | Polymer 1 (100) | PAG1 (10.0) | Amine 27 (3.27) | Water-repellent polymer 1 (4.0) | PGMEA (2,000) CyH (500) | 100 | 37 | 150 |
| | 1-38 | Polymer 1 (100) | PAG1 (10.0) | Amine 28 (2.85) | Water-repellent polymer 1 (4.0) | PGMEA (2,000) CyH (500) | 100 | 36 | 155 |

TABLE 3

| | | Polymer (pbw) | Acid generator (pbw) | Base (pbw) | Water-repellent polymer (pbw) | Organic solvent (pbw) | PEB temperature (° C.) | Sensitivity (mJ/cm$^2$) | DOF (nm) |
|---|---|---|---|---|---|---|---|---|---|
| Example | 1-39 | Polymer 1 (100) | PAG1 (10.0) | Amine 29 (3.35) | Water-repellent polymer 1 (4.0) | PGMEA (2,000) CyH (500) | 100 | 38 | 150 |
| | 1-40 | Polymer 1 (100) | PAG1 (10.0) | Amine 30 (3.59) | Water-repellent polymer 1 (4.0) | PGMEA (2,000) CyH (500) | 100 | 40 | 145 |
| | 1-41 | Polymer 1 (100) | PAG1 (10.0) | Amine 31 (3.67) | Water-repellent polymer 1 (4.0) | PGMEA (2,000) CyH (500) | 100 | 40 | 155 |
| | 1-42 | Polymer 1 (100) | PAG1 (10.0) | Amine 32 (3.37) | Water-repellent polymer 1 (4.0) | PGMEA (2,000) CyH (500) | 100 | 39 | 155 |
| | 1-43 | Polymer 1 (100) | PAG1 (10.0) | Amine 33 (2.35) | Water-repellent polymer 1 (4.0) | PGMEA (2,000) CyH (500) | 100 | 29 | 135 |
| | 1-44 | Polymer 1 (100) | PAG1 (10.0) | Amine 34 (1.59) | Water-repellent polymer 1 (4.0) | PGMEA (2,000) CyH (500) | 100 | 20 | 130 |
| | 1-45 | Polymer 1 (100) | PAG1 (10.0) | Amine 35 (2.27) | Water-repellent polymer 1 (4.0) | PGMEA (2,000) CyH (500) | 95 | 48 | 100 |
| | 1-46 | Polymer 1 (100) | PAG1 (10.0) | Amine 36 (2.27) | Water-repellent polymer 1 (4.0) | PGMEA (2,000) CyH (500) | 95 | 50 | 100 |
| | 1-47 | Polymer 1 (100) | PAG1 (10.0) | Amine 37 (2.27) | Water-repellent polymer 1 (4.0) | PGMEA (2,000) CyH (500) | 95 | 52 | 100 |
| | 1-48 | Polymer 1 (100) | PAG1 (10.0) | Amine 38 (2.27) | Water-repellent polymer 1 (4.0) | PGMEA (2,000) CyH (500) | 90 | 55 | 100 |
| | 1-49 | Polymer 1 (100) | PAG1 (10.0) | Amine 39 (2.27) | Water-repellent polymer 1 (4.0) | PGMEA (2,000) CyH (500) | 90 | 45 | 100 |
| | 1-50 | Polymer 1 (100) | PAG1 (10.0) | Amine 40 (2.27) | Water-repellent polymer 1 (4.0) | PGMEA (2,000) CyH (500) | 90 | 49 | 100 |

TABLE 3-continued

|  |  | Polymer (pbw) | Acid generator (pbw) | Base (pbw) | Water-repellent polymer (pbw) | Organic solvent (pbw) | PEB temperature (° C.) | Sensitivity (mJ/cm$^2$) | DOF (nm) |
|---|---|---|---|---|---|---|---|---|---|
|  | 1-51 | Polymer 1 (100) | PAG1 (10.0) | Amine 41 (2.56) | Water-repellent polymer 1 (4.0) | PGMEA (2,000) CyH (500) | 90 | 38 | 100 |
|  | 1-52 | Polymer 1 (100) | PAG1 (10.0) | Amine 42 (2.59) | Water-repellent polymer 1 (4.0) | PGMEA (2,000) CyH (500) | 90 | 46 | 100 |
| Comparative Example | 1-1 | Polymer 1 (100) | PAG1 (10.0) | Comparative Amine 1 (2.27) | Water-repellent polymer 1 (4.0) | PGMEA (2,000) CyH (500) | 100 | 48 | 100 |
|  | 1-2 | Polymer 1 (100) | PAG1 (10.0) | Comparative Amine 2 (2.55) | Water-repellent polymer 1 (4.0) | PGMEA (2,000) CyH (500) | 100 | 45 | 105 |
|  | 1-3 | Polymer 1 (100) | PAG1 (10.0) | Comparative Amine 3 (2.81) | Water-repellent polymer 1 (4.0) | PGMEA (2,000) CyH (500) | 100 | 48 | 100 |
|  | 1-4 | Polymer 1 (100) | PAG1 (10.0) | Comparative Amine 4 (2.94) | Water-repellent polymer 1 (4.0) | PGMEA (2,000) CyH (500) | 100 | 46 | 90 |
|  | 1-5 | Polymer 1 (100) | PAG1 (10.0) | Comparative Amine 5 (3.13) | Water-repellent polymer 1 (4.0) | PGMEA (2,000) CyH (500) | 100 | 47 | 95 |

EB Writing Test

Each of the resist compositions in Tables 4 and 5 was spin coated onto a silicon substrate, which had been vapor primed with hexamethyldisilazane (HMDS), and pre-baked on a hot plate at 110° C. for 60 seconds to form a resist film of 80 nm thick. Using a system HL-800D (Hitachi Ltd.) at a HV voltage of 50 keV, the resist film was exposed imagewise to EB in a vacuum chamber.

Immediately after the image writing, the resist film was baked (PEB) on a hot plate at 90° C. for 60 seconds and developed in a 2.38 wt % TMAH aqueous solution for 30 seconds to form a pattern.

In the case of positive resist film, the resolution is a minimum trench size at the exposure dose that provides a resolution as designed of a 120-nm trench pattern. In the case of negative resist film, the resolution is a minimum isolated line size at the exposure dose that provides a resolution as designed of a 120-nm isolated line pattern. It is noted that Examples 2-1 to 2-17 and Comparative Example 2-1 are positive resist compositions, and Example 2-18 and Comparative Example 2-2 are negative resist compositions.

The results are shown in Tables 4 and 5.

TABLE 4

|  |  | Polymer (pbw) | Acid generator/ crosslinker (pbw) | Base (pbw) | Organic solvent (pbw) | Sensitivity (μC/cm$^2$) | Resolution (nm) |
|---|---|---|---|---|---|---|---|
| Example | 2-1 | Polymer 9 (100) | — | Amine 1 (0.91) | PGMEA (400) CyH (2,000) PGME (100) | 30 | 80 |
|  | 2-2 | Polymer 9 (100) | — | Amine 2 (1.01) | PGMEA (400) CyH (2,000) PGME (100) | 32 | 80 |
|  | 2-3 | Polymer 9 (100) | — | Amine 3 (0.96) | PGMEA (400) CyH (2,000) PGME (100) | 33 | 80 |
|  | 2-4 | Polymer 9 (100) | — | Amine 4 (0.87) | PGMEA (400) CyH (2,000) PGME (100) | 32 | 85 |
|  | 2-5 | Polymer 9 (100) | — | Amine 5 (1.13) | PGMEA (400) CyH (2,000) PGME (100) | 33 | 80 |
|  | 2-6 | Polymer 9 (100) | — | Amine 6 (0.96) | PGMEA (400) CyH (2,000) PGME (100) | 35 | 80 |
|  | 2-7 | Polymer 9 (100) | — | Amine 7 (0.81) | PGMEA (400) CyH (2,000) PGME (100) | 33 | 80 |
|  | 2-8 | Polymer 9 (100) | — | Amine 8 (1.10) | PGMEA (400) CyH (2,000) PGME (100) | 36 | 75 |
|  | 2-9 | Polymer 9 (100) | — | Amine 11 (0.98) | PGMEA (400) CyH (2,000) PGME (100) | 33 | 75 |
|  | 2-10 | Polymer 9 (100) | — | Amine 16 (0.97) | PGMEA (400) CyH (2,000) PGME (100) | 32 | 80 |

TABLE 4-continued

| | Polymer (pbw) | Acid generator/ crosslinker (pbw) | Base (pbw) | Organic solvent (pbw) | Sensitivity (μC/cm²) | Resolution (nm) |
|---|---|---|---|---|---|---|
| 2-11 | Polymer 9 (100) | — | Amine 19 (1.23) | PGMEA (400) CyH (2,000) PGME (100) | 30 | 75 |
| 2-12 | Polymer 9 (100) | — | Amine 28 (0.94) | PGMEA (400) CyH (1,600) CyP (500) | 28 | 80 |
| 2-13 | Polymer 9 (100) | — | Amine 30 (1.20) | PGMEA (400) CyH (1,600) CyP (500) | 28 | 80 |
| 2-14 | Polymer 9 (100) | — | Amine 31 (1.22) | PGMEA (400) CyH (1,600) CyP (500) | 28 | 80 |
| 2-15 | Polymer 9 (100) | — | Amine 32 (1.12) | PGMEA (400) CyH (1,600) CyP (500) | 28 | 80 |
| 2-16 | Polymer 10 (100) | — | Amine 11 (0.98) | PGMEA (400) CyH (1,600) CyP (500) | 38 | 80 |
| 2-17 | Polymer 11 (100) | — | Amine 11 (0.98) | PGMEA (400) CyH (1,600) CyP (500) | 36 | 75 |
| 2-18 | Polymer 12 (100) | PAG1 (10.0) Crosslinker 1 (8.0) | Amine 11 (0.98) | PGMEA (2,000) CyH (500) | 39 | 75 |

TABLE 5

| | | Polymer (pbw) | Acid generator/ crosslinker (pbw) | Base (pbw) | Organic solvent (pbw) | Sensitivity (μC/cm²) | Resolution (nm) |
|---|---|---|---|---|---|---|---|
| Comparative Example | 2-1 | Polymer 9 (100) | — | Comparative Amine 1 (0.68) | PGMEA (400) CyH (2,000) PGME (100) | 38 | 90 |
| | 2-2 | Polymer 12 (100) | PAG1 (10.0) Crosslinker 1 (8.0) | Comparative Amine 1 (0.68) | PGMEA (2,000) CyH (500) | 37 | 100 |

It is demonstrated in Tables 1 to 5 that resist compositions comprising a specific amine compound form patterns of satisfactory profile having an improved resolution and focus margin (DOF).

Japanese Patent Application Nos. 2010-272510 and 2011-177574 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A chemically amplified resist composition comprising a base polymer, an acid generator, and a basic compound selected from the group consisting of the following Amine 7 to Amine 23, Amine 25 to Amine 33 and Amine 35 to Amine 41:

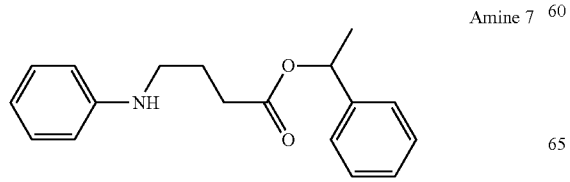

Amine 7

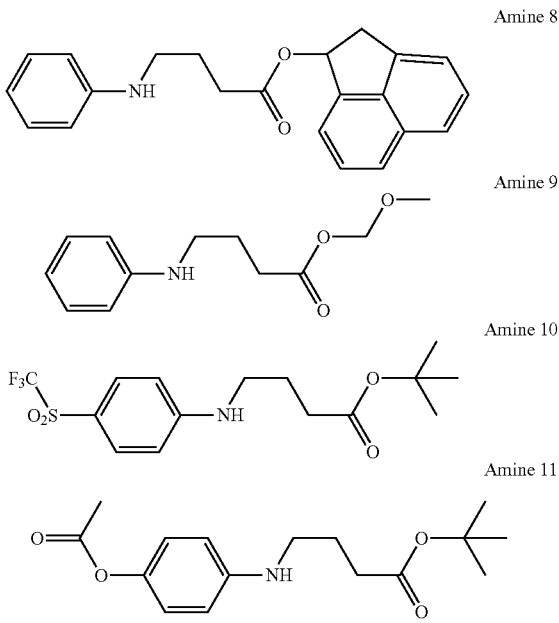

Amine 8

Amine 9

Amine 10

Amine 11

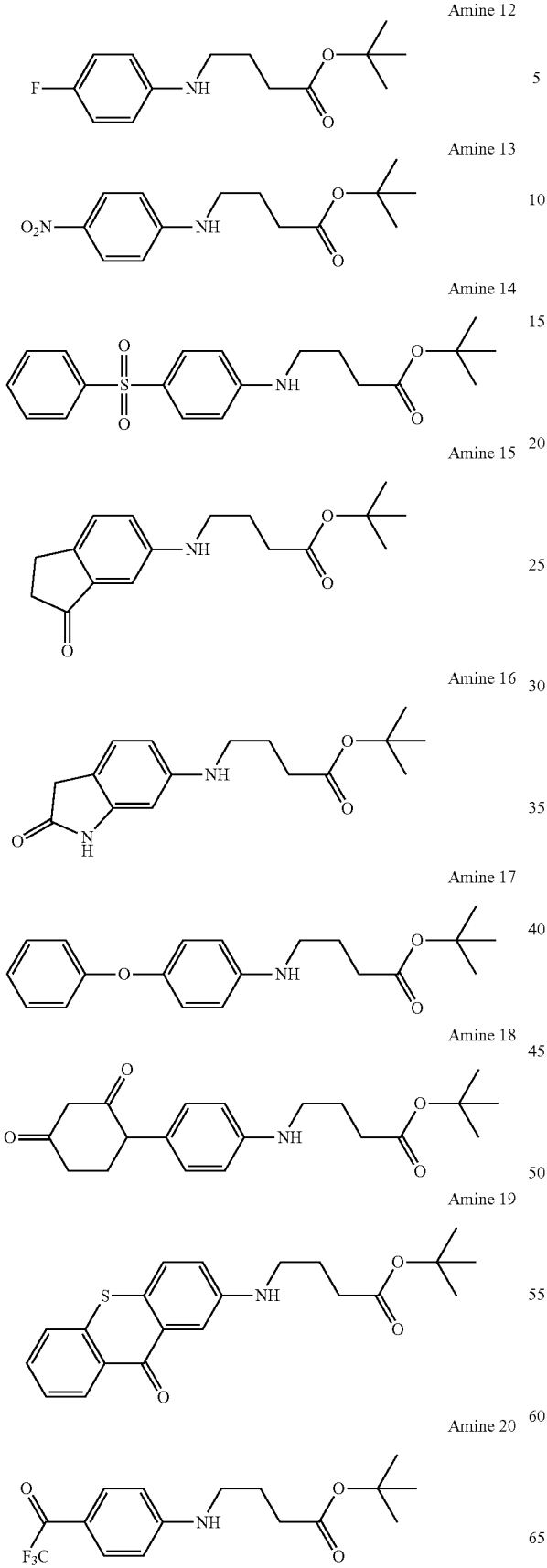
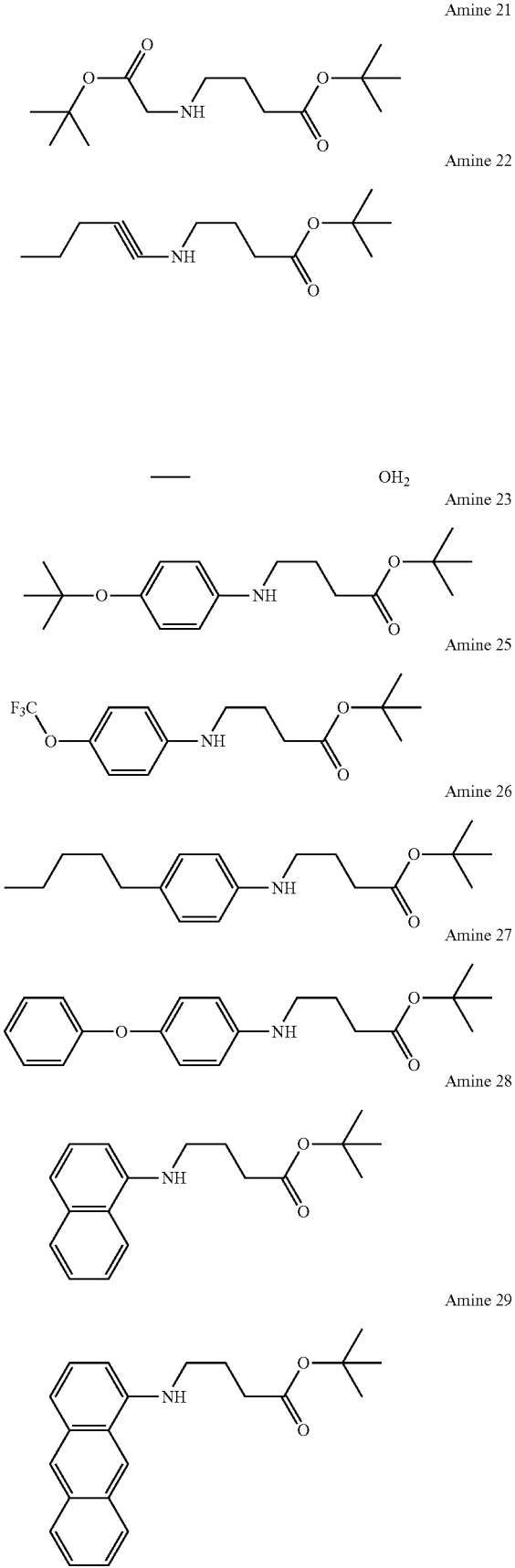

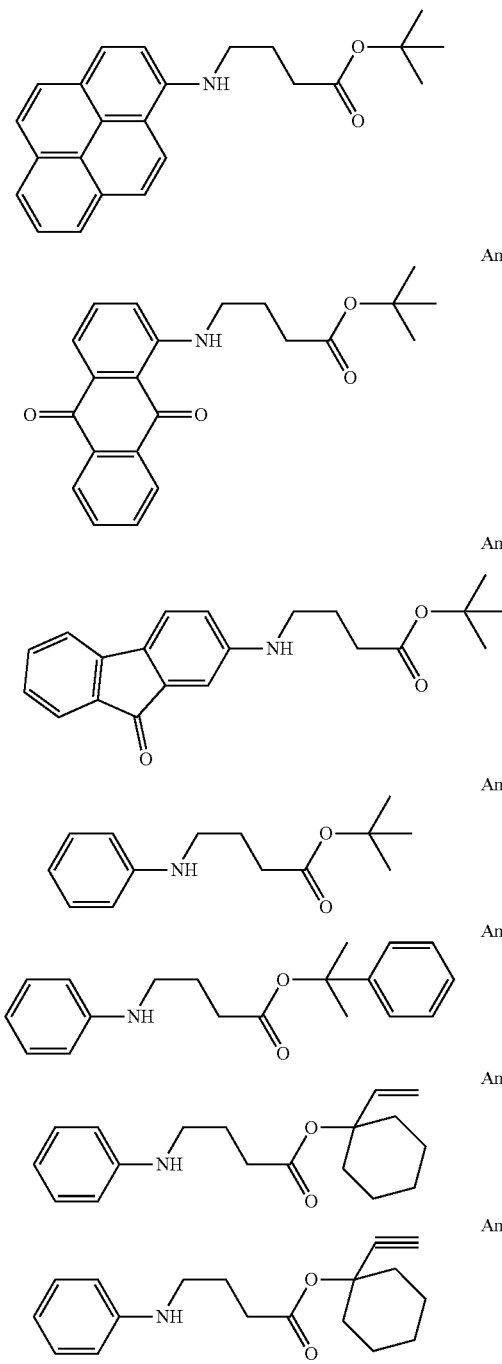
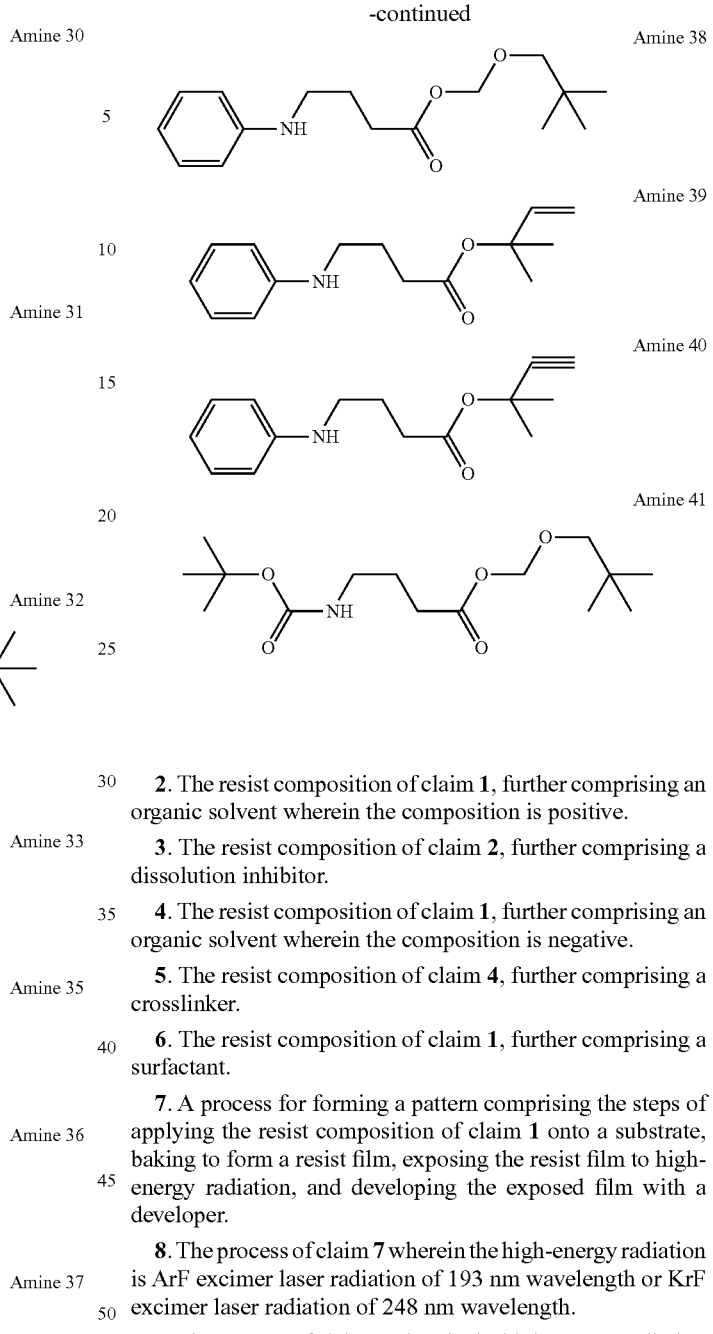

2. The resist composition of claim 1, further comprising an organic solvent wherein the composition is positive.

3. The resist composition of claim 2, further comprising a dissolution inhibitor.

4. The resist composition of claim 1, further comprising an organic solvent wherein the composition is negative.

5. The resist composition of claim 4, further comprising a crosslinker.

6. The resist composition of claim 1, further comprising a surfactant.

7. A process for forming a pattern comprising the steps of applying the resist composition of claim 1 onto a substrate, baking to form a resist film, exposing the resist film to high-energy radiation, and developing the exposed film with a developer.

8. The process of claim 7 wherein the high-energy radiation is ArF excimer laser radiation of 193 nm wavelength or KrF excimer laser radiation of 248 nm wavelength.

9. The process of claim 7 wherein the high-energy radiation is electron beam or extreme ultraviolet radiation of 3 to 15 nm wavelength.

\* \* \* \* \*